US007781218B2

(12) United States Patent
Furton et al.

(10) Patent No.: US 7,781,218 B2
(45) Date of Patent: Aug. 24, 2010

(54) IDENTIFICATION OF HUMANS THROUGH CHARACTERISTIC COMPOUNDS DETECTED IN HUMAN SCENT

(75) Inventors: Kenneth G. Furton, Miami, FL (US); Allison M. Curran, Alexandria, VA (US)

(73) Assignee: The Florida International University, Miami, FL (US)

( * ) Notice: Subject to any disclaimer, the term of this patent is extended or adjusted under 35 U.S.C. 154(b) by 79 days.

(21) Appl. No.: 12/093,677

(22) PCT Filed: Nov. 20, 2006

(86) PCT No.: PCT/US2006/045136

§ 371 (c)(1),
(2), (4) Date: Nov. 3, 2008

(87) PCT Pub. No.: WO2007/062081

PCT Pub. Date: May 31, 2007

(65) Prior Publication Data

US 2009/0081795 A1 Mar. 26, 2009

Related U.S. Application Data

(60) Provisional application No. 60/738,388, filed on Nov. 18, 2005.

(51) Int. Cl.
*G01N 33/50* (2006.01)
(52) U.S. Cl. .................. 436/63; 436/161; 436/173; 436/174; 436/178; 600/562; 600/572
(58) Field of Classification Search .................. 436/63, 436/161, 173, 174, 177, 178; 600/562, 572
See application file for complete search history.

(56) References Cited

U.S. PATENT DOCUMENTS

2008/0236249 A1* 10/2008 Fernandez de la Mora . 73/23.35
2009/0106820 A1* 4/2009 Park et al. ..................... 726/2

OTHER PUBLICATIONS

Curran et al. Proceedings of the SPIE, vol. 5779, 2005, pp. 398-408.*
Curran et al. Forensic Science Communications, vol. 7, No. 2, Apr. 2005, pp. 1-15.*
Lorenzo et al. Analytical Bioanalytical Chemistry, vol. 376, 2003, pp. 1212-1224.*
Wu et al. Abstract from Fenxi Ceshi Xuebao, vol. 22(4), 2003, pp. 21-24.*
Ostrovskaya et al. Abstract from Journal of Cosmetic Science, vol. 53 (2), 2002, pp. 147-148.*
Curran et al., "Comparison of the Volatile Organic Compounds Present in Human Odor Using SPME-GC/MS," *Journal of Chemical Ecology*, 31(7):1607-1619 (2005).
International Preliminary Report on Patentability for International Application No. PCT/US2006/045136, dated Jul. 8, 2008.
International Search Report for International Application No. PCT/US2006/045136, dated Apr. 3, 2007.
Written Opinion for International Application No. PCT/US2006/045136, dated Apr. 3, 2007.

* cited by examiner

*Primary Examiner*—Maureen M Wallenhorst
(74) *Attorney, Agent, or Firm*—Marshall, Gerstein & Borun LLP

(57) ABSTRACT

The present invention is directed to methods of identifying and/or comparing humans. More particularly, the present invention is directed to methods of collecting human scent compounds from a subject, extracting the compounds, analyzing the compounds, and correlating the compounds to a unique compound profile for the subject. These unique compound profiles can be used to distinguish one subject from another, or to identify a specific subject based upon a sample.

16 Claims, 28 Drawing Sheets

IDENTIFICATION OF HUMANS THROUGH CHARACTERISTIC COMPOUNDS DETECTED IN HUMAN SCENT

CROSS-REFERENCE TO RELATED APPLICATION

This application is a national stage application of International Application No. PCT/US06/45136, filed Nov. 20, 2006, which in turn claims the benefit of U.S. provisional application No. 60/738,388, filed Nov. 18, 2005, each of which is incorporated by reference in its entirety herein.

FIELD OF THE TECHNOLOGY

The present disclosure relates to methods of detecting and/or identifying humans through analysis of human scent compounds.

BACKGROUND

The Locard exchange principle proposes that a person can not enter or leave an area or come in contact with an object, without an exchange of materials. In the case of scent evidence, the suspect leaves his scent in the location of the crime scene itself or on objects found therein. Human scent evidence collected from a crime scene can be evaluated through the use of specially trained canines to determine an association between the evidence and a suspect. To date, there has been limited research directed to the volatile organic compounds (VOCs) comprising human odor, and their usefulness in distinguishing between individuals. In addition, the collection and preservation materials employed for human scent evidence have yet to be evaluated and optimized. The scarcity of scientific background pertaining to human odor and scent collection methods has led to successful legal challenges to the use of canine human scent discriminations for investigative purposes.

The ability of canines to discriminate human scent has been documented as early as 1887. George J. Romanes contributed many fundamental observations as to the ability of dogs to scent discriminate among humans such as the human body leaves an individual odor which a dog can distinguish, individual odors can be determined at great distances and under different environmental stresses, and canines are not deterred from scent discrimination by fragrances. Tracking canines are trained to utilize both human scent and environmental disturbances to locate the track of an individual, but are not given an initial scent to follow. Trailing canines are scented on an object, then asked to determine if the scent of the individual can be detected in an area (uncontrolled environmental conditions) and follow it to the source or until the trail ends. Human scent identification canines are presented with an individual's scent collected from a crime scene, then asked to match the odor from a selection of scents under semi-controlled environmental conditions.

The ability of dogs to match odor collected from different parts of the body has been evaluated. Dutch police dogs were shown to be able to match scent collected from hands to scent collected from the crook of the elbow from the same individual 32% of the time, which is greater than the 16.7% due to chance alone. These dogs also showed the ability to match odor collected from the hands to scent collected from pants pockets of the same individual. Studies in the United Kingdom also have shown that dogs possess the ability to match scent to that of an individual taken from various places of the body with a success rate above 80%, compared to a chance rate of 16.7%.

A study conducted in the United States produced different results. In the evaluation of the ability of canines to match odor collected from different parts of the body, odors were collected using forceps and metal bars. The canines were trained to distinguish between individuals based on hand odor. In the first part of the experiment, the canines were successful in matching a hand odor sample to the correct scent in an array of hand scented objects. In the second part of the experiment, the dogs were required to match hand odor to objects scented by the crook of the elbow by different individuals. The canines were only successful in the identifications 57.9% of the time which was not statistically higher than that due to chance. It was concluded that the inability of the canines to correctly match hand odor and elbow odor brings into question dogs' ability to generalize an individual's odor signature and cross match samples taken from different parts of the body. The lack of controls leading to ambiguous scent matching and appropriate training for the canines used in the U.S. experiment was intentional to evaluate whether canines that have been trained to match odor from a specific part of the body will automatically generalize odors when faced with odors from different areas of the body. Justification for the ambiguity was that a strict interpretation of the individual odor theory would suggest that canines have the ability to automatically generalize odors. The canines did not demonstrate an automatic ability to generalize odors, highlighting the importance of correct training procedures for scent identification canines in order to allow the canine to be able to generalize odors successfully.

Use of canines in identifying a subject has been used with varying success by law enforcement across the globe. What has yet to be addressed is a systematic means of identifying a subject using instrumental analysis, wherein both collection techniques and storage of collection samples are addressed.

SUMMARY

The present disclosure is directed to methods of identifying or characterizing subjects, typically humans, by analyzing compounds in a scent sample from that subject. More particularly, the present disclosure relates to methods of analyzing scent compounds to identify specific compounds and concentrations. The identity and concentrations of these scent compounds are unique between individuals and such a scent profile can be used to distinguish two or more individuals.

Thus, one aspect of the present disclosure provides a method of identifying or characterizing a subject comprising extracting human scent compounds from a sample and analyzing the compounds to determine the identity and relative amounts of each human scent compound, where the identity and relative amount of the human scent compounds identifies or characterizes the human. A scent compound refers to a compound which is released by skin secretions or emanates from a human's body. Such compounds are listed below in Table 36.

In some embodiments, the method further comprises collecting the sample. Collection of the scent compounds comprises use of a collection fabric (e.g., a cotton gauze, a swab, or any fabric suitable for use in collecting a sample). Because the scent compounds of interest can also exist as background compounds already in a collection fabric, the collection fabric can be cleansed prior to use. Such cleansing techniques include extracting compounds from the collection fabric via supercritical fluid extraction (SFE). Because SFE can be less efficient for polar compounds (such as aldehydes), a modifier can be added to increase solubility of polar compounds.

Modifiers include water, methanol, ethanol, propanol, isopropanol, and combinations thereof.

The collection of the scent compounds can be via a variety of techniques, but typically is via contact of the collection fabric close to the skin for a period of time sufficient to allow the scent compounds to collect on the collection fabric or via wiping the subject with a collection fabric. When the collection is via contact of a collection fabric, the collection fabric is typically in contact with the subject for at least 10 minutes, and can be in contact at least 15, at least 20, or at least 30 minutes. The contact of the collection fabric to the subject can be either indirect or direct. Direct contact includes holding, rubbing, and/or wearing a collection fabric for a period of time sufficient to collect human scent compounds for subsequent analysis. Indirect contact includes having a collection fabric near a subject so as to collect any exuded or emitted compounds from that subject but not in actual direct contact with the subject. For example, a collection fabric can be held close to a subject to collect a sample while never actually touching the subject's skin or body.

Whether the collecting is via contact or wiping a collection fabric, the collecting can be at one or more areas of the subject's body, e.g., the palm, the foot, and/or the axilla (armpit).

Extraction of the scent compounds from the sample typically comprises solid phase micro-extraction (SPME) techniques. Because the scent compounds of interest typically are volatile, a SPME headspace analysis is a preferred method. SPME headspace analysis involves exposure of a fiber above a sample of interest in an enclosed space for a sufficient period of time to allow extraction of the scent compounds onto the fiber. Typically the exposure is at least 10 hours, but can be at least 15 hours, at least 20 hours, or at least 24 hours. The fiber then is analyzed, and the identity and/or concentration of the scent compounds determined. The analysis of the fiber typically is via gas chromatography, mass spectrometry, or a combination thereof. The fiber can be Carbowax/Divinylbenzene (CW/DVB), Polydimethylsiloxane (PDMS), Polydimethylsiloxane/divinylbenzene (PDMS/DVB), Carboxen/Polydimethylsiloxane) (CAR/PDMS), or Divinylbenzene/Carboxen on Polydimethylsiloxane (DVB/CAR/PDMS).

Identification and determination of amounts of the scent compounds comprises comparing concentrations of individual scent compounds to each other to create a profile of scent compounds for the subject from which the scent compounds was collected. Identification of compounds can be via any now known or later developed analytical technique. Typically, the analysis is done via chromatography and/or spectroscopy. Nonlimiting examples of analytical techniques include gas chromatography, liquid chromatography, capillary electrophoresis, mass spectrometry, nuclear magnetic spectroscopy, and the like.

A scent profile typically is unique to each individual, and therefore can be used to distinguish one subject from another. When there are at least two subjects, analysis of each subject's scent compounds can result in unique scent profiles, allowing for a distinction between the subjects. Such distinction can be useful in law enforcement and other such types of applications. In comparing two or more subjects, it may be desired to control for environmental and/or dietary compounds. In such instances, the subjects are samples on a multiplicity of days, and only those compounds which are present in each of the subject's samples will be used to create the scent profile (e.g., the relative concentrations of scent compounds).

DETAILED DESCRIPTION

Figure 1:
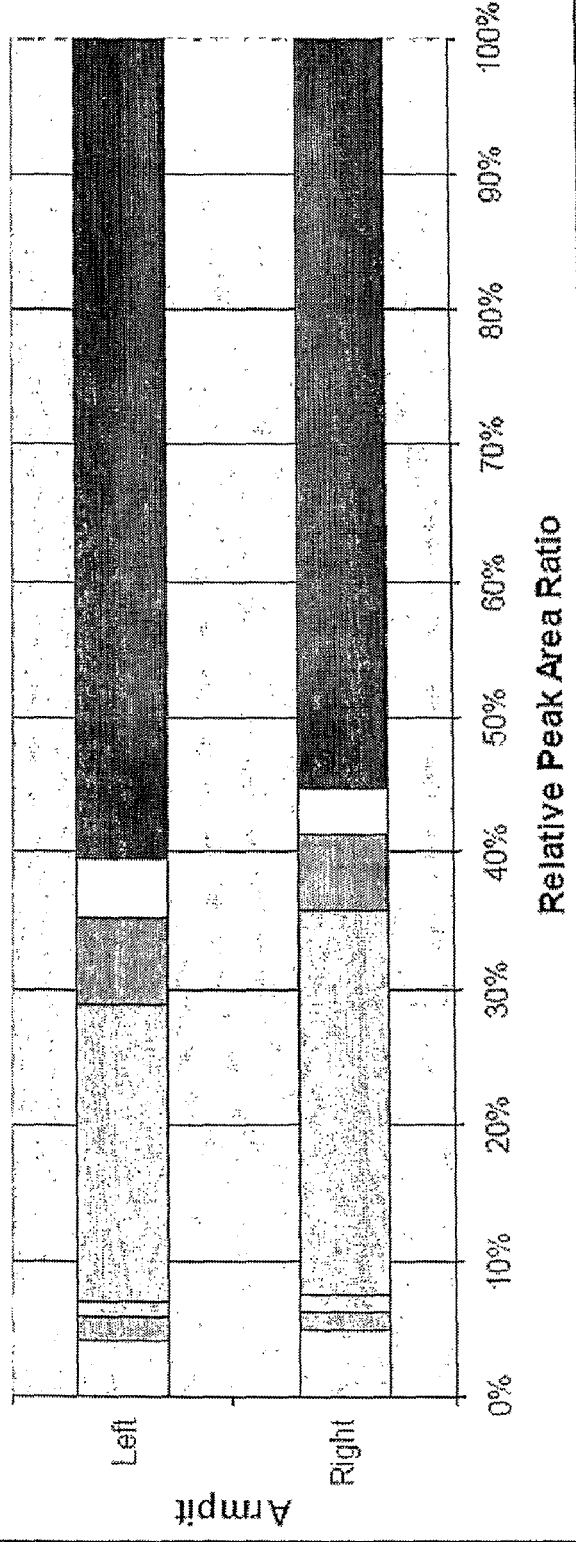
FIG. 1 shows a comparison of relative amounts of human scent compounds extracted from the left and right armpit of a human subject.

Disclosed herein are methods of detecting and/or identifying humans by analyzing compounds in human scent.

Production of Human Scent

The production of human scent is a complicated process that is yet to be fully understood. It is known that the epidermis (outer) layer of the skin constantly sheds epithelial cells into the environment. The surface of the skin contains about two billion cells, of which 1/30 are being shed daily (approximately 667 cells per second). The average lifespan of an epithelial cell is approximately 36 hours. Dead cells which are shed from the surface of the skin are referred to as "rafts," which are approximately 14 microns in size and weigh approximately 0.07 micrograms. The "raft" is composed of one or more dead cells, approximately four microbial bacteria, and body secretions. All three components of the "raft" are said to be characteristic to the individual. Each "raft" also is said to be surrounded by a vapor cloud which results from bacterial action upon the cells. Studies have shown that there is a current of warm air which surrounds the human body. The current of warm air is approximately one third to one half inch thick, and it travels up and over the body at a rate of 125 feet per minute. Analysis of the air current showed that it contained four to five times as many germs as the air in the rest of the sampling room. The germs come from the bacteria that are shed with dead skin cells. Larger flakes of skin fall to the ground, but smaller flakes are drawn up into the current. These currents also can be visualized running along the outside of clothing. The warm air currents are said to carry the "rafts" from the body into the surrounding area, thereby allowing for the deposit of human scent in the environment.

Short-medium chain ($C_2$-$C_{12}$) volatile fatty acids (VFAs) contribute to axillary malodor. A potential route to VFAs in the axilla is through the bio transformation of longer chain ($C_{14}$-$C_{30}$), structurally unusual (methyl branched and or odd carbon number) fatty acids present in the sebum. In an in vitro study on the formation of VFAs from bacterial action, the fermentation of representative axillary Propionibacterium (P. avidum and P. acnes) and Staphylococcus (S. epidermidis) species were combined with substrates, such as glycerol and lactic acid, which are readily available in the axillary region. Interaction of P. avidum with both substrates resulted in the generation of significant quantities of propionic acid ($C_3$) and acetic acid ($C_2$) also was produced from interaction with lactic acid. P. acnes also produced significant levels of both propionic and acetic acid through interaction with lactic acid. However, interaction with glycerol produced no acetic acid and only a small quantity of propionic acid. The Staphylococcus bacteria metabolized both glycerol and lactic acid producing large amounts of both acetic acid and propionic acid. This indicates that the fermentation pathways by cutaneous propionibacteria and staphylococci produce short chain ($C_2$-$C_3$) VFAs on axillary skin. Representative Staphylococcus, Corynebacterium, and Propionibacterium species were incubated for up to 72 hours with valine, leucine, and isoleucine to evaluate their ability to generate metabolites of these branched aliphatic amino acids. Only Staphylococcus species formed odorous metabolites from these amino acids producing significant levels of branched VFAs ($C_4$-$C_5$). The results indicated that VFA production by Staphylococcus increases significantly with increasing oxygen availability. Growth also was optimal under aerobic conditions. These two observations imply that biotransformation activity is linked to overall metabolic activity.

The hypothesis that human scent is produced through bacterial action on dead skin cells and secretions is the most common depiction of the creation of human odor. Other studies have suggested that odor is formed very quickly, supporting the idea that odor production is due to simple bond cleavage as opposed to a complex bacterial action. Comparisons of the extracts of axillary sweat collected from both males and females showed qualitative similarities in the volatile organic acids present, suggesting a similar origin and mechanism for odor production in men and women.

Axillary odor has been shown to consist of at least four androst-16-enes (androstenone, androstadienol, androstenol, and androstadienone) and isovaleric acid as determined through analysis of axillary secretions. The androst-16-enes and isovaleric acid provide the musky, urinous, and sweaty odors associated with axillary odor. The androst-16-enes are mammalian pheromones which are directly involved in the mating behavior of the pig. Axillary secretions have also been determined to contain sulfanylalkanols, including 3-methyl-3-sulfanylhexan-1-ol, 3-sulfanylhexan-1-ol, 2-methyl-3-sulfanylbutan-1-ol, and 3-sulfanylpentan-1-ol. Other compounds have been identified as well, including aldehydes.

Compounds present in both male and female axillary secretion extracts that contained the characteristic malodors present in the axillary region have been isolated and identified. These analyses showed the presence of several $C_6$-$C_{10}$ straight chains, branched, and unsaturated acids, and the major odor-causing compound was determined to be (E)-3-methyl-2-hexenoic acid. Other important odor contributors were terminally unsaturated acids, 2-methyl $C_6$-$C_{10}$ acids, and 4-ethyl $C_5$-$C_{11}$ acids. Comparison of the male and female extracts showed qualitative similarities. Generically, branched and unsaturated compounds seem to have a high odor impact. (E)-3-methyl-2-hexenoic acid (saturated and branched) is a major contributor to axillary odor. The Z isomer has a high odor impact, but is present at one tenth the concentration of the E isomer. The chain length and branching of the acids found suggest that the precursors for the acids are probably not amino acid-like in composition. In addition, odor occurs quickly, which suggests that odor may be cause by simple bond cleavage and not by complex bacterial action.

The genetic basis for individualizing body odors has been studied extensively in genetically engineered mice which differ in respect to the genes present in the major histocompatibility complex (MHC). Individual body scents of mice can be altered by modification of a single gene within the MHC. Such alterations result in changes in the concentrations of the volatile components found in the mouse's urine. The MHC is a group of genes connected to the immune system, and has been shown to play a role in both maternal and kin recognition in mice. In humans, the major histocompatibility complex is referred to as the HLA, which is short for human leucocyte antigens. The MHC consists of polymorphic genes which contain extreme nucleotide diversity as high as 8.6%, as compared to the nucleotide diversity of the human genome which has been estimated to be between 0.08% and 0.2%. Experiments utilizing trained rats have shown that urine odors of defined HLA-homozygous groups of humans can be distinguished. Electronic nose technology also has shown the ability to discriminate between urine and serum from HLA-homozygous groups of individuals. The pathway through which the MHC influences odors is not known. A model integrating different hypotheses suggests that soluble MHC proteins play a central role in the production of MHC associated odors. The soluble MHC proteins travel into the serum, both intact molecules and degraded moieties of the proteins have been found in the urine and in the sweat, and it is suggested that, through bacterial action, they are transformed into odorous substances.

Collection of Human Scent

There are two main methods of collecting human scent for the purpose of scent identification. The direct method is collecting a handled object which can then be analyzed, and the indirect method is collecting the odor on an absorber from an object or an individual, then analyzing the collected odor. Police have collected human scent from objects by placing an "odor collecting cloth" in contact with the object for 20-25 minutes. After the time allotment has passed, the cloths are removed using deodorized tweezers, folded so that the surface which was in contact with the object is on the inside, and sealed inside a glass jar. A scent collection tool called the Scent Transfer Unit-100 (STU-100) has been developed to aid law enforcement in the collection of human scent from both people and objects utilizing sterile gauze absorbers. The STU-100 can be used for both contact (placing the object directly on the gauze) and non-contact scent collection (placing the STU-100 directly over the object). There are many variations to the process of collection of scent on an absorber ranging from wiping the object or surface, placing the absorber in contact with the object or surface, or utilizing the STU-100. At a crime scene, any object that may have been touched by the suspect can be collected as scent evidence. Items that are commonly collected for human scent evidence purposes include clothing, lighters, and tools. However, some items are too large to collect, and indirect collection of scent is used, such as car seats, doors, and windows. These items are similar to those where DNA was successfully extracted, therefore making scent collection at crime scenes of likely use.

Polyester materials have been used for the collection and analysis of human scent by canines and instrumental methods. Cotton is the most widely reported type of material used for human odor collection for both canines and instruments. Nevertheless, no mention of the percent composition or sterile-ness of the fabrics has previously been reported. Canines have shown a natural ability to discriminate between odors in the presence of a high background, whereas instrumental analysis requires a significantly lower background.

Sterilization is a process intended to kill or remove all types of micro-organisms. In general, there are three principal sterilization methods used for most surgical dressing materials: (1) physical (dry heat or saturated steam), (2) chemical (ethylene oxide gas or chemical liquids), and (3) radiation sterilization. Steam sterilization is commonly referred to as autoclaving, which relies on the use of steam above 100° C. Traditionally, gravity (downward-displacement) autoclaves have been utilized for the sterilization of dressings. However, high-vacuum porous-load steam sterilizers are now the method of choice. Essential requirements include a total removal of air from load and the prevention of excessive condensation within the dressing pack during the cycle. The nature of the packing must allow complete steam penetration into the dressing, as well as post-sterilization drying. Ethylene oxide gas is effective against all type of micro-organisms. The biocidal action of this gas is alkylation of nucleic acids. It is non-corrosive and safe for most plastic and polyethylene materials. The operating pressures and temperatures (45-60° C. and 10-12 psi) of ethylene oxide sterilizers are considerably less than the conditions for steam units. Another resource for sterilization treatment is gamma radiation. Gamma radiation efficiently kills microorganisms throughout the product and packaging with very little temperature effect. The advantages of gamma radiation lie in the precise dosing, rapid processing, uniform dose distribution, system flexibility, and the immediate availability of product after processing. Biologically sterile, however, may not equate to analytically clean, and thus the collection medium may prove to be a limiting factor for the instrumental identification of the compounds present in a human odor profile and thus an optimization of these materials is required.

The make-up of natural fiber products are considerably more complex than man-made fires and exhibit a greater diversity in surface chemistry, which may be exploited to optimize the absorptive potential of the textile gauze. Natural protein fibers are polyamidic in nature. Silk is predominantly aliphatic in its side-chains and the acid and hydroxyl side chain groups are observed more often than the basic groups. Wool exhibits a more even spread of chemistries, although glutamic acid is one of the most abundant side chains (Table 1). Cellulose fibers (cottons) have a large number of hydroxyl groups, resulting in increased absorbency and affiliation for polar species via hydrogen-bonding. Depending on which types of compounds the canines are using to distinguish between people, the functional groups present on the surface of the material may lead to an increased ability to collect human scent from handled objects and people.

TABLE 1

| TYPE | AMINO ACID | MASS PERCENT OF AMINO ACID | |
|---|---|---|---|
| | | Silk Fibroin | Wool Keratin |
| Inert | Glycine | 43.8 | 6.5 |
| | Alanine | 26.4 | 4.1 |
| | Valine | 3.2 | 5.5 |
| | Leucine | 0.8 | 9.7 |
| | Isoleucine | 1.37 | — |
| | Phenylalanine | 1.5 | 1.6 |
| Acidic | Aspartic Acid | 3.0 | 7.27 |
| | Glutamic Acid | 2.03 | 16.0 |

TABLE 1-continued

| TYPE | AMINO ACID | MASS PERCENT OF AMINO ACID | |
|---|---|---|---|
| | | Silk Fibroin | Wool Keratin |
| Basic | Lysine | 0.88 | 2.5 |
| | Arginine | 1.05 | 8.6 |
| | Histidine | 0.47 | 0.7 |
| Hydroxyl | Serine | 12.6 | 9.5 |
| | Threonine | 1.5 | 6.6 |
| | Tyrosine | 10.6 | 6.1 |
| Ring | Proline | 1.5 | 7.2 |
| Double | Cysteine | — | 11.8 |
| Other | Methionine | — | 0.35 |
| | Trytophane | — | 0.7 |

The (water) absorbency of a textile fiber is expressed as a percentage by what is known as moisture regain (MR), i.e., the ability of a fiber to absorb moisture with respect to its dry weight. Values range from hydrophobic fibers, such as glass wool (MR<0.01%) and polyester (MR=0.4%), through hydrophilic fibers such as cotton (MR=7.5%), to rayon (MR=13%) and hygroscopic fibers, such as wool (MR=16%) (see Table 2, below). Certain synthetic fibers with a high degree of hydrophobicity, such as nylons and olefins, also are reported as olephilic, or having a tendency to attract and adsorb oils and fats. The pores within a fabric heavily influence the moisture and air transfer properties of the material. If the collection of human scent is more of a physical interaction with the material than a chemical one, then the MR and the porosity will have an effect on the collection and retention ability of the medium. The porosity of a material is defined as the ratio of airspace to the total volume of the fabric, and is expressed as a percentage as a function of the fabric's density and dimensions;

$$P = \frac{(A \times T - W/D)}{A \times T} \times 100 \quad \text{(Equation I)}$$

where P porosity of the fabric, A=area of the specimen in cm$^2$, T=thickness of the specimen in cm, W=weight of the specimen in g, and D=density of the fiber in g/cm$^3$.

TABLE 2

| SOURCE | FIBER TYPE | ABSORBENCY | STRENGTHS | WEAKNESSES |
|---|---|---|---|---|
| Natural Cellulosic | Cotton | Hydrophilic (MR = 7.5%) | Resists alkali damage High temperature resistance Conducts heat & electricity | Prone to acid damage Susceptible to mildew and mold |
| Natural Cellulosic | Flax | Hydrophilic (MR = 12%) | Resists alkali and organic solvent High absorbency Good conductor of heat | Poor resiliency and stiffness |
| Natural Protein | Wool | Hygroscopic (MR = 16%) | Highly absorbent Resists acid damage | Prone to alkali and heat damage Poor heat conductor Harmed by oxidizing agents |
| Natural Protein | Silk | Hygroscopic (MR = 11%) | Good thermal retention Flame retardant (self extinguishing) Resists mildew and mold | Prone to alkali and heat damage Harmed by oxidizing agents |
| Manufactured Cellulosic | Rayon | Hydrophilic (MR = 13%) | Heat resistant below combustion temperature | Weak Flammable |
| Manufactured Cellulosic | Acetate | Hydrophilic (MR = 6%) | Resistant to ultraviolet Resistant to mildew and mold | Heat sensitive Dissolves in organic solvent |
| Synthetic | Nylon | Hydrophobic (MR = 3.5%) | Strong and lightweight Resists alkali and chlorine bleach Olephilic | Heat sensitive Susceptible to static build-up Flammable Prone to damage |
| Synthetic | Acrylic | Hydrophobic (MR = 1.5%) | Resistant to ultraviolet Resistant to most chemicals Flame retardant (modacrylic) | Susceptible to static build-up Heat sensitive |
| Synthetic | Olefin | Hydrophobic (MR = 0.01%) | Strong and lightweight Inert to most chemicals Olephilic | Very heat sensitive Sensitive to ultraviolet Poor surface texture retention |

TABLE 2-continued

| SOURCE | FIBER TYPE | ABSORBENCY | STRENGTHS | WEAKNESSES |
|---|---|---|---|---|
| Synthetic | Polyester | Hydrophobic (MR = 0.4%) | Excellent resistance to ultraviolet Resistant to most chemicals Olephilic Good wicking | Susceptible to static bulid-up |
| Synthetic | PTFE | Hydrophobic (MR < 0.01%) | Very chemically inert Excellent resistance to ultraviolet Resists high temperature Flame retardant (self extinguishing) | Heavy Low strength Non-stick (Teflon ®) |
| Mineral/ Inorganic | Glass | Hydrophobic (MR < 0.01%) | Strong Flame resistant Resistant to chemicals and ultraviolet | Poor flex abrasion Resistance Skin irritant Heavy |
| Mineral/ Inorganic | Metallic | Hydrophobic (MR < 0.01%) | High electrical conductivity (reduced static build-up) | Poor flex abrasion resistance |

Natural fiber products often require several industrial treatment processes to improve the appearance and quality of the fibers. While the look and finish is important in textile end uses, this use of such fibers in the disclosed methods is for maximized scent collection. The effects of various common textile treatments are described in Table 3, below. One example is mercerization of cotton to improve strength and luster; this process also increases the absorbency of the fiber but changes its surface geometry.

TABLE 3

| FIBER | PROCESS | EFFECT |
|---|---|---|
| Wool | Carbonizing | Acid treatment to remove cellulosic impurities |
|  | Fulling | Washing in soap solution to produce a controlled shrinkage |
| Silk | Degumming | Repeated scouring in soap solution to remove sericin (gummy non-fibrous impurity) |
|  | Weighting | Addition of metallic salt to compensate for weight loss during degumming |
| Cotton | Mercerization | Treatment with NaOH under tension to improve strength, luster and absorbency |
|  | Durable Press | Treatment with a resin solution and curing to develop cross-linkages between cellulose chains |
|  | Acid Finish | Treatment with acid to produce transparent aesthetic effect, at expense of damage to cotton fiber |

Solid Phase Microextraction (SPME)

Solid Phase Microextraction (SPME) has been used for rapid sample preparation in both the laboratory and in the field. This extraction technique is sensitive, selective, and field portable. SPME can be used to sample different mediums, including liquids and gases. There are different types of SPME sampling methods, including a fused-silica extraction. The silica fiber can have various coatings with varying degrees of polarity, or the fiber can have a mixture of phases making it applicable to both polar and non-polar analytes. The amount of analyte extracted from the sample using this technique is partially dependent on the affinity of the analyte for the fiber's coating. SPME utilizes a thin, solid rod composed of fused silica coated with an absorbent polymer. The fiber is protected by a metal sheath, which covers the fiber when it is not in use, and this assembly then is placed in a fiber holder. The SPME extraction technique consists of two processes: analyte partitioning between the sample and the fiber coating, and the concentrated analytes desorbing from the fiber into an analytical instrument. Different types of sorbents extract different types of analytes, and, accordingly, different types of SPME phases have been created. SPME is an equilibrium technique and when a sample is extracted from a sealed vial a three-phase equilibrium exists: (1) the sample to the headspace, (2) the headspace to the fiber, and (3) the fiber to the sample.

The headspace of the sample is described as the phase above the sample. For headspace extraction to occur the sample must be placed in a sealed container, the fiber then is exposed to the gaseous area above the sample for a certain amount of time, retracted, then the analytes can be desorbed from the fiber. The procedure for headspace sampling using SPME is as follows. First, the sample is sealed in a closed container with headspace and equilibrium is established between the sample and the headspace. Next, the SPME fiber is inserted into the headspace of the container, making sure there is no contact between the sample and the fiber. The fiber is exposed inside the container for an amount of time sufficient to allow equilibrium to be reached. The fiber then is retracted and removed from the vial. The fiber then can be inserted into an inlet of an analytical instrument and heated to promote desorption of the analytes. In a heated GC inlet as the temperature increases, the coating/gas partition coefficients decrease and the fiber coating's ability to retain analytes quickly diminishes.

Supercritical Fluid Extraction

When a substance is heated above its critical temperature ($T_c$) and compressed above its critical pressure ($P_c$), a single phase is formed, referred to as a supercritical fluid. At this point, the fluid cannot be liquefied regardless of an increase of pressure. Supercritical fluids portray gas-like diffusivity, low viscosity, and zero surface tension. These unique properties allow supercritical fluids to quickly infiltrate into complex sample matrices thereby providing faster extraction rates. For analytical SFE, the temperatures normally used fall in the 30-150° C. range, which means that the supercritical fluid must be within this range. The best operational extraction parameters for the compounds of interest within a particular sample matrix can be determined by modifying such parameters as pressure, temperature, density, flow rate, and employing the use of modifiers. In contrast to traditional extraction methods, such as Soxhlet and steam distillations, SFE methodology eliminates the use of large quantities of hazardous solvents and the costs for their disposal.

Carbon dioxide ($CO_2$) is the primary fluid used in most SFE applications because it has low critical points ($T_c$=31.3° C., $P_c$=1070 psi), is both non-toxic and non-flammable, and is inexpensive. The drawback to using $CO_2$ is that it is less effective in extracting polar analytes. The addition of a polar solvent, referred to as a modifier, can increase the solvent strength/selectivity of the $CO_2$. Such modifiers include, but are not limited to, methanol, ethanol, propanol, iso-propanol, and water.

Supercritical fluid extraction can be divided into two basic categories: the off-line mode and the on-line mode. The off-line mode refers to running an extraction method where the extracted analytes are collected in a device independent of the measurement instrument. The on-line mode involves the extraction technique, as well as another analytical technique, such as GC/MS. The on-line mode produces a more concentrated extract to the analytical instrument being utilized and gives the sample less interaction with the environment. Analytical SFE has been applied to a range of different industries, including food/flavors, environmental analysis, textile finishing, and pharmaceutical/forensic applications.

Data Treatment

Human odor profiles contain a varying number of compounds depending on the subject being analyzed. Since several variables are being measured within each subject and among the populations, these analyses yield multivariate data. Multivariate data can be used for differentiation between samples where each is characterized by a set of measurements, or in this case subjects, where each subject's odor profile is characterized by a set of volatile compounds. There are several methods available for handling multivariate data, including, but not limited to, principle component analysis (PCA) and the Spearman rank correlation-coefficient. PCA is used to reduce a data set and reveal groups within the data, and has been used in previous studies to determine seasonal differences in VOCs released by people. A correlation value demonstrates the strength of a relationship between two or more variables. Pattern recognition software may also be a viable means for comparing chromatograms of odor profiles.

Principle component analysis (PCA) is a linear combination method used to reduce a complex data set, from the initial n-dimensional space to a few dimensions. PCA is performed with no information on the classification of the samples, and is based solely on the variance of the data set. PCA involves a mathematical procedure that transforms a number of possibly correlated variables into a smaller number of uncorrelated variables called principal components. Principle components are linear combinations of the original variables, which result in the first principal component accounting for as much of the variability in the data as possible, and each following component accounting for as much of the remaining variability as possible. PCA is used to reduce the dimensionality of a data set and to reveal cluster, common traits within the data.

Correlation tests are used to determine relationships between two or more variables. Many correlation determinations require an assumption that the variables have a normal distribution, since that assumption cannot be made in the case of a component of an odor profile nonparametric methods of correlation are required. One of the most used nonparametric methods of measuring correlation is the Spearman rank correlation coefficient. An important concept in nonparametric correlation is assigning an integer value to each variable measured, which is determined by its rank, or size, among the other measurements in the array. One drawback is a potential loss of information in replacing the original numbers with ranks. The Spearman correlation is carried out using the ranked arrays of data, which uses a measure of the linear relationship between two arrays which can be seen from Equation 2, where d is the distance between the ranks and n is the number of variables.

$$r_s = 1 = \frac{6 \sum d^2}{n(n^2 - 1)} \quad \text{(Equation 2)}$$

The resulting correlation coefficient will have a value between −1 and +1. A correlation of −1 or +1 will occur if the relationship between the two arrays is linear, whereas a correlation close to zero means there is no linear relationship between the ranks in the array. A confidence interval then can be calculated to determine the significance of the correlations.

The null hypothesis, which is usually denoted as $H_o$, is the hypothesis which is being tested through the data analysis. In the case of the comparison of odor profiles among a population using the Spearman's rank correlation, the null hypothesis would be that there is not a correlation between the samples and the $H_a$ or alternative hypothesis is that there is a correlation between the samples. The probability of observing a result by chance is usually expressed as a p-value. In any study looking for differences between groups or associations between variables, the likelihood or probability (p) of observing a certain result by chance can be calculated using the t-test. At a 95% confidence level, there is a less than 5% likelihood that the observed difference occurred by chance, or that the null hypothesis will be rejected even though it is true. The rejection of a null hypothesis when it is true is called a Type I error. Type 2 errors can also occur and result from retaining the null hypothesis even when it is false.

Pattern recognition determinations have been applied to chromatographic peak patterns. However, this method may not be the optimal comparison for the peak ratios in human odor. In chromatography, peak shape can vary depending on the amount of analyte traveling through the column. The functionality of an analyte also may alter the shape of a resulting peak. For example, acidic compounds generally do not produce Gaussian shaped peaks because interactions may occur between the analyte and the column.

The methods employed by law enforcement agencies using canines for human scent discriminations have their limits, and the disclosure herein is directed to an alternative and/or additional means of assessing human scent. The creation of an instrumental method for the analysis of the volatile organic compounds present in human scent is applied to the optimization of materials used for the collection and storage of human scent evidence. In addition, a method comparing different techniques for producing analytically clean sorbents for use in human scent collection is disclosed, including: autoclaving, Soxhlet extraction, and supercritical fluid extraction. The persistence of human scent when exposed to the environment, and within a closed system, also was evaluated. Additionally, a comparison of the volatile organic compounds present in human scent collected from the armpit region and palms of an individual allow for determinations as to the types of compounds present in the headspace above secretions produced from different combinations of human secretory glands. A comparison of the compounds present in human odor for an individual over time, and across a population is evaluated allow for the differentiation of individuals based on the volatile organic compounds above collected odor samples.

A viable method for the collection, sampling, separation, and analysis of the volatile organic compounds present in the headspace above collected human odor samples has been developed utilizing sorbent sampling-SPME-GC/MS. Although canines have the ability to detect targets through a high background, this proved to be a limitation for the instrumental analysis of human odor. The use of an optimized supercritical fluid extraction method as a pre-treatment for the collection material produces an analytically clean medium and, thus, allows for the consideration of human compounds that previously would be excluded due to their background presence, such as decanal and nonanal. The existence of previously reported odor components on collection mediums, as well as those contributed to samples by storage materials, was removed through a pre-treatment of the sorbent materials and glass containment.

Previously, technological limitations have restricted the ability of researchers to identify the chemical components that comprise human odor or to use the information to chemically distinguish between individuals. Odor profiles collected from the same region of the body among individuals can be evaluated through comparison of the relative ratios of the odor compounds extracted. It has been shown to be possible to distinguish between the individuals studied here using the relative ratio comparisons of common compounds extracted among individuals. However, examination of additional compounds provides greater discrimination ability. Using this semi-quantitative method of analysis, it also is possible to establish that multiple samplings of one individual over time do not contain as much variation as that throughout a population. These results support the individual odor theory that has previously been demonstrated by the ability of canines to accurately discriminate between individuals based on their odor.

The evaluation of the odors released from collected armpit secretions across a ten subject population has allowed for determinations to be made about the abundances of components of human scent collected from the armpit. The seven different types of compounds determined to be present in a human armpit odor profile included acids, alcohols, aldehydes, alkanes, esters, ketones, and nitrogen containing compounds. Across the ten subjects and sixty-five human compounds extracted, there was a high degree of variability observed with fifteen high frequency compounds, nineteen medium frequency compounds, and thirty-one low frequency compounds among the population.

The evaluation of the odors released from collected hand secretions across a sixty subject population has allowed for determinations to be made about the abundances of components of human scent collected from the hands. The seven different types of compounds determined to be present in a human hand odor profile included acids, alcohols, aldehydes, alkanes, esters, ketones, and nitrogen containing compounds. Across the sixty subjects and sixty-three human compounds extracted, there was a sufficient degree of variability observed with six high frequency compounds, seven medium frequency compounds, and fifty low frequency compounds to allow all subjects in the population to be differentiated.

Additional aspects and details of the disclosure will be apparent from the following examples, which are intended to be illustrative rather than limiting.

EXAMPLES

Absorber Materials

The ten different brands of absorbers used in this study include: CFF Super Absorber Cotton Roll, DUKAL brand, 100% cotton, sterile, 2×2, 8 ply, gauze sponges (DUKAL Corporation, Syosset, N.Y.), Johnson & Johnson sterile small pads 2×2 in. and 5×9 in. sterile dressing (Johnson & Johnson Consumer Company, Inc, Skillman, N.J.), Eckerd Sterile Pads (Eckerd Drug Company, Clearwater, Fla.), IMCO sterile gauze sponges, 2×2 in. (Independent Medical Co-op, Inc. Daytona Beach, Fla.), Nexcare Sterile Pads (3M Health Care, St. Paul, Minn.), Kings Cotton, Hungarian Adsorbers, and Polish absorbers (Dutch National Police); glass beads (3 mm) Spherical Soda Lime, Solid Glass Beads (Fisher Scientific, Pittsburgh, Pa., USA), and Microscope Glass Slides (Fisher Scientific, Pittsburgh, Pa., USA).

Cleansers

The twenty-five different types of cleanser used in this study include: Dove unscented moisturizing soap (Unilever, Greenwich, Conn.), Dove unscented moisturizing body wash (Unilever, Greenwich, Conn.), Natural, Clear Olive Oil Soap from Life of the Party (North Brunswick, N.J., USA), Natural, Avocado and Cucumber Soap from Life of the Party (North Brunswick, N.J., USA), Dial Pure and Natural, Hypoallergenic bar soap (Dial Corporation, Scottsdale, Ariz., USA), Imperial Leather, fresh shower gel (Cussons, Stockport, England), Softsoap Gel, hand soap, antibacterial with moisturizers (Colgate Palmolive, N.Y., USA), Olay Beauty Bar, sensitive skin (Proctor & Gamble, Cincinnati, Ohio, USA), Irish Spring, original deodorant soap (Colgate Palmolive N.Y., USA), Irish Spring deodorant soap "Icy Blast" (Colgate Palmolive, N.Y., USA), Irish Spring Micro-clean hand soap (Colgate Palmolive N.Y., USA), Aveeno, positively radiant cleanser (Johnson & Johnson, Skillman N.J., USA), Vive for Men, Double Action Face Wash (BDF, Wilton, Conn., USA), Softsoap Naturals, moisturizing body wash milk and lavender (Colgate Palmolive, N.Y., USA), Softsoap hand soap, antibacterial, clear with light moisturizers (Colgate Palmolive, N.Y., USA), Ultra Palmolive Antibacterial, hand soap, with Orange Extracts, (Colgate Palmolive N.Y., USA), Equate Antibacterial Clear Liquid Soap gentle+mild w/light moisturizers (Vi-Jon Laboratories, Inc. St. Louis, USA), Betres Oatmeal Sensitive Skin (Healthtex Distributors Inc, Miami, Fla., USA), Betres Loofah Exfoliant Soap (Realthtex Distributors Inc. Miami, Fla., USA), Passion Fruit Organic Soap (Country Rose Soap, Canada), Lavender+Lime Organic Soap (Country Rose Soap, Canada), Emu Oil Soap (Country Rose Soap, Canada), Lemon Orchard Organic (Country Rose Soap, Canada), Liquid Castille Olive Oil Soap (Country Rose Soap, Canada), and Cristallino Olor a Fresa con Cremogen y Glicerina (Hada s.a. Manizales, Colombia).

Storage Materials

Storage materials used in the examples outlined below include: Ziploc, Freezer Guard Seal, Pint Size, 7.0"×5.25", (SC Johnson & Sons Inc., Racine, Wis., USA). Kapak Heavy Duty SealPAK Pouches, PET//LLDPE, 4.5 mils thick, 6.5"×8" (Kapak Corporation, Minneapolis, Minn., USA). Kapak Aluminized Pouches, tri-layer polymer chemistry featuring an aluminum film, 6.5"×8", Job# J9539, Lane#2, Box#056 (Kapak Corporation, Minneapolis, Minn., USA). Polyethylene Pouches, 3"×3", 2 mil thick, Item#01-0303-2 (Veripak, Atlanta, Ga., USA). The vials used in this study were 10 mL glass, clear, screw top vials with PTFE/Silicone septa (SUPELCO, Bellefonte, Pa., USA).

Laboratory Materials

SPME fibers used included Carbowax/Divinylbenzene (orange), Polydimethylsiloxane (red), Polydimethylsiloxane/divinylbenzene (blue), Carboxen/Polydimethylsiloxane (black), and Divinylbenzene/Carboxen on Polydimethylsiloxane (DVB/CAR on PDMS) (grey) 50/30 μm fibers (SUPELCO, Bellefonte, Pa., USA). Steel paint cans, quart size, All American Containers (Miami, Fla., USA), Activated Charcoal Strips (ACS), Diffusive Flammable Liquid Extraction (DFLEX, Cromwell, Conn., USA), Stopper Sleeve, 11 mm, natural red rubber, Lot #1085967-01, Case #075 (Wheaton, Millville, N.J., USA). The extraction solvent for the pre-treatment of the gauze pads by supercritical fluid extraction was supercritical grade carbon dioxide (Air Products, Allentown, Pa., USA). The methanol used as the modifier for the pre-treatment of the gauze pads was HPLC grade (Fisher Scientific, Pittsburgh, Pa., USA).

Instrumental Methods

The instrumentation used for the separation and analysis of the analytes was an Agilent 6970 GC/5973 MSD. The column used was a HP5-MS, 30 meter, 0.25 μm, 0.25 mm with helium as the carrier gas (flow rate: 1.0 mL/min). The general volatiles method for the GC/MS began when analytes were desorbed in the injection port of the GC with an inlet temperature of 250° C. The GC method begins with an initial oven temperature of 40° C. for 5 min, then ramped at 10° C./min until the temperature reaches 300° C., and held at 300° C. for 2 min. (total run time: 33 min.). The mass spectrometer used was an HP 5973 MSD with a quadrupole analyzer in full scan mode (range: 50-550 Da). The equipment used was an ISCO Model 260D Syringe Pump with an SFX 2-10 Extractor. The Scanning Electron Microscope (SEM) used was a JEOL JSM 5900LV from and the Field Emission Scanning Electron Microscope used was a JOEL JSM-6330F.

Comparison of ACS and SPME for the Extraction of Human Scent

Scent from socks that had been worn by Male 1 for nine hours was analyzed. Six socks from three consecutive days were each sealed in a quart sized paint can which had been modified with a rubber septum in the lid of the can, to allow for SPME extraction. Three of the socks were analyzed through ACS-GC/MS and three through SPME-GC/MS. The ACS and SPME extractions were both done for 15 hours, then analyzed. The ACS strips were eluted by soaking the strip in 100 μL of methylene chloride for 30 minutes followed by centrifugation. A DVB/Carboxen on PDMS StableFlex fiber was used for the SPME extraction because it extracts both polar and non-polar compounds. Prior to use in this experiment, each sock was analyzed using the same method for background purposes. The GC/MS method used was as described above.

Comparisons of ACS extraction and SPME show that SPME is more sensitive and preferred extraction technique for the analysis of human scent. SPME was able to extract a larger number of compounds and in higher quantities than ACS, as seen in Table 4. Due to high background and the large size of the socks, a smaller less compound heavy collection material would be more effective for use as a collection medium.

TABLE 4

| Human Compounds Extracted | Sampling Method | | | | | |
|---|---|---|---|---|---|---|
| | ACS S1 | ACS S2 | ACS S3 | SPME S1 | SPME S2 | SPME S3 |
| 1,3,5,7-Cyclooctatetraene | | | | | X | |
| 1,6-Octadien-3-ol, 3,7-dimethyl- | | | | X | | |
| 1-Pentadecene | | | | X | | X |
| 2-Decanone | | | | | | X |
| 2-Hexanone | | | | | | X |
| 4-Heptanone | | | | | | X |
| 5,9-Undecadien-2-one, 6,10-dimethyl- | | | | X | X | X |
| 6-methyl-5-hepten-2-one | X | X | X | | | |
| Acetic acid, phenylmethyl ester | | | | | X | |
| Acetophenone | | | | X | X | X |
| Benzene, 1,2,4-trimethyl- | | | | | X | |
| Benzene, 1-methyl-2-(1-methylethyl)- | | | | | | X |
| Disulfide, dimethyl | | | | X | | X |
| Eicosane | | | | X | X | X |
| Heneicosane | X | | X | | | |
| Naphthalene | | | | X | | |
| Phenol | | | | X | X | X |
| Pyrazine | | | | | | X |

TABLE 4-continued

| Human Compounds Extracted | Sampling Method | | | | | |
|---|---|---|---|---|---|---|
| | ACS S1 | ACS S2 | ACS S3 | SPME S1 | SPME S2 | SPME S3 |
| Pyrazine, trimethyl- | X | | | | | |
| Trisulfide, dimethyl | | | X | X | | X |
| Total Number of Other Compounds Extracted | 8 | 8 | 10 | 25 | 32 | 30 |

Solid Phase Microextraction (SPME) Optimization

The fibers evaluated were: carbowax/divinylbenzene (alcohols and polar compounds), polydimethylsiloxane (nonpolar, semi-volatiles), polydimethylsiloxane/divinylbenzene (volatiles, amines, nitroaromatics), carboxen/polydimethylsiloxane (gases, low molecular weight), and divinylbenzene/carboxen on polydimethylsiloxane (flavors, volatiles, semi-volatiles).

Male 1 wore five pieces of DUKAL gauze between the foot and sock for ten hours. Each piece of gauze then was placed into a vial and extracted overnight using the orange (Carbowax/Divinylbenzene) (CW/DVB), red (Polydimethylsiloxane) (PDMS), blue (Polydimethylsiloxane/divinylbenzene) (PDMS/DVB), black (Carboxen/Polydimethylsiloxane) (CAR/PDMS), or grey (Divinylbenzene/Carboxen on Polydimethylsiloxane) (DVB/CAR/PDMS) fibers. Each fiber was exposed to the gauze sample for 15 hours. The fiber then was analyzed using the GC/MS method as described above.

Table 5 displays the human compounds extracted in the headspace of the scented gauze using the different fiber chemistries of DVB/CAR/PDMS, CAR/PDMS, and PDMS/DVB. Table 5 does not list PDMS or CW/DVB because they did not extract any human compounds from the headspace. The two preferred fiber types are CAR/PDMS and DVB/CAR/PDMS, which extracted two and seven previously reported human compounds, respectively.

TABLE 5

| Human Compounds | Fiber Type | | |
|---|---|---|---|
| | DVB/CAR/PDMS | CAR/PDMS | PDMS/DVB |
| 1,6-octadien-3-ol, 3,7-dimethyl | X | | |
| 2,5-cyclohexadiene-1,4-dione, 2,6-bis(1,1-dimethyl) | X | X | |
| Acetophenone | X | | |
| Eicosane | | | X |
| Heptadecane | X | | |
| Hexanoic acid, 2-ethyl- | X | X | |
| Pentanoic acid | X | | |
| Tetradecane | X | | |

Evaluation of Different Absorbent Collection Mediums:

Ten different brands of absorbers used in this study include: CKF Super Absorber Cotton Roll, DUKAL brand, 100% cotton, sterile, 2×2, 8 ply, gauze sponges (DUKAL Corporation, Syosset, N.Y.) Johnson & Johnson sterile small pads 2×2 in and 5×9 in. sterile dressing (Johnson&Johnson Consumer Company, Inc, Skillman, N.J.), Eckerd sterile pads, 2×2 in. (Eckerd Drug Company, Clearwater, Fla.), IMCO sterile gauze sponges, 2×2 in (Independent Medical Co-op, Inc. Daytona Beach, Fla.), Nexcare sterile pads, 2×2 in. (3M Health Care, St. Paul, Minn.), Kings Cotton, Hungarian Adsorbers, and Polish absorbers (Dutch National Police) were assessed for ability to collect human scent samples.

Headspace Analysis Method: To assess the amount and type of background compounds in each absorbent material, each type of absorber was placed into a 10-mL glass, clear, screw top vial with PTFE/Silicone septa (SUPELCO, Bellefonte, Pa., USA). Divinylbenzene/Carboxen on Polydimethylsiloxane (DVB/CAR on PDMS) 50/30 μm fibers (SUPELCO, Bellefonte, Pa., USA) were used to extract the compounds present in the headspace above the absorbers contained within the vials. The extractions were performed for 15 hrs, as previously determined to be a sufficient extraction time for evaluating collected armpit odor samples. The GC/MS method used for the separation and analysis was as described above.

Each absorber evaluated showed the presence of headspace compounds regardless of its sterility. DUKAL brand gauze pads extracted the least amount of compounds, whereas Nexcare absorbers extracted the greatest number of compounds. The compounds extracted among the ten brands of absorber studied are listed in Table 6 and the average number of compounds extracted in the headspace of the absorbers studied is in Table 7.

TABLE 6

| | Nexcare Gauze | Eckerd Gauze | CKF SuperAbsorber | J & J 2 × 2 | J & J 5 × 7 | DUKAL Gauze | IMCO 2 × 2 | King's Cotton | Hungarian Cotton | Polish Absorber |
|---|---|---|---|---|---|---|---|---|---|---|
| Initially Sterile (Yes/No) | Y | Y | N | Y | Y | Y | Y | N | N | N |
| (+)-α-terpineol | | | X | | | | | | | |
| (E)-2-decenal | | | | | | | | | X | |
| (E)-2-heptenal | | | | X | | | | | | |
| (E)-2-nonenal | | | | | | | | X | | |
| (Z)-7-tetradecene | | | | X | | | | | | |
| α Isomethyl ionone | | X | | | | | | | | |
| [(dodecyloxy)methyl]-oxirane | | | X | | | | | | | |

TABLE 6-continued

| | Nexcare Gauze | Eckerd Gauze | CKF SuperAbsorber | J & J 2 × 2 | J & J 5 × 7 | DUKAL Gauze | IMCO 2 × 2 | King's Cotton | Hungarian Cotton | Polish Absorber |
|---|---|---|---|---|---|---|---|---|---|---|
| 2-methyl propanoic acid | | | | X | | X | | | | |
| 1,1,4,4,7,7-hexamethyl-cyclononane | | X | | | | | | | | |
| 1,1-dodecanediol, diacetate | | | | | | | | | | X |
| 1,2,3-trimethyl benzene | | | | | | X | | | | X |
| 1,2,4,5-tetramethyl benzene | X | | | | | | | | | |
| 1,2,4-Methenoazulene, decahydro-1, | | | | | | | X | | | |
| 1,2,4-trimethyl benzene | X | | | | | X | | | | |
| 1,2-dichloro benzene | X | | | | | | | | | |
| 1,3,5-trimethyl benzene | X | | | | X | | X | | | X |
| 1,3-dimethyl benzene | X | | | | | X | | | | |
| 1,4-dichloro benzene | | | | | X | X | | | | |
| 1,5,4-dibromo tetrapentacontane | | | | | | | | | | X |
| 1,7,11-trimethyl cyclotetradecane | | X | | | | | X | | | |
| 10-methylnonadecane | X | | | | | | X | | | |
| 13,17,21-trimethylheptatriacontane | | | | | | | | | X | |
| 17-pentatriacontene | X | | | | | | | | | |
| 1-chloro heptacosane | | | | | X | | | | | X |
| 1-dodecene | X | | | | | | | | | |
| 1-ethyl-2,3-dimethyl benzene | X | | | | | | | | | |
| 1-heptadecene | | | | | | | X | | | X |
| 1-methyl-2-(1-methylethyl) benzene | X | | | | | | | | | |
| 1-methyl-2-pyrrolidinone | | | | | | | | | | X |
| 1-methyl-4-(1-methylethyl) benzene | X | | | | | | | | | |
| 1-methyldecahydronaphthalene | | | X | | | | | | | |
| 1-nonene | | | | | | | | X | | X |
| 1-octadecene | | | | | | | | | | X |
| 1-octanol | | | | | | | X | | X | |
| 1-pentadecene | | | | X | | | X | | X | X |
| 1-pentyl-2-propyl cyclopentane | X | | X | | | | | | | |
| 1-propylpentachlorotriphosphazene | | | | | | | X | | | |
| 1-tetradecene | X | X | X | X | | | | | | |
| 2-(2-methoxyethoxy) ethanol | | | | | | | | | X | |
| 2(3H)-Furanone, dihydro-5-methyl- | | | | | | | X | | | |
| 2-(dodecyloxy) ethanol | X | | | | | | | | | |
| 2,2,4-trimethyl-pentanoic acid | | X | | | | | | | | X |
| 2,2'-diethyl-1,1'-biphenyl | | | | | | X | X | | | X |
| 2,4-bis(1,1-dimethylethyl) phenol | | | | | | | | | X | |
| 2,5-cyclohexadiene-1,4-dione | | | X | | | | | | | X |
| 2,6-cyclohexadiene-1,4-dione | X | X | X | X | X | | X | X | X | X |
| 2,6,10,14-tetramethyl hexadecane | | X | | | | X | X | X | X | X |
| 2,6,10,14-tetramethyl pentadecane | | X | | | | X | X | X | X | X |
| 2,6,10-trimethyl dodecane | | | X | | | X | X | | | |
| 2,6,10-trimethyl pentadecane | | X | | X | | | | | X | X |
| 2,6,10-trimethyl tetradecane | | | | | | | | | | X |
| 2,6,11,15-tetramethyl hexadecane | X | | | | | | | | | |
| 2,6,11-trimethyl dodecane | X | | | | X | | | | | |
| 2,6-bis(1,1-dimethylethyl) phenol | | X | | | | | X | | | |
| 2,6-bis-cyclohexadien-1-one | | X | | | | | | | | |
| 2,6-diisopropylnaphthalene | | | X | | | | | X | X | X |
| 2,6-dimethyl heptadecane | X | | | | | | | | | |
| 2,6-dimethyl undecane | X | | | | | | | | | |
| 2,6-dimethyl-7-octen-2-ol | X | X | | X | | | | | | |
| 2,9-dimethyl undecane | X | | | | | | | | | |
| 2-butoxy ethanol | X | X | X | X | X | X | X | X | X | X |
| 2-dodecen-1-yl(−) succinic anhydride | | | | | | | | | | X |
| 2-ethenyl-1,4-dimethyl benzene | X | | | | | | | | | |
| 2-ethyl-1-hexanol | X | | X | X | X | X | X | | X | X |
| 2-ethyl-2-methyl propanoic acid | | | | | | | | | X | |
| 2-Furanmethanol | | | | | | | X | | | |
| 2-hydroxy benzaldehyde | X | | | | | | | X | | |
| 2-methyl decane | | | X | | | | | | | |
| 2-methyl tricosane | | | X | | | | | | | |
| 2-n-butylacrolein | | | | | X | | | | | |
| 2-pentadecanol | | | | | | | | | X | |
| 2-Propanol, 1-(2-methoxypropoxy)- | | | | | | | X | | | |
| 2-propoxy ethanol | | | | | | | | | | X |
| 2-Pyridinecarboxaldehyde | | | | | | | X | | | |
| 3,5,24-trimethyl tetracontane | X | | X | | | | | | | |
| 3,5,3',5'-tetramethylbiphenyl | | | | | | | | | X | |
| 3,7-dimethyl-1,6-octadien-3-ol | | X | | X | | | | | | |
| 3-cyclohexene-1-methanol, .alpha. | | X | | X | | | | | | |
| 3-heptanone | | | | | X | | | | | |
| 3-methyl decane | | | X | | | | | | | |
| 3-methyl pentadecane | | | | | | | | | | X |
| 3-methyl tridecane | | | X | | | | | | | |
| 3-methyl undecane | X | | | | | | | | | |

TABLE 6-continued

| | Nexcare Gauze | Eckerd Gauze | CKF SuperAbsorber | J & J 2 × 2 | J & J 5 × 7 | DUKAL Gauze | IMCO 2 × 2 | King's Cotton | Hungarian Cotton | Polish Absorber |
|---|---|---|---|---|---|---|---|---|---|---|
| 3-methyl-5-(1-methylethyl) phenol | X | | | | | X | | | | |
| 3-Penten-2-one, 4-methyl- | | | | | | | | | | |
| 3-phenoxy-1-propanol | | X | | | | | | | | X |
| 4-cyanocyclohexene | | | | | | | | X | | X |
| 4-cyclohexyl dodecane | | | | X | | | | | | |
| 4-cyclohexyl tridecane | | X | | | | | | | | |
| 4-ethyl-1,2-dimethyl benzene | X | | | | | | | | | |
| 4-methyl decane | | | X | | | | | | | |
| 4-methylcarbazole | | | | X | | | | | | |
| 5-methyl-2-(1-methyl) cyclohexanone | X | X | X | X | | | | | | |
| 5-methyl-2-(1-methyl) cyclohexanol | X | | X | X | | | X | | | |
| 5-propyl tridecane | | | | | | | | | X | |
| 6,10-dimethyl-5,9-undecadien-2-one | | | | | | | | X | | X |
| 6-Tridecene | | | | | | | X | | | |
| 9-octyl heptadecane | | | | | | | | | X | |
| acetic acid, phenylmethyl ester | X | X | | | | | | | | |
| acetophenone | X | X | | | | | X | | | X |
| benzaldehyde | | X | | X | | | | | | |
| Benzene, (1-butylheptyl)- | | | | | | X | | | | |
| Benzene, (1-butylhexyl)- | | | | | | X | | | | |
| Benzene, (1-butyloctyl)- | | | | | | X | | | | |
| Benzene, (1-ethyldecyl)- | | | | | | X | | | | |
| Benzene, (1-pentylheptyl)- | | | | | | X | | | | |
| Benzene, (1-propylnonyl)- | | | | | | X | | | | |
| Benzene, 1,3,5-tris(1-methylethyl) | | | | | | | X | | | |
| Benzene, 1,3-bis(1,1-dimethylethyl) | | | | | | | X | | | |
| benzophenone | | | | X | | | | | | |
| benzyl alcohol | X | | | | | | | X | X | |
| Butanoic acid, butyl ester | | | | | | X | | | | |
| Butylated Hydroxytoluene | | | | | | X | X | | | |
| camphor | X | | | X | | | | | | |
| caprolactam | | | | | X | | | | | |
| cis-2,6-dimethyl-2,6-octadiene | | | | X | | | | | | |
| cyclododecane | X | | | | | | | | | |
| Cyclohexadecane | | | | | | | X | | | |
| Cyclohexane, 1-(1,5-dimethylhexyl) | | | | | | | X | | | |
| Cyclopentadecane | | | | | | | X | | | |
| cyclotetradecane | X | | | X | | | | | | |
| decanal | X | | | X | X | X | X | X | X | X |
| decane | X | | X | X | | | | | | |
| Decane 3-cyclohexyl-, 3-cyclohexyl | | | | | | | X | | | |
| diisopropylnaphthalene | | | | | | | | X | | |
| dimethyl phthalate | | | | | | | | X | | |
| D-Limonene | X | | | X | | | | | | |
| docosane | | | | | | | | | X | |
| dodecane | X | | | X | | | X | | X | |
| dotriacontane | | X | | | | | | | | |
| eicosane | X | X | | | | X | X | | X | |
| furfural | | | | X | X | | | | | |
| heptadecane | X | X | | X | X | X | X | X | X | X |
| Heptadecane, 3-methyl- | | | | | | | X | | | |
| Tridecane, 7-hexyl- | | | | | | | X | | | |
| tritetracontane | | X | X | | | | X | | | X |
| undecanal | | | | | | X | | X | X | X |
| undecane | | | X | | X | | | | X | |

TABLE 7

| Gauze Brand | Sterile | Size (cm) | Ave. Number of Compounds |
|---|---|---|---|
| Dukal | Yes | 5.1 × 5.1 | 12 |
| J&J | Yes | 5.1 × 5.1 | 17 |
| J&J (STU-100) | Yes | 12.7 × 22.9 | 43 |
| Nexcare | Yes | 5.1 × 5.1 | 58 |
| IMCO | Yes | 5.1 × 5.1 | 45 |
| Eckerds | Yes | 5.1 × 5.1 | 19 |
| Cotton Roll | No | N/A | 38 |
| King's Cotton | No | 5.1 × 5.1 | 22 |
| Polish Absorbers | No | 5.1 × 5.1 | 35 |
| Hungarian Cotton | No | 5.1 × 5.1 | 29 |

The most common compounds detected in the samples were decanal, heptadecane, cyclotetradecane, hexadecane, phenol, nonadecane, 2-ethyl-hexanoic acid, benzyl alcohol, and 2-butoxy-ethanol. The absorbent materials which generally contain lower amount of headspace compounds were previously sterilized by the manufacturers. The sterilization process performed by the manufacturers typically is a gravity or steam autoclaving process, which produces a biologically clean material. However, as shown by these results, biologically clean does not equate to analytically clean, which is preferable when instrumentally analyzing human scent. Many of the compounds extracted in the headspace of these absorbers have been previously reported as components of human secretions, and thus the initial presence of these compounds in the material is a serious limitation for the use of these materials as collection mediums of human scent for analysis. In order for these absorbers to be used as collection materials for the instrumental evaluation of human scent additional sterilization processes are necessary.

Scanning Electron Microscope (SEM) and Field Emission Scanning Electron Microscope (FESEM) Imaging of Surface Characteristics of Absorbers DUKAL, Johnson & Johnson (both 2×2 and STU-100), Polish absorber, Hungarian absorber, and King's Cotton absorbers were cut into a small piece of material. The small pieces then were placed onto an aluminum stub with carbon adhesive. For SEM imaging, the mounted samples were placed into a SPI MODULE Sputter Coater, and the gauzes then were coated with gold-palladium. The JOEL JSM-5910LV SEM then was used to image each piece of material at 25× magnification. For FESEM imaging, the mounted samples were placed into a PELCO SC-7 Auto Sputter and coated with gold. The JOEL JSM-6330F FESEM then was used to image each piece of material at 500× and 2000× magnification.

Table 8 lists the fiber composition and initial sterilization methods used prior to distribution for each of the absorbers evaluated. Each absorber has different surface characteristics. Various weaving techniques produce differing pore sizes, which can affect its ability to collect and retain human scent. The hypothesis that human scent is deposited into the environment through rafts carrying skin cells suggests that the pore size of a collection material may prove to be a limiting factor in effective human scent collection and retention over time.

TABLE 8

| BRAND NAME | TEXTILE MATERIAL | INITIAL STERILIZATION METHOD |
|---|---|---|
| Dukal | 100% Cotton | Gamma Radiation |
| Eckerd | 70% Rayon, 30% polyester-cotton mix | Ethylene Oxide |
| Nexcare | Polypropylene/wood fiber | Ethylene Oxide |
| Johnson & Johnson | Rayon/polyester/cellulose | Autoclave/Gamma Radiation |
| King's Cotton | 100% Cotton | None |

Analysis of Body Odor Collected from Individuals

Comparison of Foot Odor Among Individuals: All gauze used in this study was DUKAL brand, 100% cotton, sterile, 2×2, 8 ply, gauze sponges (DUKAL Corporation, Syosset, N.Y.). The sterile gauze was not subjected to any additional sterilization processes. The vials used in this study were 10 mL glass, clear, screw top vials with PTFE/Silicone septa (SUPELCO, Bellefonte, Pa., USA). Prior to use, the glass vials and septa were rinsed with acetone and baked at 210° C. for 48 hrs to remove volatile compounds present initially in the vials.

The sterile gauze was sealed in 10 mL glass vials, extracted, and analyzed to determine which compounds were present initially on the gauze. These compounds were noted prior to use for background purposes. Five subjects, three females and two males (F1, F2, F3, M2, and M3), wore a piece of DUKAL gauze between their foot and their sock for a period of 9 hrs. The gauze then was removed by the subject, and returned to the 10 mL glass vial.

The collected body region samples were allowed to sit in the glass vial for 24 hrs, then extracted using SPME. DVB/Carboxen on PDMS 50/30 um fibers (Supelco, Bellefonte, Pa., USA) were used to extract the volatile organic compounds from the headspace of the vials containing the gauze. The exposure was performed at room temperature for 15 hours.

The headspace extraction of foot odor collected from the five subjects (F1, F2, F3, M2, and M3) is summarized in Table 9. Napthalene was extracted in all of the subjects studied, while 3,7-dimethyl-1,6-octadien-3-ol, 6-methyl-5-hepten-2-one, acetic acid-phenylmethyl ester, acetophenone, octanoic acid, phenol, and phenylethyl alcohol were seen in four of the subjects. Eicosane was extracted in three of the individuals, while 1-hexadecene, 1-pentadecene, 1-tetradecene, (E)-2-decenal, and 6,10-dimethyl-5,9-undecadien-2-one, dodecanoic acid-ethyl ester each were extracted in only one of the subjects. This method places the collection material under the influence of not only the foot sweat, but also the contributions from socks and shoes. Due to the possibility that these compounds are present due to outside sources, sampling foot odor through this method is not a preferred method of human odor detection.

TABLE 9

| Human Compounds | F1 | F2 | F3 | M2 | M3 |
|---|---|---|---|---|---|
| 1,6-Octadien-3-ol, 3,7-dimethyl- | X | X | X | X | |
| 1-Hexadecene | | X | | | |
| 1-Pentadecene | | X | | | |
| 1-Tetradecene | | | | X | |
| 2,6-Octadien-1-ol, 3,7-dimethyl- | | | X | | |
| 2-Decenal, (E)- | | | X | | |
| 5,9-Undecadien-2-one, 6,10-dimethyl- | | | | | X |
| 5-Hepten-2-one, 6-methyl- | X | | X | X | X |
| Acetic acid-phenylmethyl ester | | X | X | X | X |
| Acetophenone | | X | X | X | X |
| Dodecanoic acid-ethyl ester | | | X | | |
| Eicosane | X | | | X | X |
| Naphthalene | X | X | X | X | X |
| Octanal | | X | | | |
| Octanoic acid | | X | X | X | X |
| Phenol | | X | X | X | X |
| Phenylethyl alcohol | | X | X | X | X |
| Total Number of Other Compounds Extracted | 26 | 33 | 36 | 41 | 17 |

Comparison of Odor Collected from Different Body Regions

All gauze used in this study was DUKAL brand, 100% cotton, sterile, 2×2, 8 ply, gauze sponges (DUKAL Corporation, Syosset, N.Y.). The sterile gauze was not subjected to any additional sterilization processes. The vials used in this study were 10 mL glass, clear, screw top vials with PTFE/Silicone septa (SUPELCO, Bellefonte, Pa., USA). Prior to use, the glass vials and septa were rinsed with acetone and baked at 210° C. for 48 hrs to remove volatile compounds present initially in the vials.

Body Region Sampling: The sterile gauze and corresponding safety pin were sealed into a 10 mL glass vial, extracted, and analyzed to determine which compounds were present initially on the gauze. These compounds were noted prior to use for background purposes. Six pieces of gauze were placed in six different regions of the body of Female 3, i.e., behind the knee, bottom of the foot, the armpit, the wrist, the crook of the elbow, and the side of the waist. All pieces of gauze, except the gauze in the sock, were attached to the clothing of Female 3 using safety pins. The gauze which sampled odor obtained from the bottom of the foot was placed between the pad of the foot and the subject's sock. The gauzes were worn for 9 hrs, then removed by the subject and placed back into the original 10 mL glass vials along with the corresponding safety pins.

Analyses: The collected body region samples were allowed to sit for 24 hrs, then extracted using SPME. DVB/Carboxen on PDMS 50/30 um fibers (Supelco, Bellefonte, Pa., USA) was used to extract the volatile organic compounds from the headspace of the vials containing the gauze. The exposure was performed at room temperature for 15 hours.

The six different regions of the body produced chromatograms which are similar, but not identical. This was expected due to concentration and distribution differences of secretion glands across the body. For example, armpit odor is a combination of apocrine, eccrine, and sebaceous gland secretions, whereas hand and foot odor is only a combination of secretions from the eccrine and sebaceous glands.

Table 10 lists the human compounds extracted from the six different body regions of Female 3. The gauze placed in contact with the bottom of the foot extracted thirteen human compounds, the armpit produced twelve, the wrist produced ten, the elbow and waist both resulted in seven human compounds, and the knee only produced three human compounds. A total of nineteen human compounds were extracted among the different body regions of Female 3. However only three of these compounds were present in all of the regions sampled: 3,7-dimethyl-1,6-octadien-3-ol, 3,7-dimethyl-6-octen-1-ol, and octadecane. There were no compounds extracted in five of the six body regions. However, 6-methyl-5-hepten-2-one, acetic acid-phenylmethyl ester, and cedrol were extracted in four of the six regions sampled. Eicosane and 1-pentadecene each were extracted in three of the body regions studied. Although the gauze and the safety pins were analyzed prior to use for background purposes, the influences of clothing and shoes on the chromatograms was not assessed.

TABLE 10

| Human Compounds Extracted | Sock | Armpit | Wrist | Elbow | Waist | Knee |
|---|---|---|---|---|---|---|
| 1,6-Octadien-3-ol, 3,7-dimethyl- | X | X | X | X | X | X |
| 1-Pentadecene | X | X | | | X | |
| 2-Furancarboxaldehyde | | | X | | | |
| 5,9-Undecadien-2-one, 6,10-dimethyl- | | X | | | | |
| 5-Hepten-2-one, 6-methyl- | X | X | X | | X | |
| 6-Octen-1-ol, 3,7-dimethyl- | X | X | X | X | X | X |
| Acetic acid-phenylmethyl ester | X | X | X | | X | |
| Acetophenone | | X | | | | |
| Benzene, 1,3,5-trimethyl- | | | X | X | | |
| Cedrol | X | X | X | X | X | |
| Dodecane | X | X | | | | |
| Dodecanoic acid | X | | | | | |
| Eicosane | | X | X | X | | |
| Heneicosane | | X | | | | |
| Heptanal | X | | | | | |
| Octadecane | X | X | X | X | X | X |
| Pentadecane | X | | | | X | |
| Phenylethyl Alcohol | X | X | | | | |
| Thiazolidine | | | | X | | |

Comparison of Armpit Odor Collected from the Right and Left Side of an Individual: All gauze used in this study was DUKAL brand, 100% cotton, sterile, 2×2, 8 ply, gauze sponges (DUKAL Corporation, Syosset, N.Y.). The sterile gauze was not subjected to any additional sterilization processes. The unscented soap used in this study was Dove unscented moisturizing soap (Unilever, Greenwich, Conn.). The vials used in this study were 10 mL glass, clear, screw top vials with PTFE/Silicone septa (SUPELCO, Bellefonte, Pa., USA). Prior to use, the glass vials and septa were rinsed with acetone and baked at 210° C. for 48 hrs to remove volatile compounds present initially in the vials.

The sterile gauze and corresponding safety pin were sealed into a 10 mL glass vial, extracted, and analyzed to determine which compounds were present initially on the gauze. These compounds were noted prior to use for background purposes. Male 4 was required to use fragrance free soap and to discontinue the use of deodorant, lotions, and perfumes for 48 hours before sampling to minimize the influence of the "tertiary odors." A piece of gauze was fastened with a safety pin to the left and right armpit area of Male 4's shirt and worn for 9 hrs. After the sampling time was complete, the gauze was removed by the subject and placed back into the original 10 mL glass vials.

The collected armpit samples were allowed to sit for 24 hrs, then extracted using SPME. DVB/CAR/PDMS 50/30 µm fibers (Supelco, Bellefonte, Pa., USA) was used to extract the volatile organic compounds from the headspace of the vials containing the gauze. The exposure was performed at room temperature for 15 hours.

The compounds collected from the right and left armpit area of Male 4, after correction for background compounds present, are listed in Table 11. All of the human compounds extracted were present in both the right and left armpit of Male 4. FIG. 1 shows the relative peak area ratios of the seven human compounds extracted from the right and left armpit samples, which is similar between both right and left armpit samples.

TABLE 11

| Human Compounds Extracted | Retention Time | Right Armpit | Left Armpit |
|---|---|---|---|
| Hexanal | 5.5 | X | X |
| Nonane | 8.43 | X | X |
| α-Pinene | 9.13 | X | X |
| 5-Hepten-2-one, 6-methyl- | 10.33 | X | X |
| Undecane | 12.43 | X | X |
| Nonane, 1-chloro- | 13.49 | X | X |
| 6,10-dimethyl-5,9-undecadien-2-one | 17.57 | X | X |

Comparison of Armpit Sampling Techniques: Worn vs. Wiped Materials: All gauze used in this study was DUKAL brand, 100% cotton, sterile, 2×2, 8 ply, gauze sponges (DUKAL Corporation, Syosset, N.Y.). The sterile gauze was not subjected to any additional sterilization processes. The unscented soap used in this study was Dove unscented moisturizing soap (Unilever, Greenwich, Conn.). The vials used in this study were 10 mL glass, clear, screw top vials with PTFE/Silicone septa (SUPELCO, Bellefonte, Pa., USA). Prior to use, the glass vials and septa were rinsed with acetone and baked at 210° C. for 48 hrs to remove volatile compounds present initially in the vials.

The sterile gauze were sealed into a 10 mL glass vial, extracted and analyzed to determine which compounds were present initially on the gauze. These compounds were noted prior to use for background purposes. Male 2 was required to use fragrance free soap and to discontinue the use of deodorant, lotions and perfumes for 48 hours before sampling to minimize the influence of the "tertiary odors." A piece of gauze was fastened with a safety pin to the left armpit area of Male 2's shirt and worn for 9 hrs. After the sampling time was complete the gauze was removed by the subject and placed back into the original 10 mL glass vials. The following day Male 2 exercised for 1 hr, then wiped the left armpit area with a piece of sterile gauze, and returned the gauze to the original 10 mL glass vial.

The collected armpit samples were allowed to sit for 24 hrs, then extracted using SPME. DVB/CAR/PDMS 50/30 μm fibers (Supelco, Bellefonte, Pa., USA) was used to extract the volatile organic compounds from the headspace of the vials containing the gauze. The exposure was performed at room temperature for 15 hours.

Evaluation of sampling techniques (wiping vs. wearing) indicated that both techniques produced extractable human compounds. The wiping technique seemed to allow better collection and gathered a greater number of human compounds, in addition to having less environmental influences from safety pins and clothing as are present when the gauze is worn. The wiping technique also provided a more concentrated sample than wearing the gauze, leading to higher abundance levels of the compounds collected. The identity of the compounds collected in the wiped and worn experiments is listed in Table 12.

TABLE 12

| Human Compounds | Wiped | Worn |
| --- | --- | --- |
| Toluene | | X |
| Hexanal | X | |
| Phenol | X | |
| 5-Hepten-2-one, 6-methyl- | X | X |
| Hexanoic acid | X | |
| Octanal | | X |
| 1-Hexanol, 2-ethyl- | X | |
| Benzyl Alcohol | X | |
| 1-Hexanol, 2-ethyl- | | X |
| 1,6-Octadien-3-ol, 3,7-dimethyl- | X | |
| Phenylethyl Alcohol | X | |
| 2-Nonenal, (E)- | X | X |
| Acetic acid, phenylmethyl ester | X | |
| Nonane, 1-chloro- | | X |
| Octanoic Acid | X | |
| Dodecane | | X |
| 6-Octen-1-ol, 3,7-dimethyl-, (R)- | X | |
| Nonanoic acid | X | |
| Tridecane | X | X |
| Undecanal | X | |
| Decanoic acid | X | |
| Tetradecane | X | X |
| Dodecanal | X | |
| 5,9-Undecadien-2-one, 6,10-dimethyl- | X | X |
| Tetracosane | | X |
| Pentadecane | X | X |
| Hexadecane | | X |
| Heptadecane | X | |

Comparison of Odor Profiles Obtained from the Armpit Area of Two Males

All gauze used in this study was DUKAL brand, 100% cotton, sterile, 2×2, 8 ply, gauze sponges (DUKAL Corporation, Syosset, N.Y.). The sterile gauze was not subjected to any additional sterilization processes. The unscented soap used in this study was Dove unscented moisturizing soap (Unilever, Greenwich, Conn.). The vials used in this study were 10 mL glass, clear, screw top vials with PTFE/Silicone septa (SUPELCO, Bellefonte, Pa., USA). Prior to use, the glass vials and septa were rinsed with acetone and baked at 210° C. for 48 hrs to remove volatile compounds present initially in the vials.

The sterile gauze was sealed in 10 mL glass vials, extracted, and analyzed to determine which compounds were present initially on the gauze. These compounds were noted prior to use for background purposes. The only contact the researcher had with the sterile gauze is when the gauze is sealed initially in the glass vials. In order to reduce contamination, powderless latex gloves were worn and contact between the gloves and the gauze was minimized. Gloves were changed between each piece of gauze that was handled. Two unrelated, twenty-four year old males were evaluated. Subjects used were required to use fragrance free soap and to discontinue the use of deodorant, lotions and perfumes for 48 hours before sampling to minimize the influence of the "tertiary odors." In this study, no attempt was made to control the diet of the subjects being sampled. Each subject exercised outdoors for a period of 1 hour wearing a tank top to eliminate compounds present due to clothing. Each subject then sampled themselves, using a 2×2 sterile gauze pad to wipe the armpit area, collect their own sweat, and then re-seal the sample back into the 10 mL glass vial. All samples were stored in the 10 mL vials at room temperature. Subjects were sampled on different days and at different times throughout the same day to evaluate the stability and reproducibility of the resulting scent profile. For intraday sampling, the first sample was taken in the morning and the second sample was taken 10 hours later. Interday samplings were all taken prior to 12:00 pm. The average humidity and temperature for the days sampling occurred are listed below in Table 13.

TABLE 13

| SUBJECT | DATE | AVERAGE TEMP. (° F.) | AVERAGE HUMIDITY (%) |
| --- | --- | --- | --- |
| Male 4, Week 1 | Apr. 07, 2004 | 73 | 63 |
| Male 4, Week 3 | Apr. 18, 2004 | 73 | 62 |
| Male 2 | Apr. 10, 2004 | 80 | 76 |

Each sample was analyzed individually as received. The samples were collected from Male 4 and Male 2, allowed to sit for 24 hours, then extracted using SPME. DVB/CAR/PDMS 50/30 μm fibers (Supelco, Bellefonte, Pa., USA) were used to extract the volatile organic compounds from the headspace of the vials containing the gauze. The exposure was performed at room temperature for 15 hours. The GC/MS method was as described above.

Male 4 was sampled once in the morning (Sampling 1), then again ten hours later (Sampling 2). Table 14 lists the previously reported compounds which were extracted in both samplings. Sampling 1 produced a higher abundance of compounds than Sampling 2, and cyclotetradecane, hexanal, and nonanoic acid were only seen in Sampling 1. Table 15 shows the relative peak ratios of the common compounds relative to (E)-2-nonenal extracted from the same individual at different times on the same day. (E)-2-nonenal was chosen as the compound to which the ratios are related because it is extracted in all of the samples presented here. The ratios of the common compounds between the same individual on the same day appear to be relatively similar, with only minor differences.

TABLE 14

| COMPOUND NAME | M.W. | SAMPLING 1 | SAMPLING 2 |
| --- | --- | --- | --- |
| (E)-2-nonenal[7] | 140 | X | X |
| (E)-2-octenal[7] | 126 | X | X |
| (E,E)-2,4-nonadienal[1,6,7] | 138 | X | X |
| (E,E)-2,4-decadienal[7] | 152 | X | X |
| 3,7-dimethyl-2,6-octadienal | 152 | X | X |
| 6,10-dimethyl-5,9-undecadien-2-one[1] | 194 | X | X |
| Benzaldehyde[1,6] | 106 | X | X |
| benzyl alcohol[1,4] | 108 | X | X |
| Cyclotetradecane[1] | 196 | X | |
| Dodecanoic Acid[1,3,5,6] | 200 | X | X |

TABLE 14-continued

| COMPOUND NAME | M.W. | SAMPLING 1 | SAMPLING 2 |
|---|---|---|---|
| Heptadecane[1,2] | 240 | X | X |
| Heptanal[1,5,6] | 114 | X | X |
| Hexanal[5,7] | 100 | X | |
| Nonanoic Acid[1,3,4] | 158 | X | |
| Octadecane[1] | 254 | X | X |
| Toluene[1,6] | 92 | X | X |
| Undecanal[5] | 170 | X | X |

[1]Previously reported as a component in human skin emanation;
[2]Previously reported as a volatile component of the skin;
[3]Previously reported as a component of armpit odor;
[4]Previously reported as a component of armpit odor;
[5]Previously reported as a component of skin emanations;
[6]Previously reported as a component of skin emanations;
[7]Previously reported as a component of armpit odor;
[8]Previously reported as a component of fingerprint residue

TABLE 15

| | COMPOUND | PEAK RATIO (S1) | PEAK RATIO (S2) |
|---|---|---|---|
| 1 | (E)-2-nonenal | 1.0000 | 1.0000 |
| 2 | (E)-2-octenal | 1.0205 | 0.6842 |
| 3 | (E,E)-2,4-nonadienal | 0.9683 | 0.7200 |
| 4 | (E,E)-2,4-decadienal | 0.3247 | 0.2914 |
| 5 | 3,7-dimethyl-2,6-octadienal | 1.6698 | 2.5324 |
| 6 | 6,10-dimethyl-5,9-undecadien-2-one | 5.1980 | 6.7795 |
| 7 | benzaldehyde | 1.1034 | 0.4013 |
| 8 | benzyl alcohol | 0.4492 | 0.5847 |
| 9 | dodecanoic acid | 2.6417 | 2.4870 |
| 10 | heptadecane | 0.3107 | 0.3302 |
| 11 | heptanal | 0.7935 | 0.6783 |
| 12 | octadecane | 0.1931 | 0.1891 |
| 13 | toluene | 0.0810 | 0.0850 |
| 14 | undecanal | 1.1646 | 1.5836 |

Interday analysis of the same individual is summarized in Table 16 for compounds extracted between Week 1 and Week 3 (Sampling 1 and Sampling 2) for Male 4. Table 17 shows the relative peak ratios of the previously reported common compounds between Male 4(W1, W3(S1), W3(S2)) and Male 2 relative to (E)-2-nonenal. Although there is some variation present within the same individual, the ratio pattern is still distinguishable between individuals with significantly greater variation in the ratios of components observed between individuals tested than that seen for one individual (Table 18). Table 19 also lists the compounds between Male 4 and Male 2 which are uncommon between the individuals. A combination of the relative ratios of the common compounds between the individuals along with the presence of some unique compounds allows for the chromatographic distinction between individuals.

TABLE 16

| Compound Name | M.W. | Wk 1 | Wk 3 S1 | Wk 3 S2 |
|---|---|---|---|---|
| (E)-2-nonenal[7] | 140 | X | X | X |
| (E)-2-octenal[7] | 126 | X | X | X |
| (E,E)-2,4-nonadienal[1,6,7] | 138 | | X | X |
| (E,E)-2,4-decadienal[7] | 152 | | X | X |
| 3,7-dimethyl-2,6-octadienal[1] | 152 | | X | X |
| 6,10-dimethyl-5,9-undecadien-2-one[1] | 194 | X | X | X |
| 6-methyl-5-hepten-2-one[1,2,6] | 126 | X | | |
| Benzaldehyde[1,6] | 106 | X | X | X |
| benzyl alcohol[1,4] | 108 | X | X | X |
| Cyclotetradecane[1] | 196 | X | X | |
| Dodecanoic Acid[1,3,5,6] | 200 | X | X | X |
| Heptadecane[1,2] | 240 | X | X | X |
| Heptanal[1,5,6] | 114 | | X | X |
| Hexanal[5,7] | 100 | | X | |
| Nonane[1,6] | 128 | X | | |
| Nonanoic Acid[1,3,4] | 158 | X | X | |
| Octadecane[1] | 254 | X | X | X |
| Phenol[1,3,4] | 94 | X | | |
| Toluene[1,6] | 92 | | X | X |
| Undecanal[5] | 170 | X | X | X |

[1]Previously reported as a component in human skin emanation;
[2]Previously reported as a volatile component of the skin;
[3]Previously reported as a component of armpit odor;
[4]Previously reported as a component of armpit odor;
[5]Previously reported as a component of skin emanations;
[6]Previously reported as a component of skin emanations;
[7]Previously reported as a component of armpit odor;
[8]Previously reported as a component of fingerprint residue.

TABLE 17

| | COMPOUND | PEAK RATIO M4 (W1) | PEAK RATIO M4 (W3) S1 | PEAK RATIO M4 (W3) S2 | AVE. PEAK RATIO M1 | STAND. DEV. | R.S.D |
|---|---|---|---|---|---|---|---|
| 1 | (E)-2-nonenal | 1 | 1 | 1 | 1 | 0 | 0 |
| 2 | 6,10-dimethyl-5,9-undecadiene-2-one | 4.0209 | 6.7795 | 5.1980 | 5.3328 | 1.3842 | 25.95 |
| 3 | Benzyl alcohol | 0.6440 | 0.5847 | 0.4492 | 0.5593 | 0.0998 | 17.84 |
| 4 | Dodecanoic acid | 1.3175 | 2.4870 | 2.6417 | 2.1487 | 0.7240 | 33.69 |
| 5 | Heptadecane | 0.3300 | 0.3302 | 0.3107 | 0.3236 | 0.0112 | 3.461 |
| 6 | Octadecane | 0.2574 | 0.1891 | 0.1931 | 0.2132 | 0.0383 | 17.96 |
| 7 | Undecanal | 0.6456 | 1.5836 | 1.1646 | 1.1312 | 0.4699 | 41.54 |

TABLE 18

| | COMPOUND | PEAK RATIO (M1) | PEAK RATIO (M2) | M2/M1 RATIO |
|---|---|---|---|---|
| 1 | (E)-2-nonenal | 1 | 1 | 1 |
| 2 | 6,10-dimethyl-5,9-undecadien-2-one | 5.3328 | 13.5840 | 2.5472 |
| 3 | Benzyl alcohol | 0.5593 | 2.1466 | 3.8378 |
| 4 | Dodecanoic Acid | 2.1487 | 4.9138 | 2.2868 |
| 5 | Heptadecane | 0.3236 | 6.4197 | 19.8381 |

TABLE 18-continued

|   | COMPOUND | PEAK RATIO (M1) | PEAK RATIO (M2) | M2/M1 RATIO |
|---|----------|-----------------|-----------------|-------------|
| 6 | Octadecane | 0.2132 | 0.9252 | 4.3404 |
| 7 | Undecanal | 1.1312 | 3.7387 | 3.3049 |

TABLE 19

| Compound Name | M.W. | Formula | M4 | M2 |
|---|---|---|---|---|
| ALCOHOL | — | — | — | — |
| 3,7-dimethyl-6-octen-1-ol[1] | 156 | $C_{10}H_{20}O$ |  | X |
| Phenol[1,3,4] | 94 | $C_6H_6O$ |  | X |
| Phenylethyl alcohol[1] | 122 | $C_8H_{10}O$ |  | X |
| ALDEHYDE | — | — | — | — |
| (E)-2-octenal[7] | 126 | $C_8H_{14}O$ | X |  |
| (E,E)-2,4-decadienal[7] | 152 | $C_{10}H_{16}O$ | X |  |
| (E,E)-2,4-nonadienal[1,6,7] | 138 | $C_9H_{14}O$ | X |  |
| 3,7-dimethyl-2,6-octadienal[1] | 152 | $C_{10}H_{16}O$ | X |  |
| Benzaldehyde | 106 | $C_7H_6O$ | X |  |
| ALIPHATIC/AROMATIC | — | — | — | — |
| Cyclotetradecane[1] | 196 | $C_{14}H_{28}$ | X |  |
| Octadecane[1] | 254 | $C_{18}H_{38}$ | X |  |
| Pentadecane[1,2] | 212 | $C_{15}H_{32}$ |  | X |

[1]Previously reported as a component in human skin emanation;
[2]Previously reported as a volatile component of the skin;
[3]Previously reported as a component of armpit odor;
[4]Previously reported as a component of armpit odor;
[5]Previously reported as a component of skin emanations;
[6]Previously reported as a component of skin emanations;
[7]Previously reported as a component of armpit odor;
[8]Previously reported as a component of fingerprint residue.

Creation of a Method for Producing Analytically Clean Absorber Materials

Gravity and Steam Re-sterilization: In order to determine whether re-sterilizing gauze pads is an effective route for the removal of compounds initially present on the gauze pad, each piece of sterile eye pad (Kendall Curity, Tyco Health Care Group, Mansfield, Mass., USA) was cut in half, one piece was placed in a 10 mL glass vial and the other was run through either a steam or gravity sterilizer.

The 250 gravity cycle is a 30 minute cycle with a 30 minute dry time. The air in the chamber is removed by introducing steam in the top of the sterilizer chamber, which displaces the air out a drain at the bottom of the sterilizer. There is a gauge in the drain that senses when steam starts to enter. When the steam is sensed by the gauge, the sterilization time begins.

The prevac cycle (vacuum pressurized) is a four minute cycle at 270° F., which starts after the pulsing cycle removes the air from the chamber. The steam enters the chamber from the top, and air is removed from the bottom. A gauge monitors when steam has replaced air and the sterilization cycle begins. It is a shorter cycle because of the increase in temperature and the efficiency of the steam removal. The dry time for the prevac cycle is 30 minutes. Dry time is based on ability to dry items and can vary from 10 minutes to greater than 30 minutes. Variables in the load, such as metal mass, wrapping material, density, and the like affect the dry time. The water is not re-circulated in the sterilizers. The sterilizers are cleaned weekly with a product called AMSCRUB.

Figure 2A:
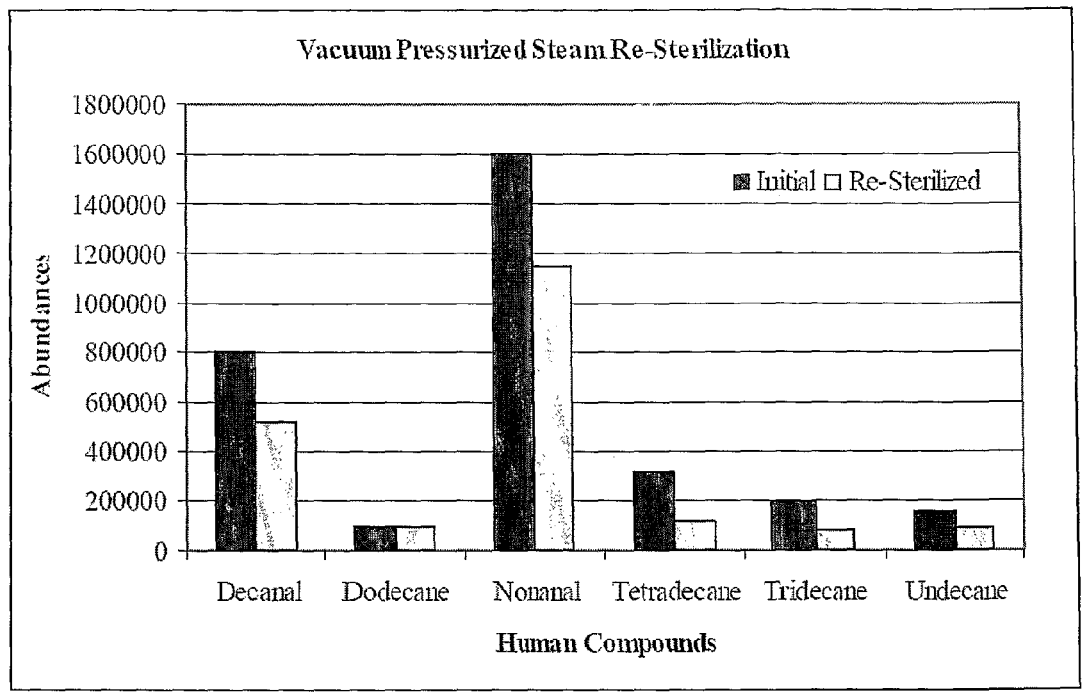
FIG. 2A shows a comparison of compounds in a fabric before and after sterilization using vacuum pressurized steam.
Figure 2B:
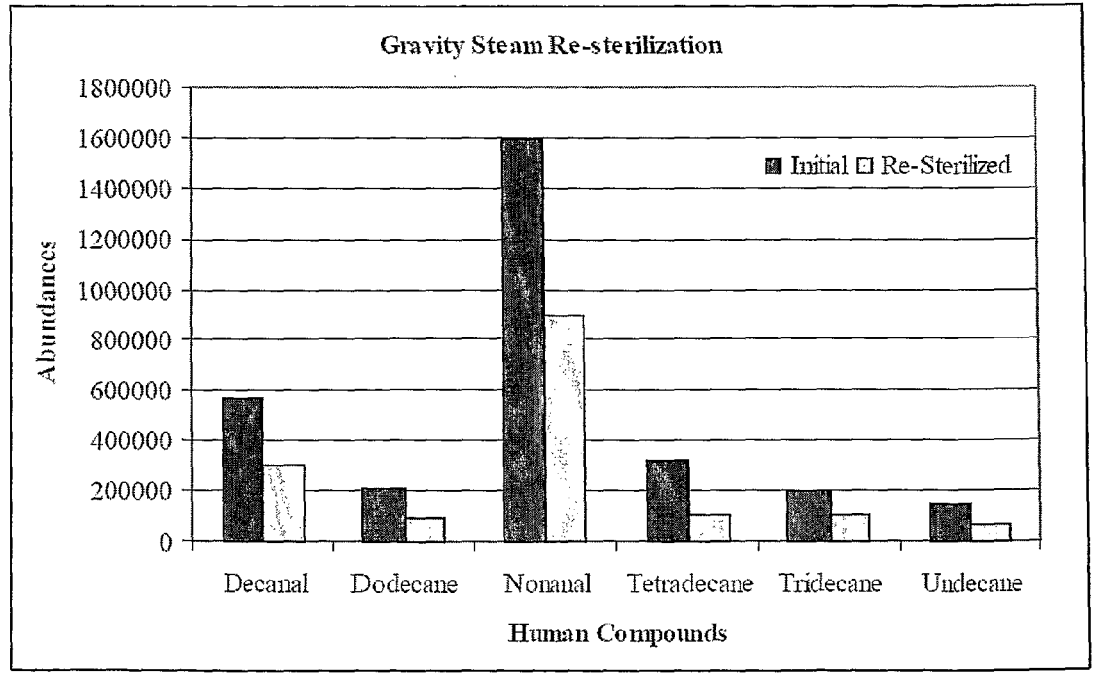
FIG. 2B shows a comparison of compounds in a fabric before and after sterilization using gravity steam.

Headspace evaluation of each half of the absorbers pre and post re-sterilization using either steam or gravity sterilization resulted in a reduced amount of human compounds present initially on the absorber. FIG. 2A and FIG. 2B compare the peak heights of human compounds present initially in the eye pad and after re-sterilization. As can be seen from the graphs, re-sterilizing absorber materials using steam or gravity techniques does not result in a chromatographically clean absorber material.

Soxhlet Extraction: In triplicate, a piece of DUKAL gauze of about 0.36 g was extracted with 200 mL for 9 hrs using either methanol or chloroform HPLC grade solvents (Fischer Scientific, Pittsburgh, Pa.). After the Soxhlet extractions were completed, the gauze was placed inside a baked out glass beaker and cover with foil for 24 hrs to allow for solvent evaporation, then re-placed inside the 10 mL glass vial for SPME-GC/MS analysis.

Figure 3:
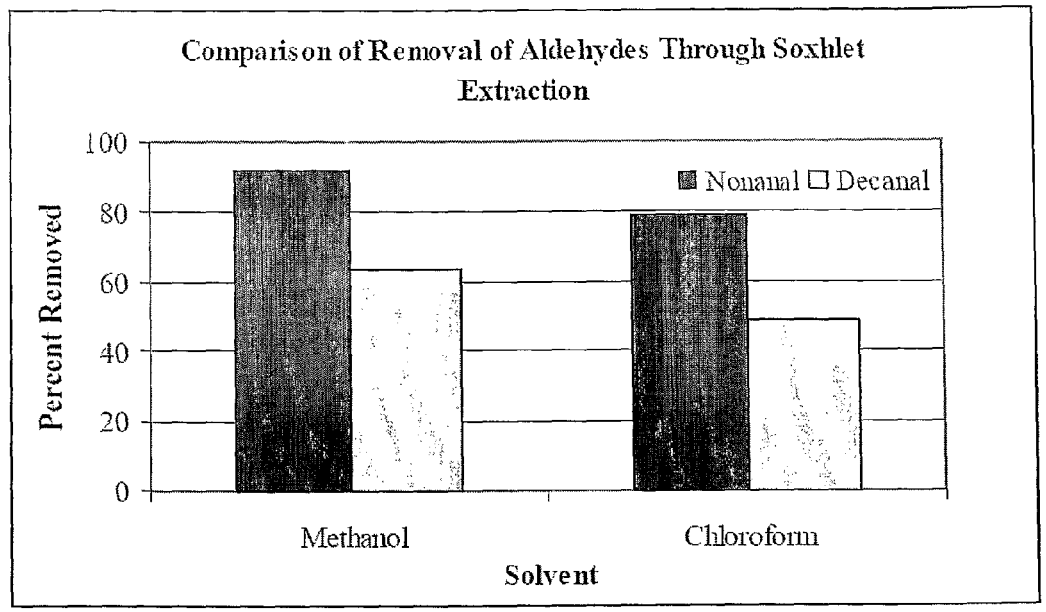
FIG. 3 shows a comparison of the removal of aldehydes from a fabric using Soxhlet extraction.

The nine hour Soxhlet extractions using either methanol or chloroform did not result in complete removal of the aldehydes from the sorbent material, as can be seen in FIG. 3. For example, utilizing the methanol solvent, nonanal had an average removal rate of 91.71% and decanal had an average removal rate of 63.35%. In addition to poor results, a Soxhlet extraction process also entails a long total extraction time as the solvent process (nine hour extraction and twenty-four hour drying). Furthermore, Soxhlet extractions require the use and disposal of large amounts of solvent which add to the cost of the process. Thus, Soxhlet extraction is not a preferred means to pre-treat sorbent materials.

Supercritical Fluid Extraction: SFC grade carbon dioxide (Airgas, Radnor, Pa.) was pressurized by an ISCO Model 260D Syringe Pump attached to an ISCO SFX 2-10 Supercritical Fluid Extractor (ISCO, Lincoln, Nebr.). For the development of the optimal SFE conditions, DUKAL brand gauze was used exclusively, because it is 100% cotton whereas other materials studied ranged in their composition. A piece of gauze weighing about 0.36 g was placed inside a 10 mL SFE cell (ISCO, Lincoln, Nebr.). When evaluating the effect of adding a modifier in extraction efficiency, the modifier was added directly to the extraction cell by pipeting 500 µL onto the gauze pad in the extraction cell. The extraction temperature (36° C., 130° C., or 150° C.) within the cell was controlled through use of an ISCO SFE Temperature Controller contained within the SFE Extractor, and an ISCO Restrictor Temperature Controller was used to maintain temperatures during the dynamic aspect of the extractions. The effect of various pressures on the extraction efficiencies also was evaluated at pressures that included both 2500 and 4500 psi. Various static/dynamic time combinations were evaluated including 30/10 min and 45/10 min. Extraction analytes were not collected or evaluated post extraction. After the extractions, the gauzes were removed from the extraction cell, placed inside a 10 mL vial (Supelco, Bellefonte, Pa.), and headspace analysis then was conducted using SPME-GC/MS as described herein later. To evaluate the ruggedness of the optimal SFE conditions, varying sizes and types of materials were run through the SFE, and the amount of modifier was scaled-up based on a weight ratio of 500 µL to the about 0.36 g.

Figure 4:
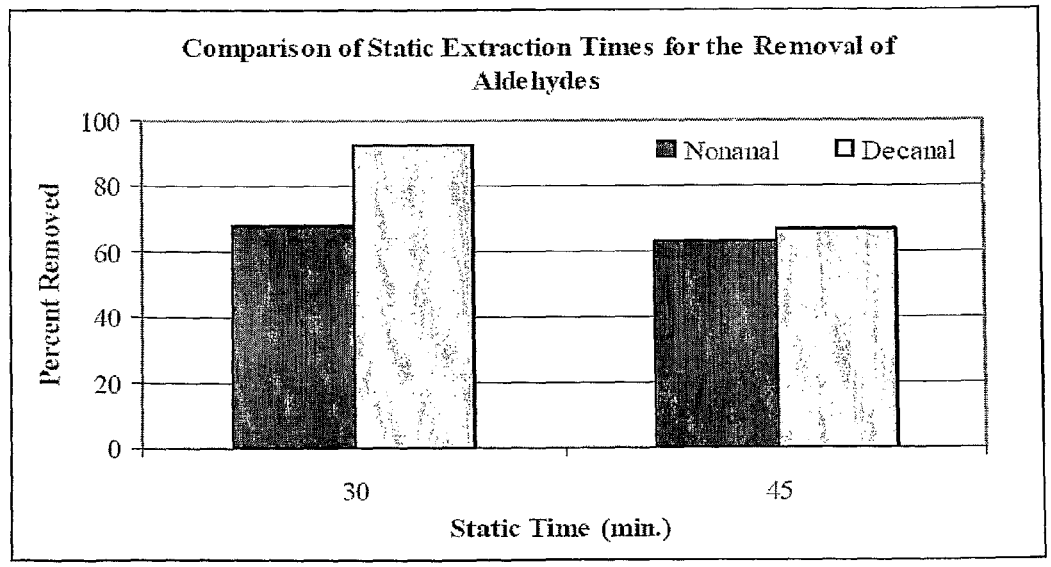
FIG. 4 shows a comparison of the removal of aldehydes from a fabric at 30 minutes extraction and 45 minutes extraction.

The compounds targeted for removal contain compound classes that are both polar and non-polar. Due to this fact, pure $CO_2$ may not be adequate for complete removal of the polar compounds because $CO_2$ has high solubility for non-polar analytes. The use of modifiers requires a static step followed by a dynamic step, and the removal rates of the polar compounds are usually limited by solubility considerations. Static/dynamic extraction times of 30/10 min and 45/10 min at (130° C. and 4500 psi) were evaluated without the presence of the modifiers. While the extended exposure to the carbon dioxide solvent removed 100% of long chain alkanes, such as dodecane, tridecane, hexadecane, and heptadecane, aldehydes were not removed. The longer static extraction time demonstrated minimal extraction recoveries when compared to the shorter extraction period for the polar compounds as can be seen in FIG. 4. Nonanal, for example, had a removal rate of 68.11% at 30 minutes, compared to 63.30% at the 45 minute period. Furthermore, decanal, another human scent aldehyde component, portrayed a relatively high 92.32% removal rate at the 30 minute static extraction period compared to a lower 66.70% removal rate at the prolonged static extraction time. These results reinforce the fact that the 45 minute extraction provides minimal extraction recoveries and, thus, low removal rates of target human scent volatile organic compounds found within the sorbent material evaluated.

Non-polar compounds were almost completely removed, while more polar compounds remained, indicating a possible solubility impediment to the complete removal of the aldehydes from the sample matrix. The application of polar modifiers to the extraction cell can enhance the solubility of the polar compounds of interest and thus help to achieve a complete removal of all compounds from the matrix.

Effect of Pressure: Another way to increase the solubility of the $CO_2$ solvent is to increase pressure at a constant temperature. In this case, the temperature was held at 36° C. (the critical point for carbon dioxide gas is 31.1° C.), and the extraction efficiencies were measured at pressures of 2500 and 4500 psi. Each pressure evaluated resulted in complete removal of the nonpolar compounds, but the increase in pressure did not uniformly increase the removal rates of the target polar compounds from the sample matrix. This result was expected for the nonpolar analytes because increasing the pressure at a constant temperature greatly increases solvent strength of $CO_2$ and, thus, increases the solubility of most analytes found within the sample matrix. Nonanal portrayed a 96.60% removal rate at the lower pressure of 2500 psi, while dropping to a removal rate of 78.03% at the higher pressure. Decanal was removed 91.58% at the lower pressure, compared to a lower value of 76.77% removal rate at 4500 psi of pressure. The poor result for the removal polar analytes may be due to solubility problems, and the temperature (36° C.) at which both pressures were evaluated may also have affected the results obtained. Nonetheless, solubility limitations are present when using pure $CO_2$ as an extraction solvent for polar analytes, which may be overcome with the addition of polar modifiers.

Figure 5:
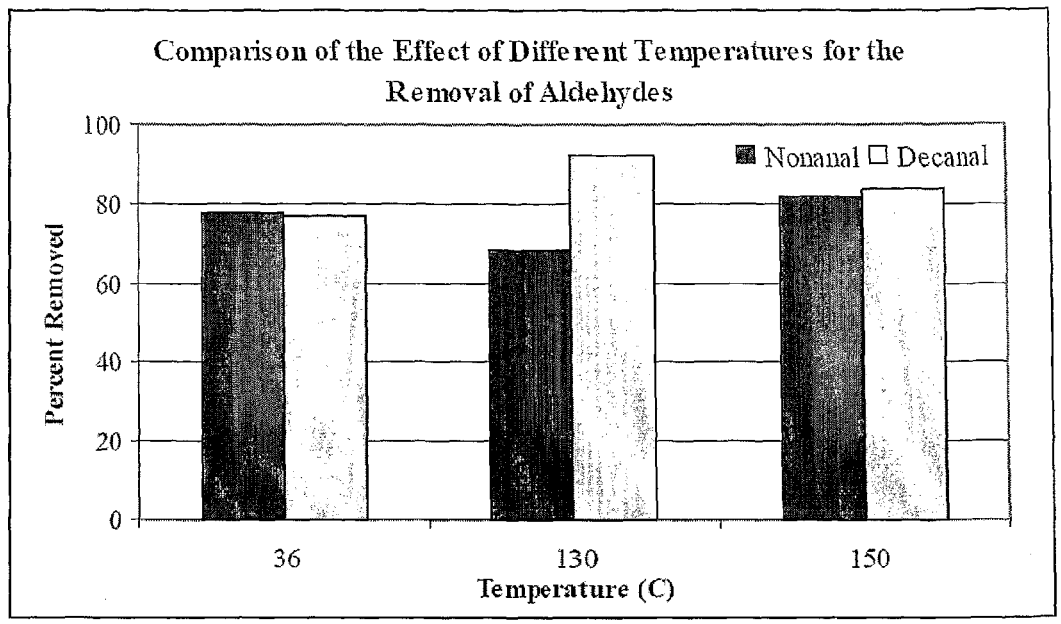
FIG. 5 shows a comparison of the effect of different temperatures in removing aldehydes from a fabric.

Effect of Temperature: Varying the temperature during SFE affects both the density of the fluid and the volatile property of the analytes. An increase in extraction efficiency with increasing temperature is dependent on molecular weight as well as the vapor pressure of the analytes. Again utilizing the static/dynamic time of 30/10 min along with a pressure of 4500 psi, three temperatures (36, 130, and 150° C.) were evaluated. The results show that increasing the temperature through 150° C. was beneficial for nonanal. However, decanal yielded much better results at a temperature of 130° C. vs. 150° C. As seen in FIG. 5, a lower temperature of 36° C. provided nonanal with a much higher removal rate (78.03%) compared to the amount removed at 130° C. (68.11%). Decanal, on the other hand, was observed to give the best removal rate (92.32%) at 130° C. In all the extractions performed, decanal proved to be the hardest target VOC to be removed from the sample matrix, thereby giving the 130° C. temperature value an advantage to optimize its extraction efficiency.

Effect of Modifiers: Due to the nonpolar characteristics of $CO_2$, there is an inherent limited ability to dissolve polar analytes from the matrix. The use of modifiers enhances the extraction when the solubility of the target analytes is insufficient to yield reasonable extraction rates (solubility hindrances), and can also enhance the rate of kinetic/desorption process resulting in a greater interaction with the sample matrix. Thus, a study was conducted to evaluate the effect of different modifiers and their relation to extraction efficiencies of target compounds found in sorbent materials. The extractions performed with each modifier at a static/dynamic timeframe of 30/10 min were conducted at a fixed pressure and temperature of 4500 psi, 130° C. respectively. The modifiers were all spiked directly onto the gauze while inside the extraction cell. The modified solvents evaluated included methanol, chloroform, HPLC water, and a methanol/water combination where 5% water by weight (50 μL) along with 500 μL of methanol was used.

Figure 6:
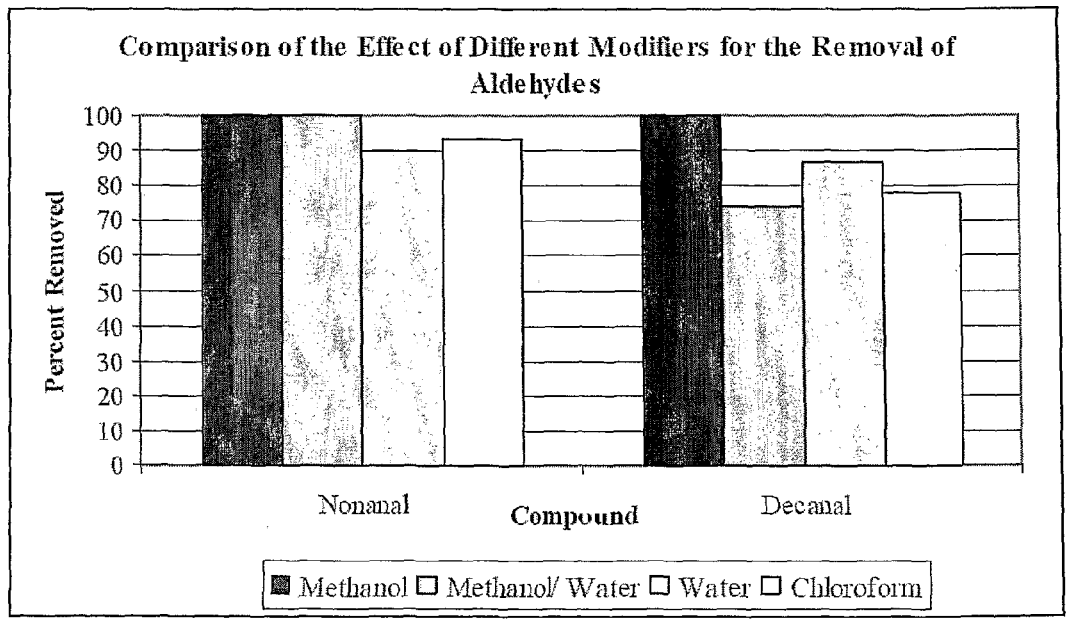
FIG. 6 shows a comparison of the effect of different modifiers for the removal of aldehydes from a fabric.

For all modifiers studied, long chain alkanes such as tridecane, undecane, pentadecane, hexadecane, and heptadecane were completely removed from the sample matrix. The percent removed for nonanal and decanal, the main polar compounds, proved to be challenging to remove, can be seen for the various modifiers in FIG. 6. Methanol demonstrated 100% removal of the polar compounds of interest. The methanol/water combination did not produce the same removal efficiency, i.e. the percent removal of decanal drops to 74.26%. When water is used as the only modifier in the extraction, the removal rates improve slightly than those of the MeOH/water mixture modified samples. Chloroform (more similar to water when located in Snyder's triangle) generated a lower removal percentage for decanal (77.90%) compared to nonanal (93.31%).

In order to test the ruggedness of the methanol-modified SFE parameters, varying sizes, thicknesses, and types of materials were run through the SFE, and the amount of modifier was scaled-up based on a weight ratio of 500 μL to the about 0.36 g. The scaling up of the amount of methanol added to the extraction cell resulted in the complete removal of all of the compounds of interest, producing an analytically clean sorbent material. The SFE parameters for achieving an analytically clean absorber material have been determined to include the direct spiking of methanol modifier (amount determined by using the ratio of 500 μL to ~0.36 g), thirty minutes of static extraction with a pressure of 4500 psi at 130° C. followed by a ten minute dynamic extraction.

Evaluation of Storage Materials Commonly Used to Collect Human Scent

Materials included DUKAL brand, sterile, 2×2, 8 ply, 100% cotton gauze sponges (DUKAL Corporation, Syosset, N.Y., USA); 10 mL glass, clear, screw top vials with PTFE/Silicone septa (SUPELCO, Bellefonte, Pa., USA); supercritical grade carbon dioxide (Air Products, Allentown, Pa., USA); HPLC grade methanol (Fisher Scientific, Pittsburgh, Pa., USA); Ziploc, Freezer Guard Seal, Pint Size, 7.0"×5.25", (SC Johnson & Sons Inc., Racine, Wis., USA); Kapak Heavy Duty SealPAK Pouches, PET//LLDPE, 4.5 mils thick, 6.5"× 8" (Kapak Corporation, Minneapolis, Minn., USA); Kapak Aluminized Pouches, tri-layer polymer chemistry featuring an aluminum film, 6.5"×8", Job# J9539, Lane#2, Box#056 (Kapak Corporation, Minneapolis, Minn., USA); Polyethylene Pouches, 3"×3", 2 mil thick, Item#01-0303-2 (Veripak, Atlanta, Ga., USA); Divinylbenzene/Carboxen on Polydimethylsiloxane (DVB/CAR on PDMS) 50/30 μm fibers (SUPELCO, Bellefonte, Pa., USA); and Maxi Seal, electric heat sealer, Model: MS-8, Power: 310W, Voltage: 120V, Frequency: 60 Hz (Premium Balloon Accessories, USA).

Prior to use, gauzes were cleaned using a methanol modified supercritical fluid extraction as described above, placed into 10 mL glass, clear, screw top vials with PTFE/Silicone septa, extracted using Divinylbenzene/Carboxen on Polydimethylsiloxane (DVB/CAR on PDMS) for 15 hrs, and then analyzed by GC/MS to ensure analytical cleanliness. In triplicate, a piece of treated gauze was sealed into each of the five types of storage materials which include: (1) 10 mL glass, clear, screw top vials with PTFE/Silicone septa, (2) Ziploc, Freezer Guard Seal, Pint Size bags, (3) KPAK Heavy Duty SealPAK Pouches, (4) KPAK Aluminized Pouches, and (5) polyethylene pouches. A heat sealer was used to seal both the KPAK Heavy Duty SealPak and Aluminized pouches as well as the polyethylene, whereas the Ziploc Freezer Guard bags were sealed using the zipper at the top of the bag. These pouches were then allowed to sit for one, two, and five weeks. At the end of the time periods, each piece of gauze was removed from its respective storage material and placed back into its original vial using tweezers previously rinsed with a bleach solution and dried. Each stored gauze pad was then re-evaluated using the same SPME-GC/MS method.

As shown in Table 20, the storage material which contributes the least amount of compounds onto the SFE treated gauze is the 10 mL glass vial, whereas the material which contributes the most is the Heavy Duty Kapak pouches. As can be seen in the results for the Ziploc storage, there is variability present in the amount of compounds deposited on the gauze within the same material over time, these variations may be due to the manufacturing process as all the Ziploc bags were from the same box.

TABLE 20

| Storage Material | Ave. Number Of Compounds | Ave. Number of Human Compounds |
|---|---|---|
| WEEK 1 | | |
| 10 mL glass vial | 3 | 1 |
| Polyethylene | 19 | 6 |
| Ziploc Freezer Guard | 40 | 9 |
| Aluminum Kapak | 93 | 6 |
| Heavy Duty Kapak | 116 | 7 |
| WEEK 2 | | |
| 10 mL glass vial | 2 | 0 |
| Polyethylene | 24 | 7 |
| Ziploc Freezer Guard | 19 | 3 |
| Aluminum Kapak | 85 | 3 |
| Heavy Duty Kapak | 116 | 8 |
| WEEK 5 | | |
| 10 mL glass vial | 6 | 1 |
| Polyethylene | 11 | 2 |
| Ziploc Freezer Guard | 15 | 3 |
| Aluminum Kapak | 88 | 2 |
| Heavy Duty Kapak | 107 | 6 |

Evaluation of Compounds Present in the Headspace of Different Cleansers

The occurrence of secondary transfer of DNA between people and objects has been observed. The presence of cells are necessary for the recovery of DNA profiles, as an individual comes into contact with an object, there is a transfer of materials and in this case, the transfer of skin cells containing DNA. Skin cells are also considered a substrate/medium for human odor. In order to remove the possibility that the odors analyzed for an individual are a combination of more than one individual through a secondary transfer of cells, it is necessary to incorporate washing of the hands into the sampling strategy.

It has been observed that soaps which claim to be fragrance free appear to have an odor when presented to the human nose. In addition, there is a concern that soaps made from animal fat may contain components reported to be present in human odor as they are created from a biological material. Studies of fatty acid soap residue on human skin have shown a linear increase of residue with soaping time, and a similar increase with the concentration of calcium in the water (because of the formation of insoluble calcium salts with the acids). These studies have also shown that the increased absorption can be counterbalanced with an increase of rinsing time/decrease of soaping time. A headspace evaluation of the compounds present in the headspace above various brands of soaps and body washes, as well as soaps made from differing substrates has been conducted.

Twenty-five different cleansers evaluated are listed above under "Cleansers." The vials used in this study were 10 mL glass, clear, screw top vials with PTFE/Silicone septa (SUPELCO, Bellefonte, Pa., USA).

In triplicate, an allotment of cleanser materials was placed in a 10 mL glass vial. The headspace of each vial containing the cleanser was extracted using DVB/CAR on PDMS 50/30 µm fibers (SUPELCO, Bellefonte, Pa., USA) which were exposed for 5 minutes. The GC/MS method used was as described above.

Twenty-five cleansers made from different types of materials (emu oil, animal fat, olive oil, glycerin, and various organic materials), both fragrance-free and scented, were evaluated through headspace SPME-GC/MS to determine which compounds were present. Headspace analysis of different soap types revealed that soaps made from animal fat, as well as organic based soaps, show the presence of compounds previously reported in humans. The optimal soap chosen for use in sampling subjects was determined using the presence of commonly reported compounds in humans in the headspace of soaps as the criteria for exclusion. The comparison shown here is done with fragrance-free cleansers to minimize the extraneous odor compounds present. Table 21 shows a summary of the human compounds commonly seen in the headspace of fragrance-free soaps made from animal fat as compared to those made from olive oil. Olive oil-based fragrance-free soaps did not contain any human compounds, whereas animal fat based fragrance-free soaps did show the presence of many types of human compounds. The peaks seen in the chromatograms for olive oil-based soaps are siloxane and propylene glycol, due to the column/fiber coating and the soap base respectively. In order to eliminate the possibility that the odor profile has influences from the type of soap being used for washing the body, olive oil-based, fragrance-free soaps were used in the sampling scheme. The soap brand chosen to be used by the subjects to wash all areas of the body was Natural, Clear Olive Oil Soap from Life of the Party (North Brunswick, N.J., USA).

TABLE 21

| Human Compounds | Animal Fat Base 1 | Animal Fat Base 2 | Olive Oil Base 1 | Olive Oil Base 2 |
|---|---|---|---|---|
| Hexanal | X | X | | |
| Heptanal | X | | | |
| α-Pinene | X | X | | |
| Benzaldehyde | X | | | |
| Hexanoic acid | X | | | |
| Benzene, 1-methyl-2-(1-methylethyl | X | | | |
| D-Limonene | X | | | |
| Benzyl Alcohol | X | | | |
| 1,6-Octadien-3-ol, 3,7-dimethyl- | X | | | |
| Phenylethyl Alcohol | X | X | | |
| Acetic acid, phenylmethyl ester | X | X | | |

TABLE 21-continued

| Human Compounds | Animal Fat Base 1 | Animal Fat Base 2 | Olive Oil Base 1 | Olive Oil Base 2 |
|---|---|---|---|---|
| Octanoic Acid | X | | | |
| Dodecane | | X | | |
| 6-Octen-1-ol, 3,7-dimethyl-, (R)- | X | | | |
| Camphene | | | X | |
| Tetradecane | | | X | |
| Pentadecane | X | | | |
| Lilial | X | | | |
| Heptadecane | X | | | |

Determination of the Optimal Extraction Time for Armpit and Hand Odor Samples

All gauze used was DUKAL brand, 100% cotton, sterile, 2×2, 8 ply, gauze sponges (DUKAL Corporation, Syosset, N.Y., USA), treated with the SFE method described above and analyzed by SPME-GC/MS prior to use to ensure analytical cleanliness. The soap used was Natural, Clear Olive Oil Soap from Life of the Party (North Brunswick, N.J., USA). The vials used to hold the gauze were 10 mL glass, clear, screw top vials with PTFE/Silicone septa (SUPELCO, Bellefonte, Pa., USA). The extraction solvent used was supercritical grade carbon dioxide (Air Products, Allentown, Pa., USA).

Armpit Sampling Procedure: A male subject (Male 6) and a female subject (Female 2) were required to use olive oil soap and directed to shower at least twice using the provided soap during the 48 hr period prior to sampling. The subjects were also instructed to discontinue the use of deodorants, lotions, and perfumes for at least 48 hrs before sampling to minimize the influence of "tertiary odors." No attempt was made to control the diet of the subjects. Each subject exercised outdoors for a period of 100 min while wearing a tank top in order to minimize the influence of compounds present due to the influence of clothing. Subjects sampled themselves with a pre-treated 2×2 sterile gauze pad each 20 min for a total of five samples collected for each subject. The subjects were instructed to wipe the armpit area to collect their own sweat, then re-seal the sample back into the 10 ml glass vial. All samples were stored in the 10 mL vials at room temperature, and allowed to sit for approximately 24 hrs prior to extraction. These storage conditions were chosen to simulate the conditions under which odor is collected for canine evaluation purposes, and no attempt was made to control microbial interactions with the substrate because it may make contributions to the overall odor profile.

Hand Sampling Procedure: Five samples each were collected from Male 6 and Female 2 consecutively following a set sampling procedure. Subjects were required to wash hands and forearms using olive oil soap for 30 seconds, rinse with cool water for two minutes, air dry for two minutes, and rub the palms of hands over forearms for five minutes followed by ten minutes of holding gauze between the palms of the hands. Each subject sampled themselves, using a pre-treated 2×2 sterile gauze pad, then re-sealing the sample back into the 10 mL glass vial. All samples were stored in the 10 mL vials at room temperature. The scent samples were allowed to sit for approximately 24 hours prior to extraction.

DVB/CAR/PDMS 50/30 µm fibers (SUPELCO, Bellefonte, Pa., USA) were used to extract the VOCs from the headspace of the vials containing the gauze. During optimization, the odor exposures were performed at room temperature on multiple samples from Male 1 for 3, 6, 12, and 15 hrs for armpit odor and 12, 15, 18, 21, 24 hrs for hand odor. All samples were run using the GC/MS method as described above.

Figure 7:
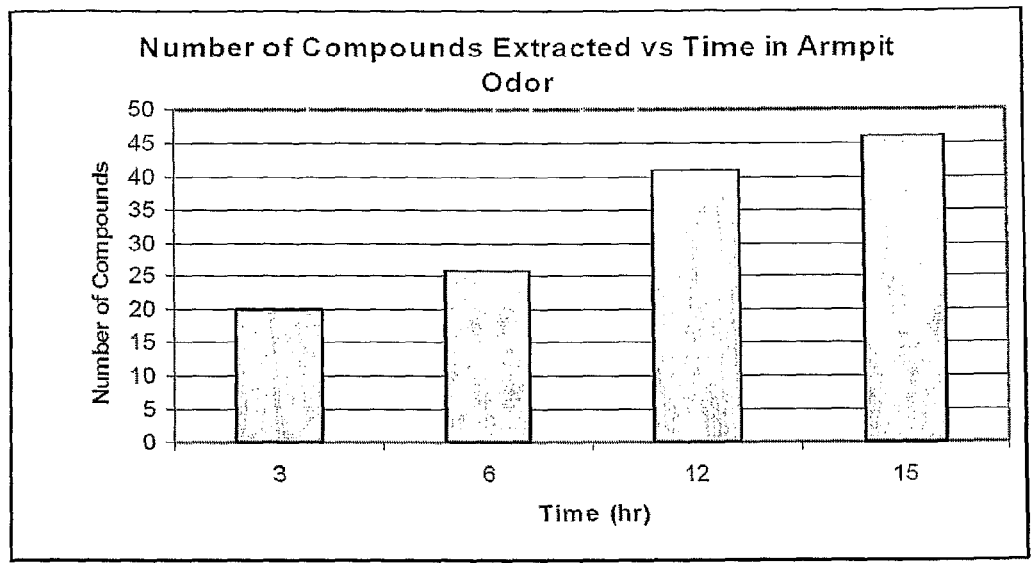
FIG. 7 shows a comparison of the number of compounds extracted at different extraction times from a collection fabric.
Figure 8:
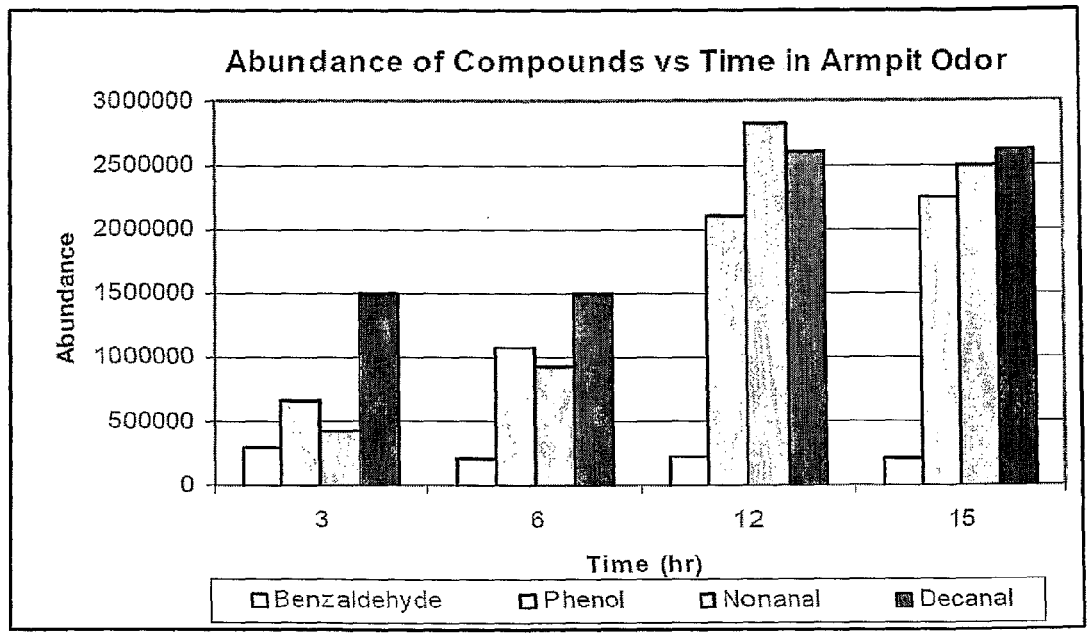
FIG. 8 shows the shows a comparison of the types of compounds and amount of each compound extracted at different extraction times from an armpit odor sample.
Figure 9:
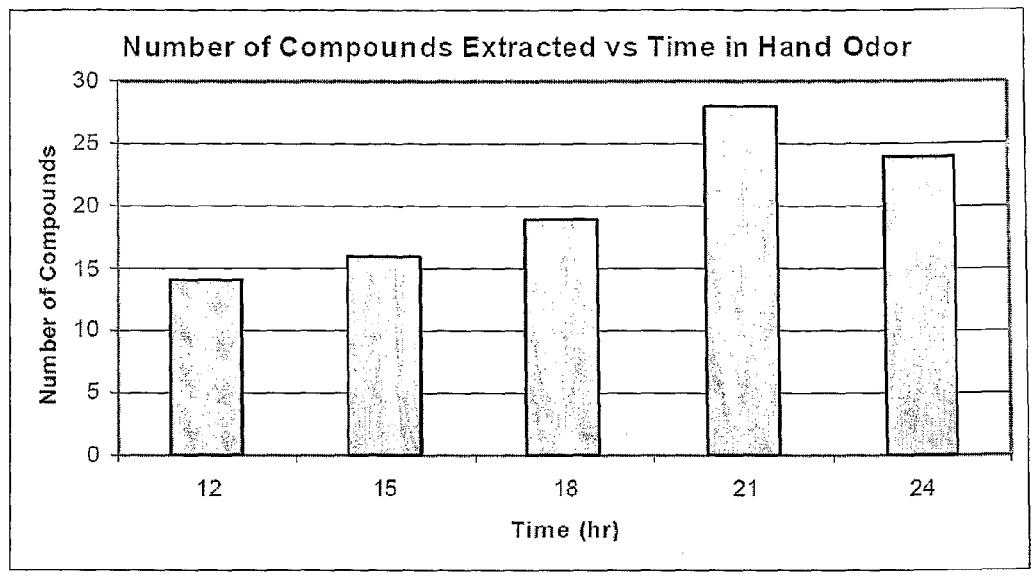
FIG. 9 shows the number of compounds extracted at different extraction times from a hand odor sample.
Figure 10:
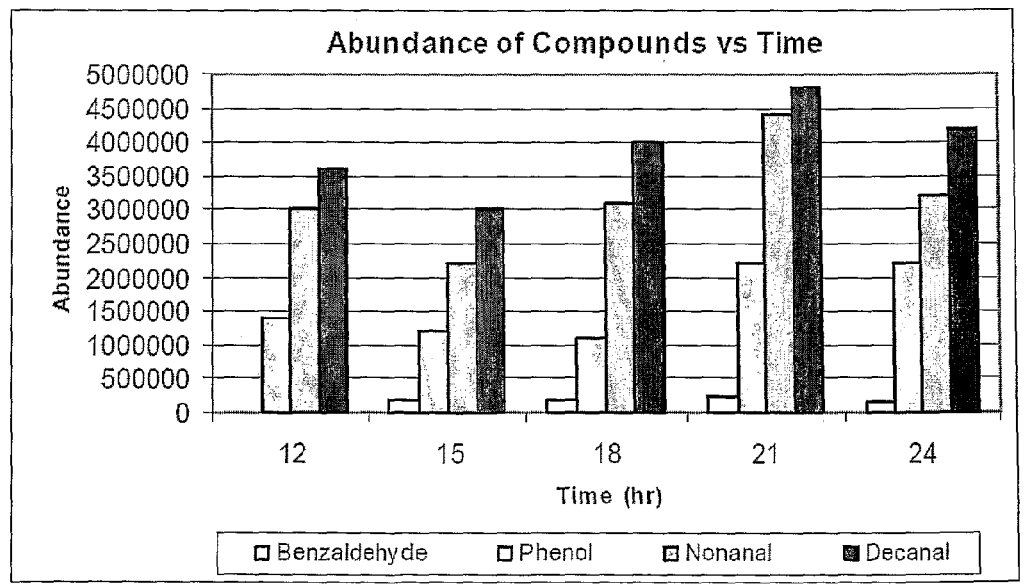
FIG. 10 shows the amount of several compound extracted from a hand odor sample at different extraction times.

The extraction times for the armpit and hand odor samples were evaluated on a combination of the number of human compounds extracted as well as the abundances of four common human compounds: benzaldehyde, phenol, nonanal, and decanal. Fifteen hours was determined to be the optimal extraction time for collected armpit odor through the evaluation parameters stated as shown in FIG. 7 and FIG. 8. Twenty-one hours was determined to be the optimal extraction time for collected hand odor through the evaluation parameters stated as shown in FIG. 9 and FIG. 10.

Evaluation of the Effect of Washing the Hands Prior to Sampling

Gauze pads used were DUKAL brand, 100% cotton, sterile, 2×2, 8 ply, gauze sponges (DUKAL Corporation, Syosset, N.Y., USA), treated prior to use using the SFE method described above, and analyzed by SPME-GC/MS to ensure analytical cleanliness. The vials used to hold the gauze were 10 mL glass, clear, screw top vials with PTFE/Silicone septa (SUPELCO, Bellefonte, Pa., USA). The soap used was Natural, Clear Olive Oil Soap from Life of the Party (North Brunswick, N.J., USA). The extraction solvent for the pre-treatment of the gauze pads by supercritical fluid extraction was supercritical grade carbon dioxide (Air Products, Allentown, Pa., USA). The methanol used as the modifier for the pre-treatment of the gauze pads was HPLC grade (Fisher Scientific, Pittsburgh, Pa., USA).

Six subjects were evaluated, three males and three females ranging in age from 21-28 years old. Each subject was sampled twice. The first sample was collected without washing and the second was collected immediately following the first utilizing the washing sampling procedure. The protocol for the first sampling (which did not include washing) was as follows: a pre-treated 2×2 in. sterile gauze pad was removed from the 10 mL glass vial using tweezers previously rinsed with a 10% bleach solution and placed in the palms of the subject's hands. The subjects then sampled themselves by holding the pre-treated gauze between the palms of their hands, walking outdoors for 10 min, then re-sealing the sample back into the 10 mL glass vial.

The protocol for the second sampling (which included washing) was as follows: 30 seconds of washing the hands and forearms with olive oil based soap, 2 min of rinsing the areas with cool water, 2 min of air drying, and followed by 5 min of rubbing the palms of the hands over the forearms. A pre-treated 2×2 in. sterile gauze pad was then removed from a 10 mL glass vial using tweezers previously rinsed with a 10% bleach solution and placed in the palms of the subject's hands. The subjects then sampled themselves by holding the pre-treated gauze between the palms of their hands, walking outdoors for 10 min, then re-sealing the sample back into the 10 ml glass vial. All samples were stored in the 10 mL vials at room temperature, and allowed to sit for about 24 hrs prior to extraction. These storage conditions were chosen to simulate the conditions under which odor is collected for canine evaluation purposes, and no attempt was made to control microbial interactions with the substrate because it may make contributions to the overall odor profile. The samples were then analyzed using SPME-GC/MS as described above. The fiber used for the SPME Was DVB/CAR on PDMS. Exposures were conducted at room temperature for 21 hrs.

Figure 11:
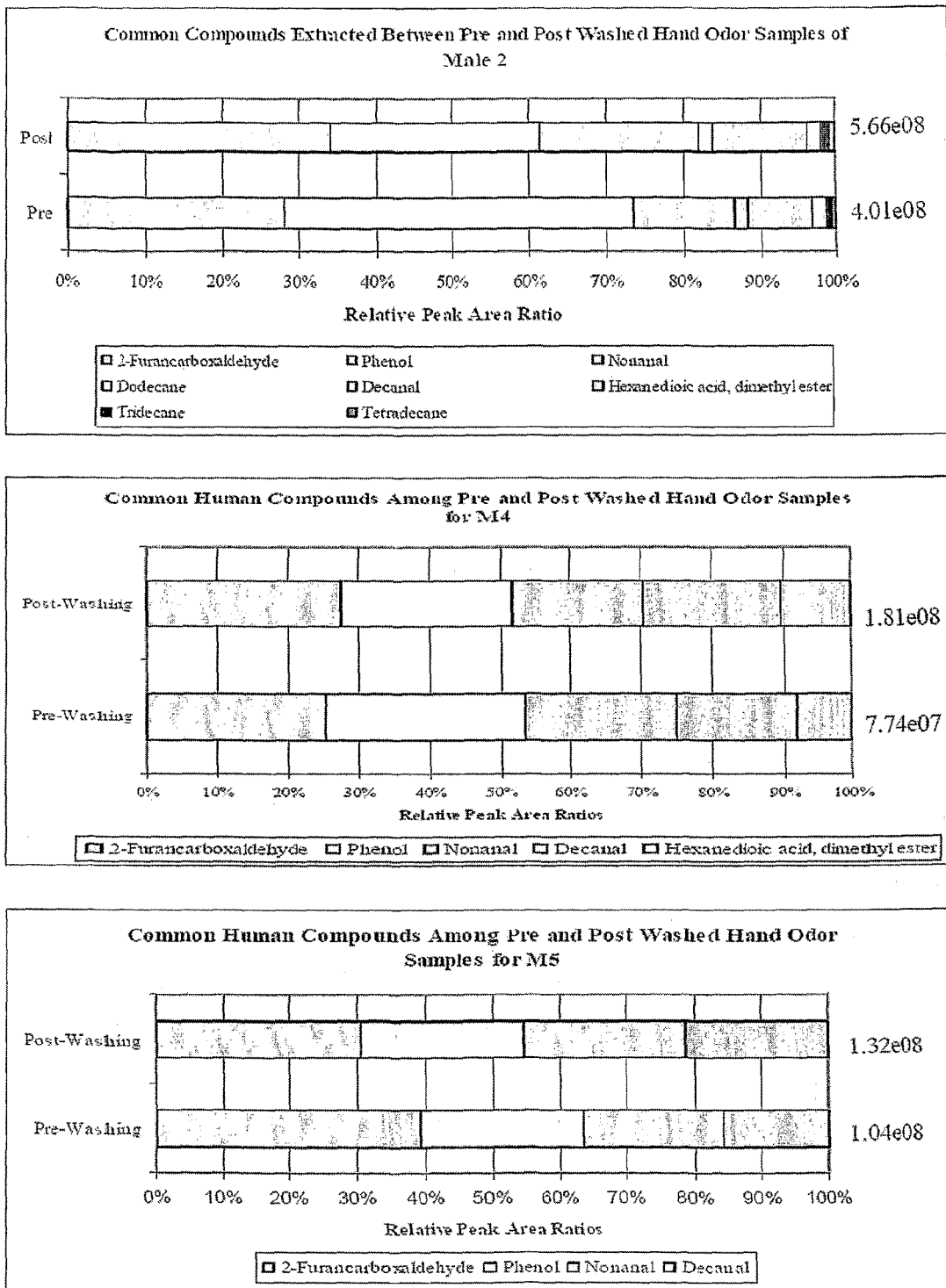
FIG. 11 shows a comparison of three different subjects (M2, M4, and M5) before and after hand washing and the relative amounts of compounds extracted from a hand odor sample.
Figure 12:
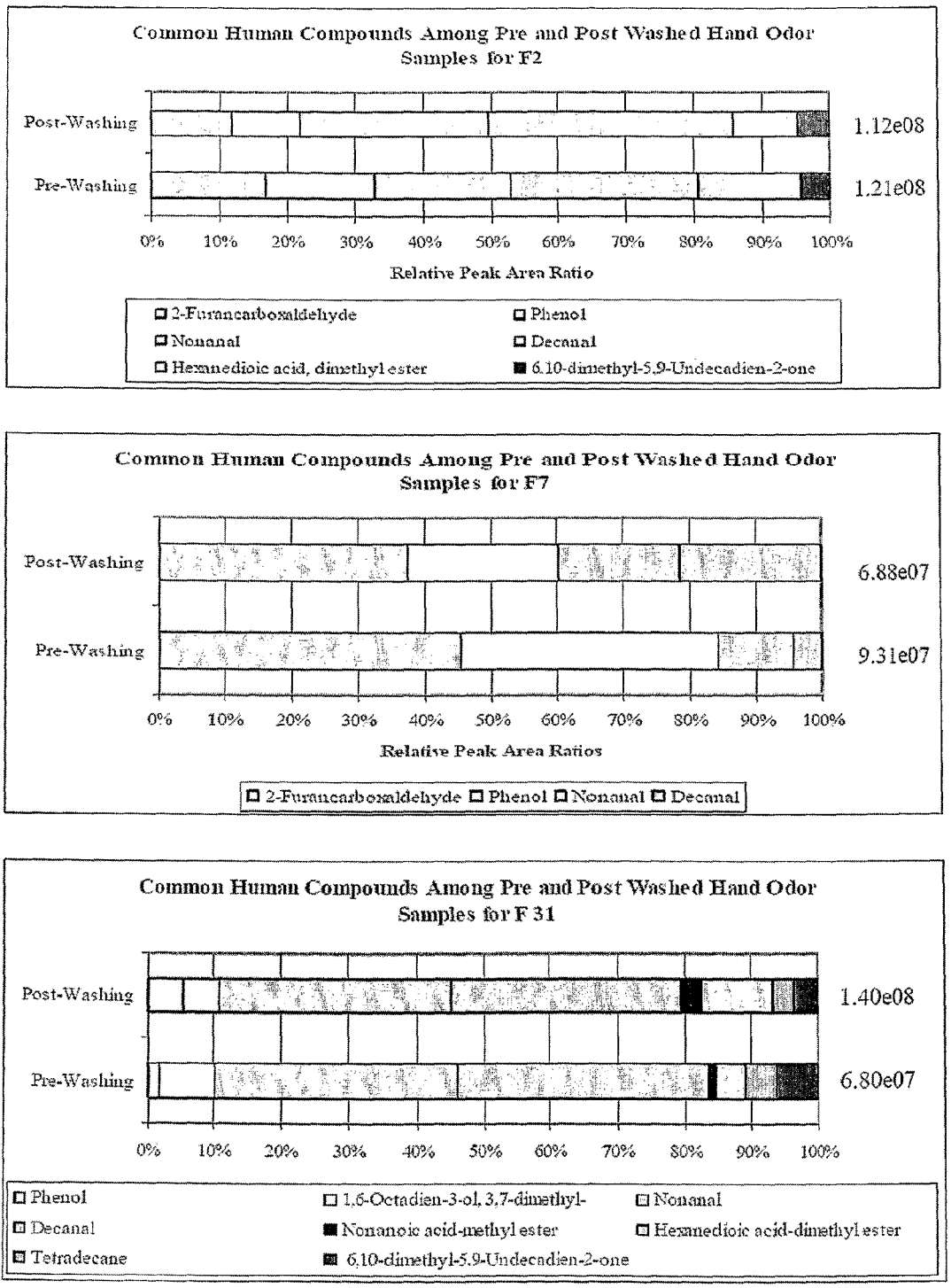
FIG. 12 shows a comparison of three different subjects (F2, F7, and F31) before and after hand washing and the relative amounts of compounds extracted from a hand odor sample.

Table 22 lists the human compounds extracted in pre and post-washed hand odor samples. Four compounds (2-furancarboxaldehye, phenol, nonanal, and decanal) were present in all six of the individual's odor profiles regardless of washing status. A greater number of extraneous compounds were extracted in the pre-washed samples than in the post-washed samples. More human odor compounds were extracted for five of the six subjects in post-washed samples, which may be due to a masking effect by the higher presence of non-human compounds in the pre-washed samples. FIG. 11 and FIG. 12 display the relative ratios of the common human compounds extracted for the male and female subjects between the pre and post-washed samples, respectively. The presence of the extraneous compounds also has an effect on the ratio profiles obtained for each individual. The total peak area for the human compounds extracted does not vary by more than an order of magnitude between the pre and post-washed samples, demonstrating that the washing process is not eliminating a considerable amount of the volatile components. These results demonstrate the need for washing the hands prior to sampling to remove the presence of non-human compounds in the collected samples. Secondary cell transfer can occur from normal interaction with the environment. Washing the hands prior to sampling also reduces the possibility of the influence of cell transfer from other people into a single individual's collected scent sample.

Pa., USA). The methanol used as the modifier for the pre-treatment of the gauze pads was HPLC grade (Fisher Scientific, Pittsburgh, Pa., USA).

Armpit Sampling: Three unrelated male subjects were evaluated: M4, M2, and M5. Subjects were required to use the olive oil soap, and directed to shower at least twice using the provided soap during the 48 hr period prior to sampling. The subjects were also instructed to discontinue the use of deodorants, lotions, and perfumes for at least 48 hrs before sampling to minimize the influence of "tertiary odors." No attempt was made to control the diet of the subjects being sampled. Each subject exercised outdoors for a period of 30 min while wearing a tank top in order to minimize the influence of compounds present due to the influence of clothing. Subjects sampled themselves with a pre-treated 2×2 sterile gauze pad. The subjects were instructed to wipe the armpit area to collect their own sweat. then re-seal the sample back into the 10 mL glass vial. All samples were stored in the 10 mL vials at room temperature, and allowed to sit for approximately 24 hrs prior to extraction. These storage conditions were chosen to simulate the conditions under which odor is collected for canine evaluation purposes, and no attempt was made to control microbial interactions with the substrate because it may make

TABLE 22

| Compound Name | M2 | | M4 | | M5 | | F2 | | F7 | | F31 | |
|---|---|---|---|---|---|---|---|---|---|---|---|---|
| | \multicolumn{12}{c}{Washing Status} | | | | | | | | | | | |
| | Pre | Post | Pre | Post | Pre | Post | Pre | Post | Pre | Post | Pre | Post |
| Butanoic acid | X | | | | | | | | | | | X |
| 2-Furancarboxaldehyde | X | X | X | X | X | X | X | X | X | X | | X |
| Phenol | X | X | X | X | X | X | X | X | X | X | X | X |
| 1,6-Octadien-3-ol, 3,7-dimethyl- | X | | | | | | | | | | X | X |
| Nonanal | X | X | X | X | X | X | X | X | X | X | X | X |
| Octanoic acid, methyl ester | X | | X | | | | X | | | | X | |
| Octanoic Acid | | | | | | | | | | | X | |
| Decane | | | | | | | | | | | | X |
| Dodecane | | X | X | | X | | X | | X | | | |
| Decanal | X | X | X | X | X | X | X | X | X | X | X | X |
| Nonanoic acid-methyl ester | | | | X | | | | X | | | X | X |
| Hexanedioic acid-dimethyl ester | X | X | X | X | | X | X | X | | X | X | X |
| Tridecane | | X | | | | | | X | X | | | |
| Eicosane | | X | | X | | | | X | | | | |
| Tetradecane | X | X | X | | | | | X | | X | X | X |
| 6,10-dimethyl-5,9-undecadien-2-one | | | | | | | X | X | | | X | X |
| Dodecanoic acid-methyl ester | X | | | | | | | | | | | |
| Tridecanoic acid-methyl ester | X | | | | | | | | | | | |
| Tetradecanoic acid-methyl Ester | X | | | | | | | | | | | |
| Total Number of Human Compounds | 13 | 9 | 7 | 8 | 4 | 6 | 8 | 10 | 4 | 8 | 10 | 11 |
| Total Number of Other Compounds | 13 | 11 | 4 | 2 | 9 | 4 | 4 | 3 | 3 | 5 | 8 | 5 |

Evaluation of Odor Profiles of Individuals Over Time

Gauze pads used were DUKAL brand, 100% cotton, sterile, 2×2, 8 ply, gauze sponges (DUKAL Corporation, Syosset, N.Y., USA), treated prior to use with the SFE method described above, and analyzed by SPME-GC/MS to ensure analytical cleanliness. The vials used to hold the gauze were 10 mL glass, clear, screw top vials with PTFE/Silicone septa (SUPELCO, Bellefonte, Pa., USA). The soap used was Natural, Clear Olive Oil Soap from Life of the Party (North Brunswick, N.J., USA). The extraction solvent for the pre-treatment of the gauze pads by supercritical fluid extraction was supercritical grade carbon dioxide (Air Products, Allentown, contributions to the overall odor profile. Samples were collected on a weekly interval and the average climatic conditions present during the samplings included an average temperature of 73° F. and an average humidity of 77%.

Figure 13:
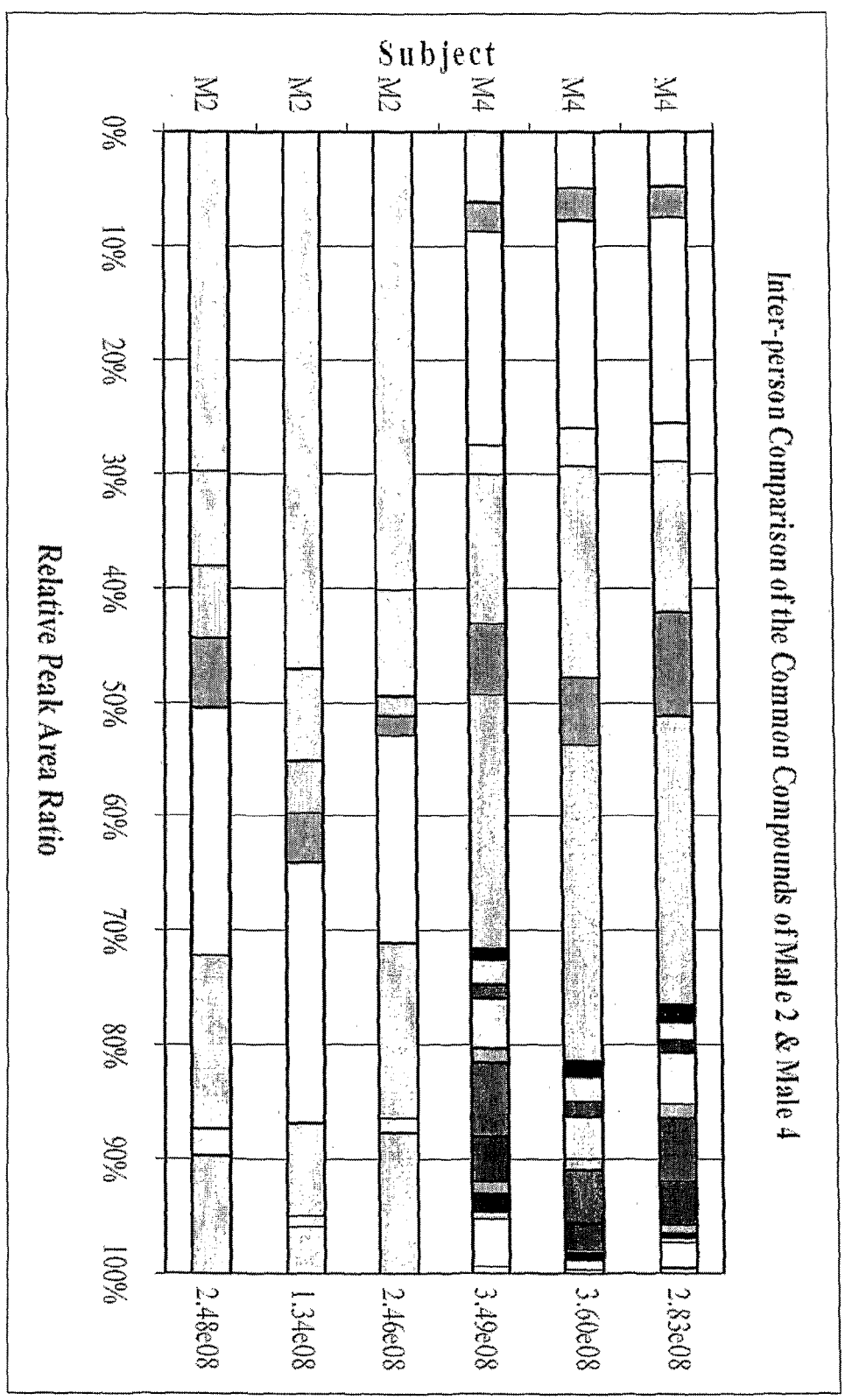
FIG. 13 shows the intra-person variability between three weekly samplings of 2 subjects based on the relative ratios of the peak areas of the twenty-two common compounds extracted in all three samplings of each subject.

Twenty-two human compounds were extracted between three weekly samplings of Male 2 and three weekly samplings of Male 4, as listed in Table 23. Of the twenty-two human compounds extracted between the two individuals, five were common between Male 2 and Male 4, i.e., 2-furanmethanol, furancarboxylic acid-methyl ester, phenol, nonanal, and decanal. The ratio pattern comparison of the common compounds among multiple samplings of an individual can be shown in a semi-quantitative fashion. For human scent to be used as a biometric measurement, it is important to show that the variability between samplings of one individual is not greater than the variability seen among individuals. FIG. 13 shows the intra-person variability between three weekly samplings of Male 2 and Male 4 based on the relative ratios of the peak areas of the twenty-two common compounds extracted in all three samplings of each subject. The relative peak area ratio patterns of the common compounds extracted for the same individual over time demonstrate good reproducibility. FIG. 13 also shows the total peak area for these compounds across the three samplings of Male 2 and Male 4. Male 4 appears to have better reproducibility than Male 2. However, the area values are also more similar. Table 26 displays the correlation coefficients determined between the three weekly samplings of Male 2 and Male 4. Greater con-elation can be seen between the arrays of peak areas for the common compounds sampled for Male 4 than for Male 2. Male 4 also followed exactly the same exercise routine for each of the three samplings, while Male 2 did different activities for the 30 min exercise period across the three samplings. Male 2 shows a greater variability in the total peak area for the common compounds as well as a greater variability among the resulting ratio patterns which may be due to the regiment of exercise. As also seen from Table 26, the peak area arrays for the common human compounds extracted among three weekly samples for an individual have significantly higher correlation ($\geq 0.93$) than when compared between subjects ($\geq 0.45$).

TABLE 23

| Compound Name | M2 | M4 |
|---|---|---|
| 2-Furancarboxaldehyde | X | |
| 2-Furanmethanol | X | X |
| Benzaldehyde | X | |
| Furancarboxylic acid-methyl ester | X | X |
| Phenol | X | X |
| Benzyl Alcohol | | X |
| Nonanal | X | X |
| Nonanol | | X |
| Dodecane | X | |
| Decanal | X | X |
| Nonanoic acid-methyl ester | | X |
| (E)-2-Decenal | | X |
| Tridecane | | X |

TABLE 23-continued

| Compound Name | M2 | M4 |
|---|---|---|
| Undecanal | | X |
| Tetradecane | | X |
| 6,10-dimethyl-5,9-Undecadien-2-one | | X |
| Dodecanoic acid-methyl ester | | X |
| Tetradecanal | | X |
| Tridecanoic acid-methyl ester | | X |
| Heptadecane | | X |
| Tetradecanoic acid-methyl ester | | X |
| Hexadecanoic acid-methyl ester | | X |

TABLE 24

Correlation Coefficient Matrix

| | M2 (W1) | M2 (W2) | M2 (W3) | M4 (W1) | M4 (W2) | M4 (W3) |
|---|---|---|---|---|---|---|
| M2 (W1) | 1 | 0.9347 | 0.9638 | 0.4344 | 0.4509 | 0.4084 |
| M2 (W2) | 0.9347 | 1 | 0.9595 | 0.1690 | 0.1660 | 0.1483 |
| M2 (W3) | 0.9638 | 0.9595 | 1 | 0.3452 | 0.3712 | 0.3299 |
| M4 (W1) | 0.4344 | 0.1690 | 0.3452 | 1 | 0.9746 | 0.9860 |
| M4 (W2) | 0.4509 | 0.1660 | 0.3712 | 0.9746 | 1 | 0.9817 |
| M4 (W3) | 0.4084 | 0.1483 | 0.3299 | 0.9860 | 0.9817 | 1 |

Figure 14:
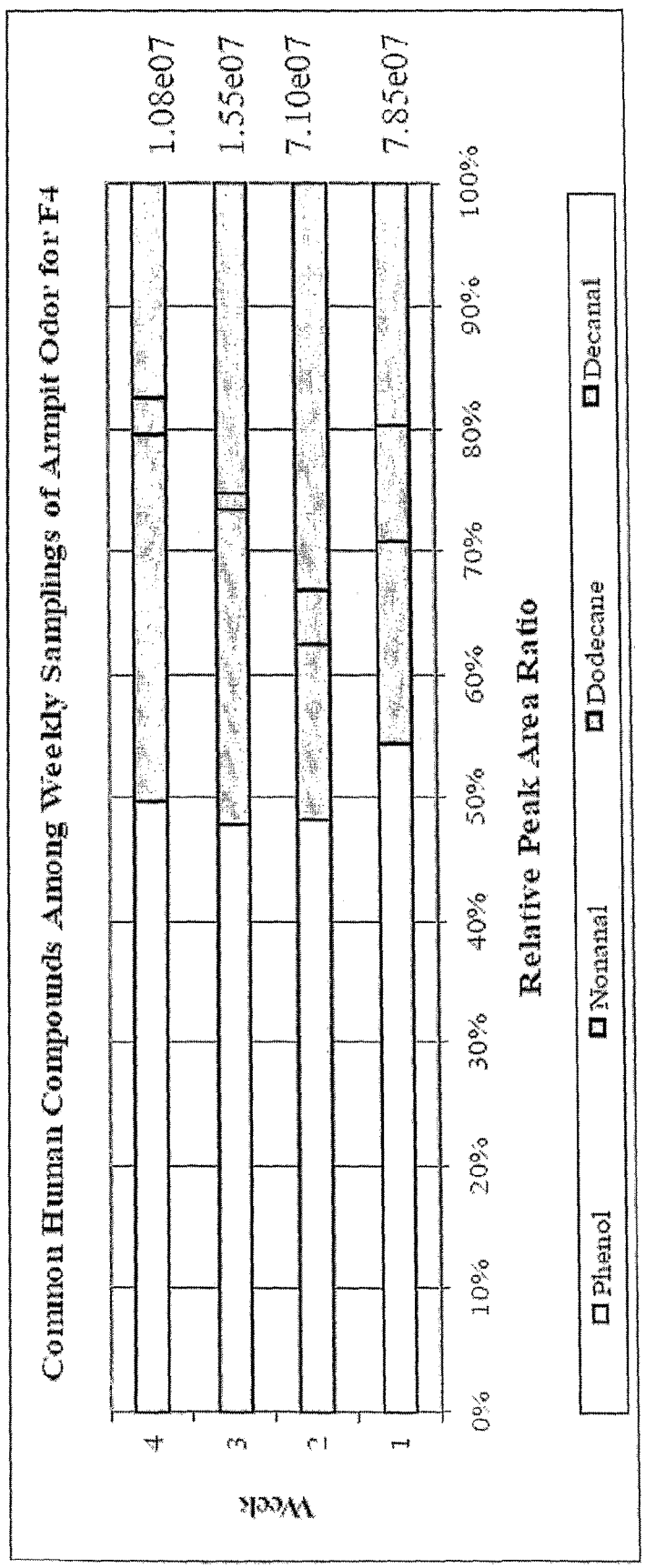
FIGS. 14A, 14B, and 14C shows the variability over time of armpit odor compounds and relative amounts for subjects F4, F5, and F7, respectively.
Figure 14:
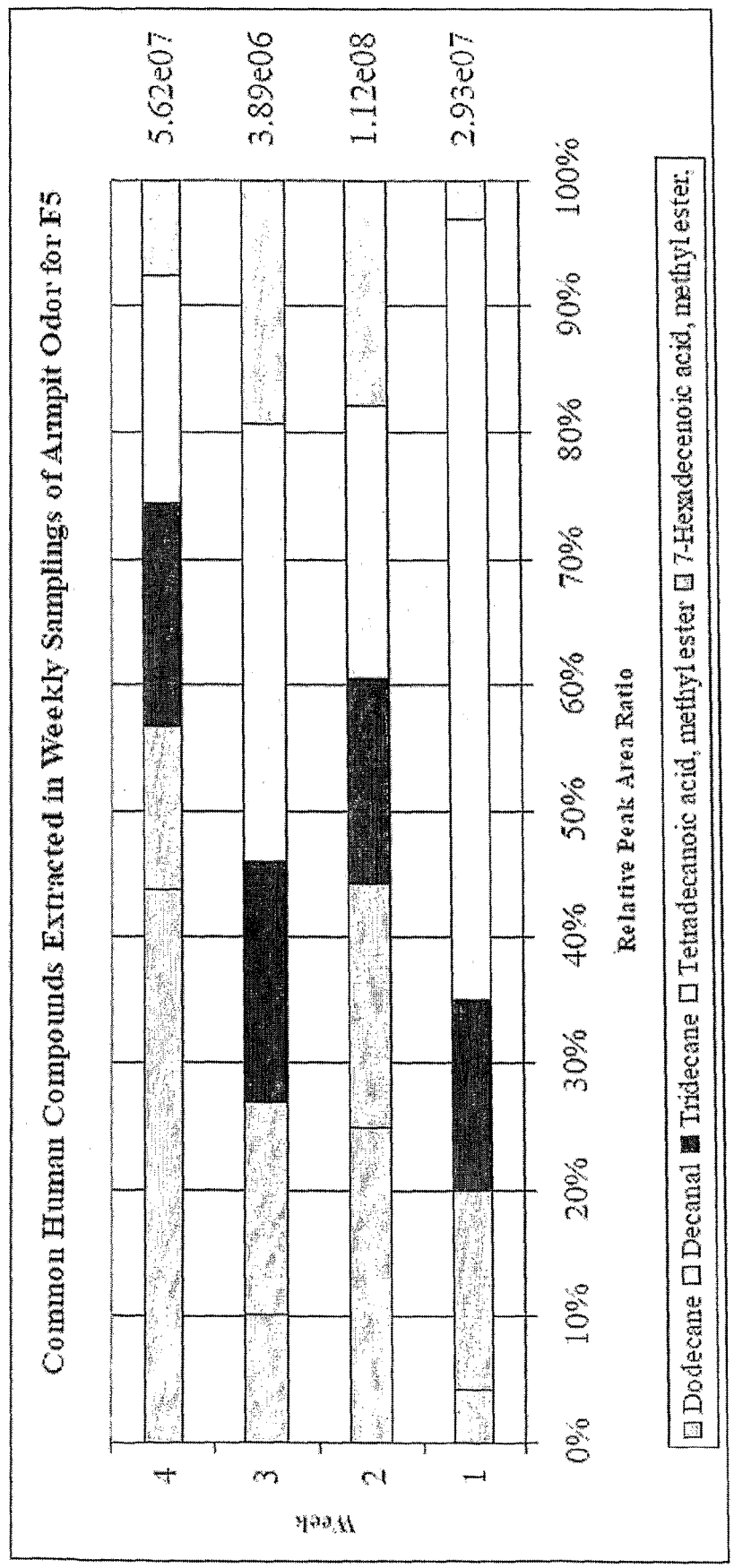
Figure 14:
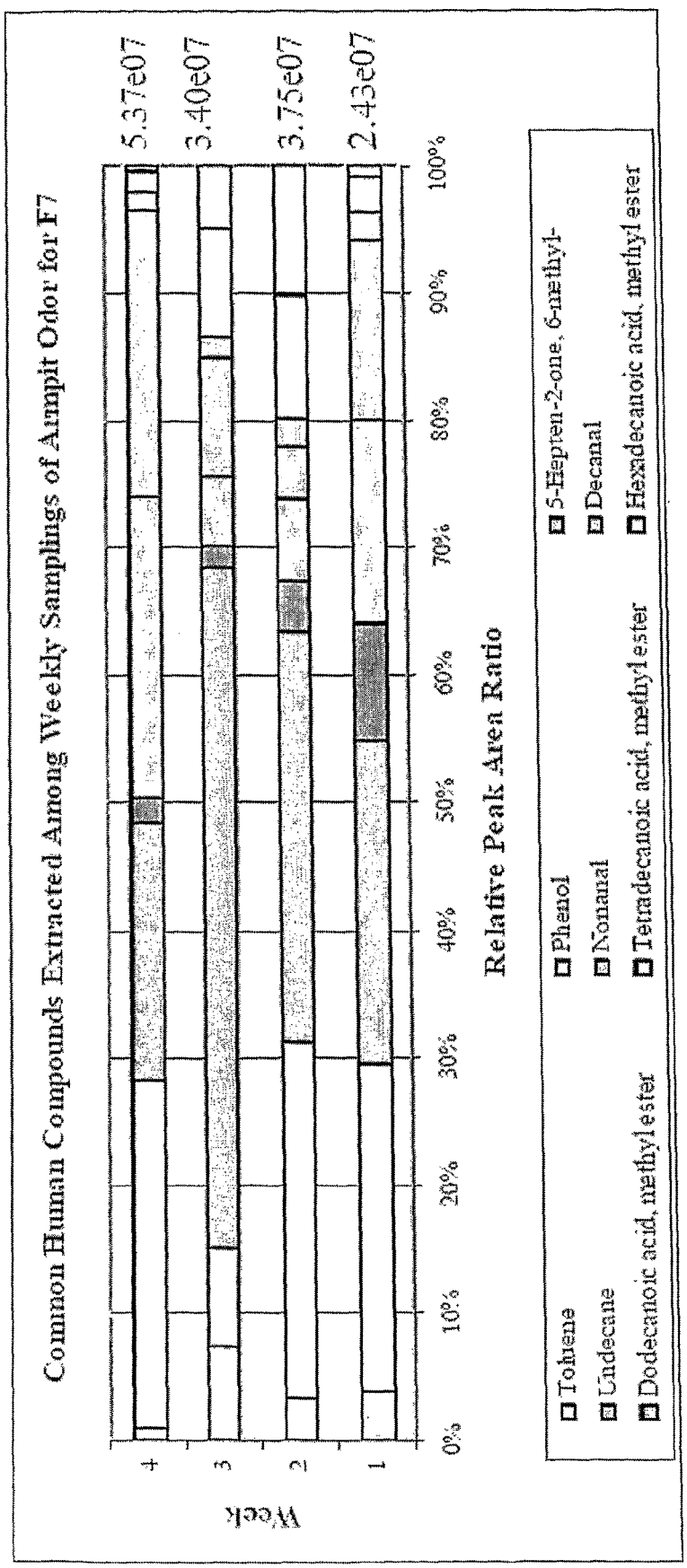

Armpit odor is produced through combinations of eccrine, sebaceous, and apocrine glands. The apocrine gland is influenced by body chemistry including the menstrual cycle of females. Information regarding the menstruation of the female subjects was not collected in accordance with the IRB for human subject research utilized in this study. Table 25 lists the human compounds which were extracted among the weekly samplings of the female subjects. As can be seen from Table 25, the number of common compounds among armpit odor samples for the same subject is low, compared to that of the males. The presence/absence of acids, alkanes, and various aldehydes change from week to week for females. As can be seen in FIGS. 14A, 14B, and 14C, the relative peak area ratios vary more between the women sampled vs. the men, with fewer common compounds seen between samplings for the females studied. The variation seen among the weekly samplings of armpit odor for the female subjects may be a result of the body changes during menstruation.

TABLE 25

| | F4 | | | | F5 | | | | F7 | | | |
|---|---|---|---|---|---|---|---|---|---|---|---|---|
| Compound Name | 1 | 2 | 3 | 4 | 1 | 2 | 3 | 4 | 1 | 2 | 3 | 4 |
| Toluene | X | | X | | X | X | | | X | X | X | X |
| Hexanal | X | | X | | | | | | | | | |
| 2-Furancarboxaldehyde | | | X | X | X | | X | X | X | X | | X |
| 2-Furanmethanol | | | X | X | X | | X | X | X | | | X |
| p-Xylene | X | | | | | X | X | | X | | X | |
| Nonane | | X | | X | | X | X | | X | X | X | |
| Heptanal | X | | | | | | | | X | | X | |
| Hexanoic acid-methyl ester | | X | X | | | X | | X | | X | X | |
| Propanedioic acid-dimethyl ester | | | | | X | X | | | | | | |
| α-Pinene | X | X | | | | X | X | | X | | X | X |
| Furancarboxylic acid-methyl ester | | | X | | | X | | | | | | |
| Phenol | X | X | X | X | X | | X | X | X | X | X | X |
| 6-mthyl-5-Hepten-2-one | X | | X | | | | | X | X | X | X | X |
| Decane | | | | | | X | | | | | | |
| Undecane | X | X | | | | X | | | X | X | X | X |
| Nonanal | X | X | X | X | X | | X | X | X | X | X | X |
| Phenylethyl Alcohol | | | | | | X | | | | | | |
| Octanoic acid-methyl ester | | X | X | | X | | X | X | X | X | | X |

TABLE 25-continued

| Compound Name | F4 1 | F4 2 | F4 3 | F4 4 | F5 1 | F5 2 | F5 3 | F5 4 | F7 1 | F7 2 | F7 3 | F7 4 |
|---|---|---|---|---|---|---|---|---|---|---|---|---|
| 2-Nonenal, (E)- | | | X | | | | | X | | | | X |
| Nonane, 1-chloro- | | | X | | | | | | | | | |
| Acetic acid-phenylmethyl ester | | | | | X | | X | | | | | |
| Napthalene | | | | | | | | X | X | | | X |
| Dodecane | X | X | X | X | X | X | X | X | X | | | X |
| Decanal | X | X | X | X | X | X | X | X | X | X | X | X |
| Nonanoic acid-methyl ester | | | X | X | | X | X | X | | | | X |
| Hexanedioic acid-dimethyl ester | | | X | | X | | | X | | | | |
| Eicosane | | | X | | | | | X | | | | X |
| Tridecane | X | | | | X | X | X | X | X | | | X |
| Undecanal | | | | | X | | | X | | | | X |
| Decanoic acid-methyl ester | | X | | | X | | X | X | | | | |
| Tetradecane | | X | X | | X | | X | X | X | | | X |
| Undecanoic acid-methyl ester | | | | | X | | X | | | | | |
| 6,10-dimethyl-5,9-undecadien-2-one | | X | | | X | | | X | | | | X |
| 9-Octadecenoic acid-methyl ester | | | | | | X | | | | | | |
| Dodecanoic acid-methyl ester | X | | X | | X | | X | X | X | X | X | X |
| Dodecanoic acid | X | | | | X | | X | X | | | | |
| Hexadecane | | | | | X | | X | | X | | | X |
| Tridecanoic acid-methyl ester | | | X | | X | | X | | | | | |
| Heptadecane | | | | | X | | | | X | | | X |
| Tetradecanoic acid-methyl ester | X | X | X | | X | X | X | | X | X | X | X |
| Methyl 9-methyltetradecanoate | | | | | X | X | X | | | X | | |
| Tetradecanoic acid, 12-methyl-, methyl ester | | | X | | | | | | | | | |
| Oleic Acid | | | | | X | | X | | | | | |
| Pentadecanoic acid-methyl ester | X | | X | | X | | X | | | | X | |
| 14-methyl-Pentadecanoic acid-methyl ester | | | | | | X | | | | | | |
| 7-Hexadecenoic acid-methyl ester | X | | X | | X | X | X | X | | | X | |
| Hexadecanoic acid-methyl ester | X | X | X | | X | | X | X | X | X | X | X |

Hand Odor Sampling: Six subjects were evaluated intraday, two males and four females ranging in age from 17-28 years old. Two females and one male were evaluated through inter-day sampling. The sampling protocol was as follows: 30 seconds of washing the hands and forearms with olive oil based soap, 2 min of rinsing the areas with cool water, 2 min of air drying, followed by 5 min of rubbing the palms of the hands over the forearms. A pre-treated 2×2 sterile gauze pad was then removed from the 10 mL glass vial using tweezers previously rinsed with a 10% bleach solution and placed in the palms of the subject's hands. The subjects then sampled themselves by holding the pre-treated gauze between the palms of their hands, walking outdoors for 10 min, then re-sealing the sample back into the 10 mL glass vial. All samples were stored in the 10 mL vials at room temperature, and allowed to sit for approximately 24 hrs prior to extraction. These storage conditions were chosen to simulate the conditions under which odor is collected for canine evaluation purposes, and no attempt was made to control microbial interactions with the substrate because it may make contributions to the overall odor profile. Samples were collected both intraday and interday, and the average climatic conditions present during the samplings included an average temperature of 73° F. and an average humidity of 77%.

Six subjects were sampled three times within the same day. The resulting chromatograms were compared in an attempt to discern the primary odor components present. The primary odor of an individual is the portion of the odor that is most likely to be stable over time and is not influenced by external factors. To be considered a primary odor component, a compound must be present in all three of the samplings for that individual and may differ among subjects. The number of these compounds determined to be primary odor components for the subjects studied ranged from five to fifteen, with a total of twenty different compounds among the population. The primary odor components for each subject were then compared among the samplings and a correlation coefficient was determined, which ranged from 0.9119 to 0.9969 among the individuals within the population.

Figure 15:
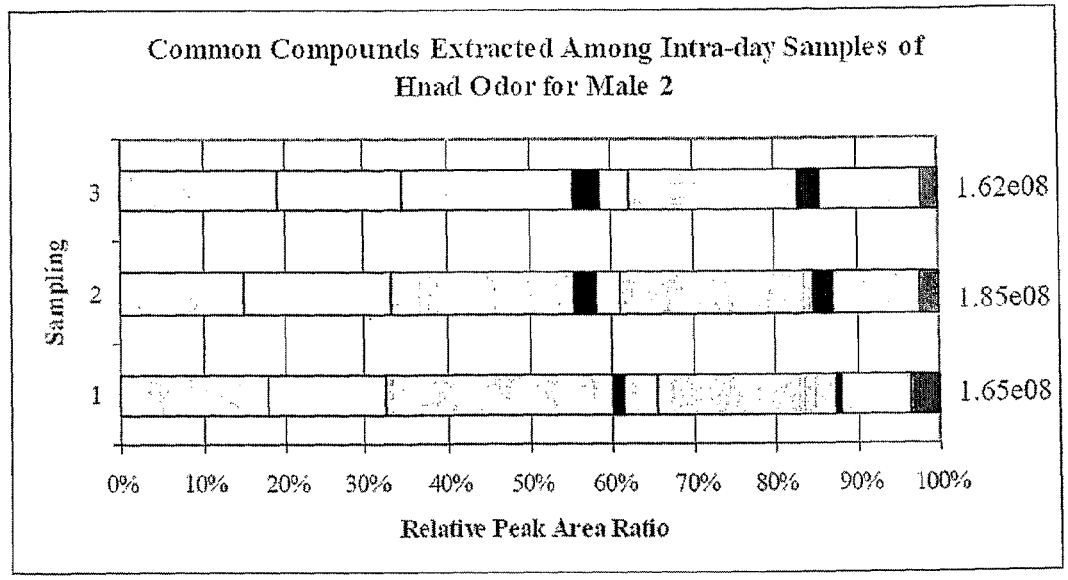
FIG. 15 shows the variation of compounds and relative amounts of sampling of hand odor of subject M2 within the same day.

The compounds identified for Male 2 were 2-furancarboxaldehyde; decanal; phenol; nonanoic acid methyl ester; nonanal; hexanedioic acid-dimethyl ester; octanoic acid-methyl ester; 6,10-dimethyl-5,9-undecadien-2-one; and dodecane. The correlation coefficients for M2 were 0.9581 (between sample 1 and 2); 0.9588 (between sample 1 and 3); and 0.9716 (between sample 2 and 3). These results are also in FIG. 15.

Figure 16:
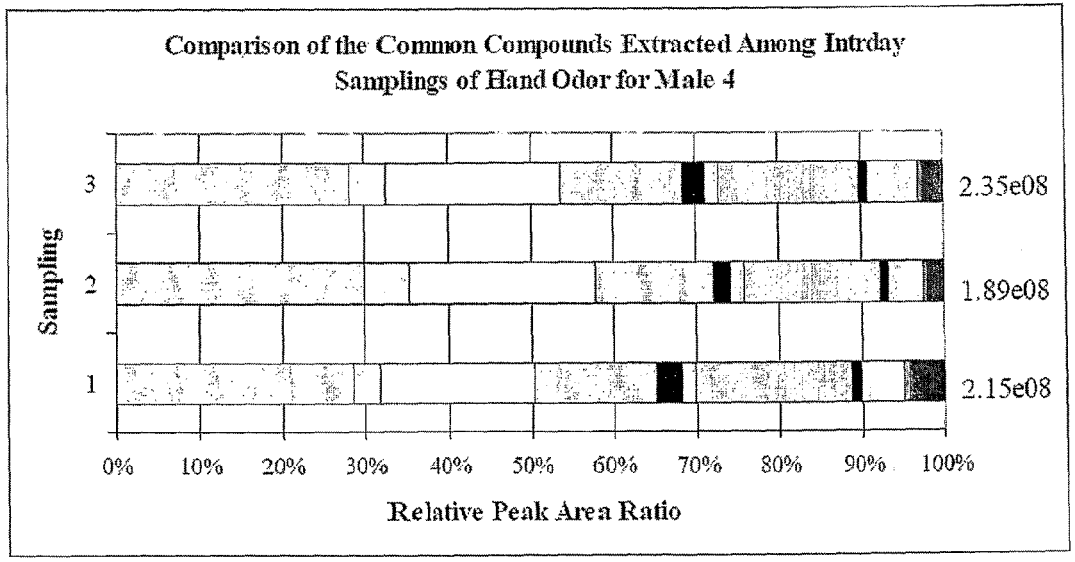
FIG. 16 shows the variation of compounds and relative amounts of sampling of hand odor of subject M4 within the same day.

The compounds identified for Male 4 were 2-furancarboxaldehyde; propanedioic acid-dimethyl ester; phenol; nonanal; octanoic acid-methyl ester; dodecane; decanal; nonanoic acid-methyl ester; hexanedioic acid-dimethyl ester; tetradecane; and 6,10-dimethyl-5,9-undecadien-2-one. The correlation coefficients for M4 were 0.9831 (between sample 1 and 2); 0.9905 (between sample 1 and 3); and 0.9969 (between sample 2 and 3). These results are also in FIG. 16.

Figure 17:
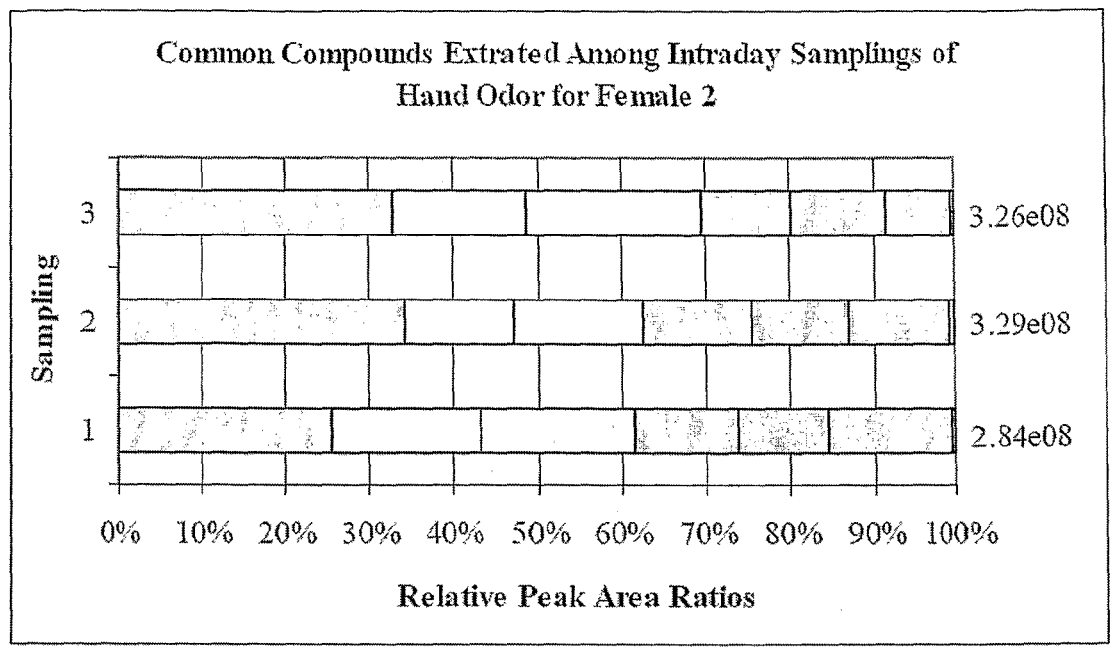
FIG. 17 shows the variation of compounds and relative amounts of sampling of hand odor of subject F2 within the same day.

The compounds identified for Female 2 were 2-furancarboxaldehyde; phenol; benzyl alcohol; nonanal; decanal; hexanedioic acid-dimethyl ester; and tetradecane. The correlation coefficients for F2 were 0.9119 (between sample 1 and 2); 0.9210 (between sample 1 and 3); and 0.9507 (between sample 2 and 3). These results are also in FIG. 17.

Figure 18:
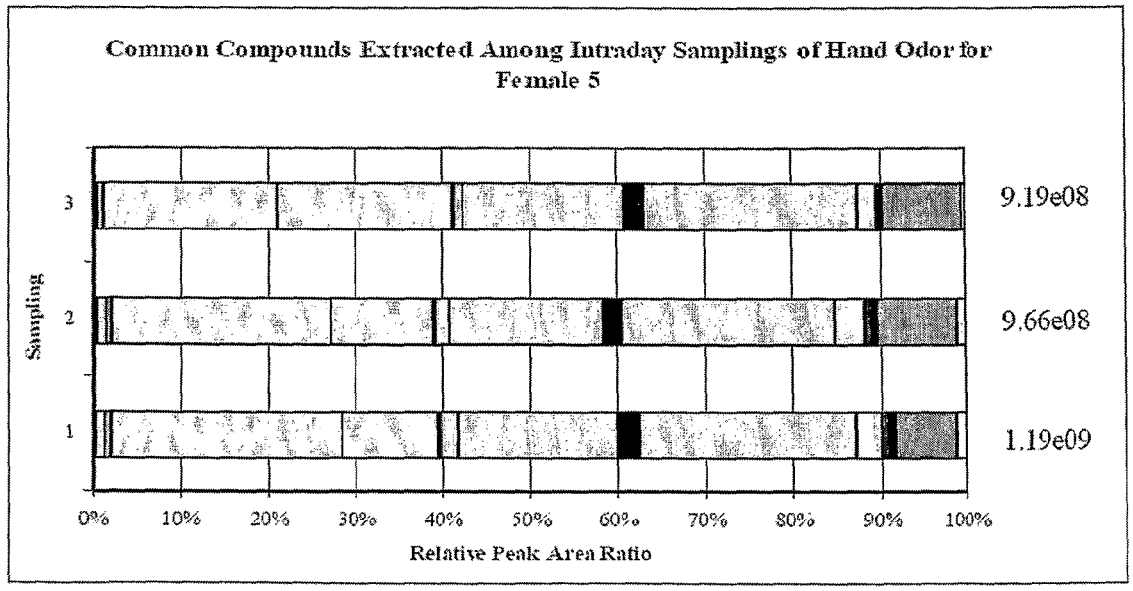
FIG. 18 shows the variation of compounds and relative amounts of sampling of hand odor of subject F5 within the same day.

The compounds identified for Female 5 were pyridine; 2-methyl-2-butenal; butanoic acid; 2-furancarboxaldehyde; 2-furanmethanol; nonane; benzaldehyde; nonanal; (E)-2-nonenal; decanal; hexanedioic acid-dimethyl ester; tridecane; tetradecane; 6,10-dimethyl-5,9-undecadien-2-one; and dodecanoic acid. The correlation coefficients for F5 were 0.9967 (between sample 1 and 2); 0.9438 (between sample 1 and 3); and 0.9569 (between sample 2 and 3). These results are also in FIG. 18.

Figure 19:
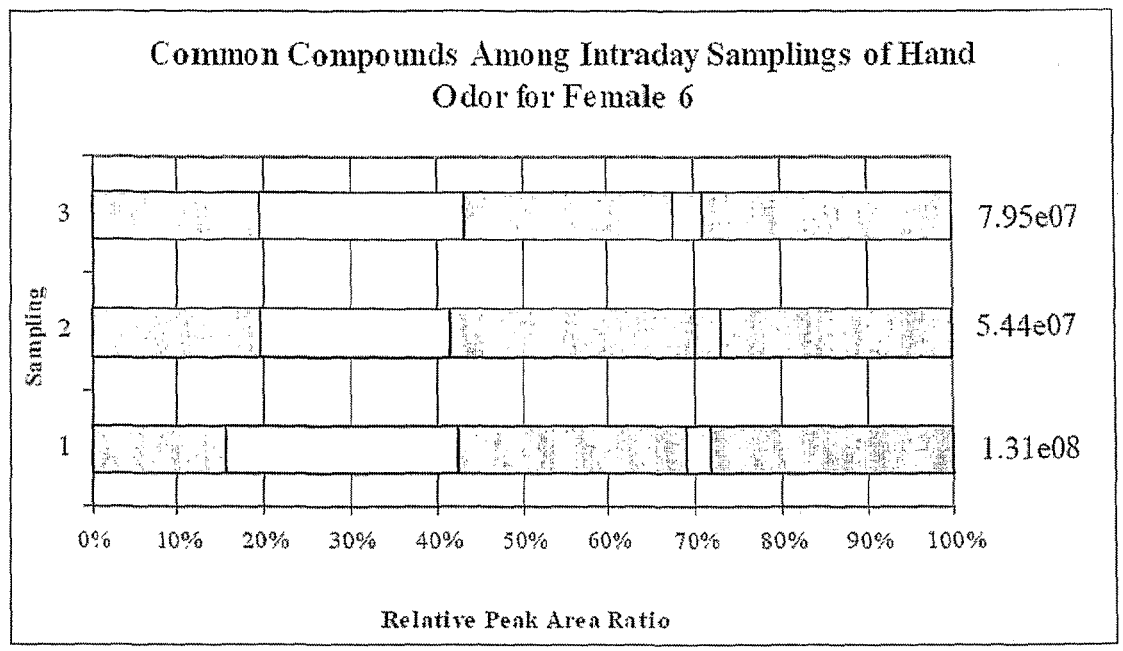
FIG. 19 shows the variation of compounds and relative amounts of sampling of hand odor of subject F6 within the same day.

The compounds identified for Female 6 were 2-furancarboxaldehyde; phenol; benzyl alcohol; nonanal; decanal; hexanedioic acid-dimethyl ester; and tetradecane. The correlation coefficients for F6 were 0.9426 (between sample 1 and 2); 0.9669 (between sample 1 and 3); and 0.9679 (between sample 2 and 3). These results are also in FIG. 19.

Figure 20:
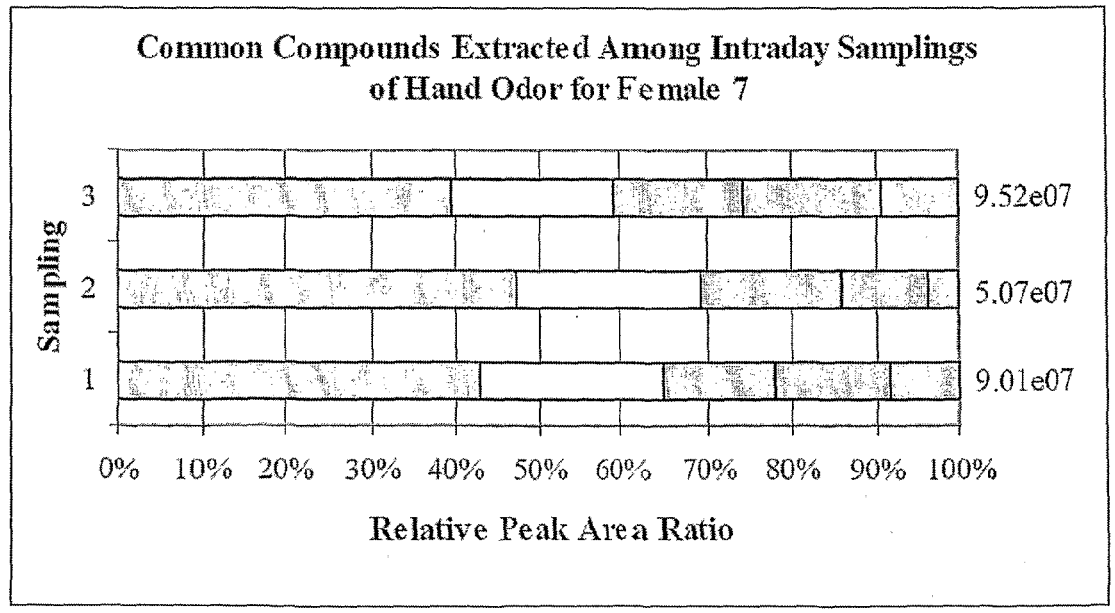
FIG. 20 shows the variation of compounds and relative amounts of sampling of hand odor of subject F7 within the same day.

The compounds identified for Female 7 were 2-furancarboxaldehyde; phenol; nonanal; decanal; and hexanedioic acid-dimethyl ester. The correlation coefficients for F7 were 0.9859 (between sample 1 and 2); 0.9925 (between sample 1 and 3); and 0.9808 (between sample 2 and 3). These results are also in FIG. 20.

Figure 21:
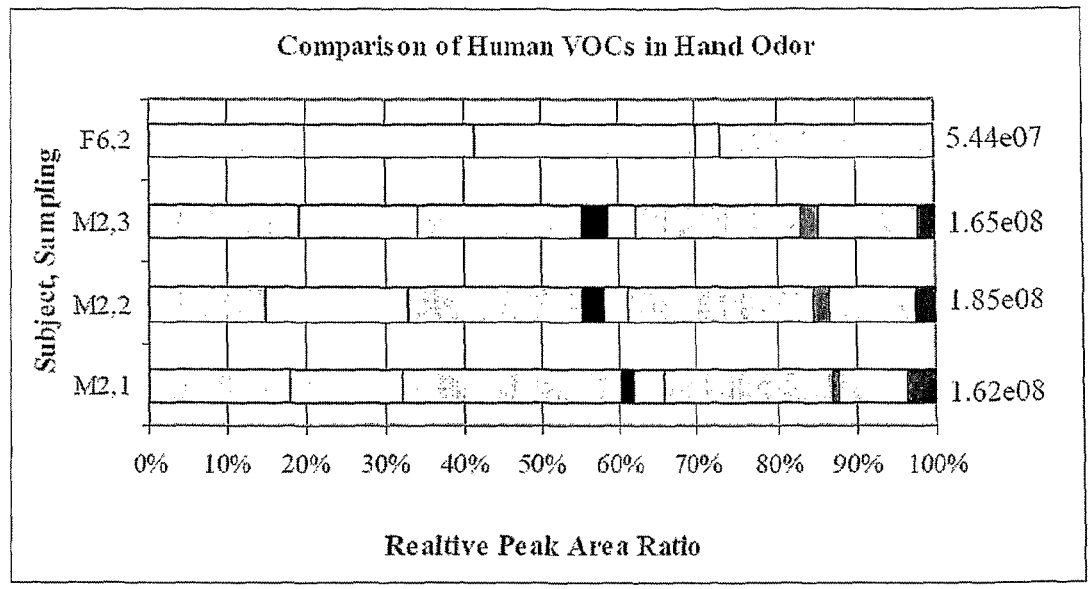
FIG. 21 shows a comparison of relative amounts and compounds of hand odor samples from two subjects M2 and F6.
Figure 22:
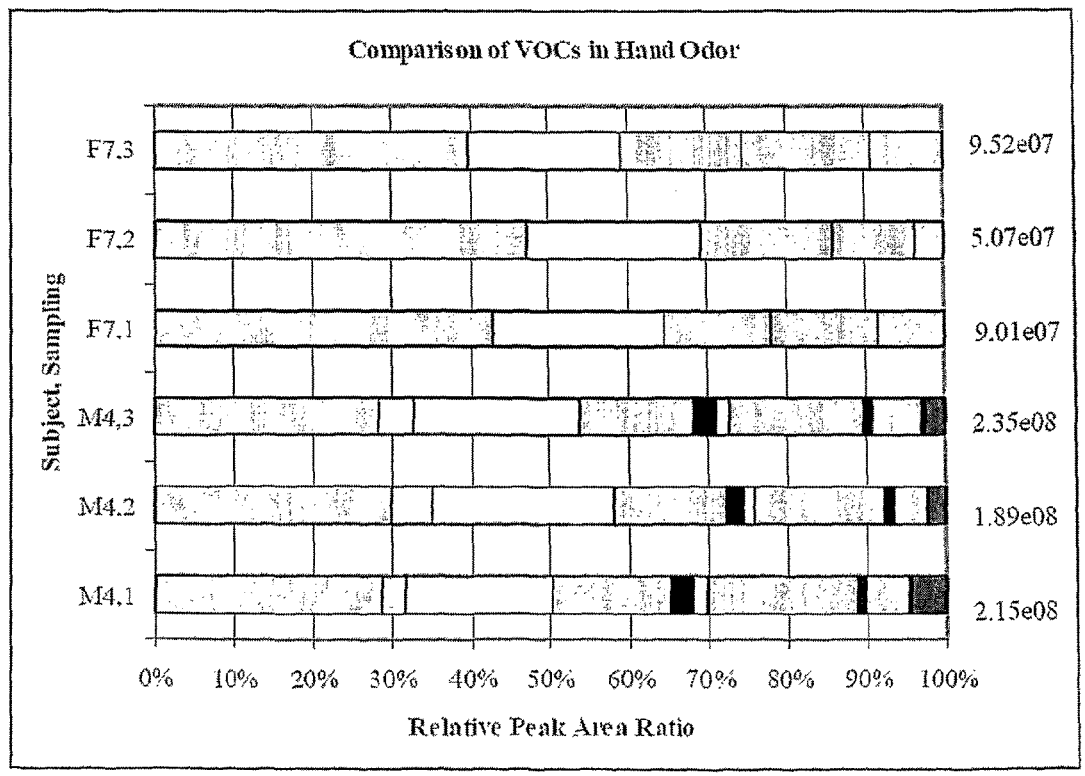
FIG. 22 shows a comparison of relative amounts and compounds of hand odor samples from two subjects M4 and F7.

A searchable library was created using the primary odor components determined among the multiple samplings of each subject. Each sampling for each subject was then searched against the library to determine both the linear and Spearman Rank correlation of each subject to the population using an in-house created automated Excel macro program. The results of these comparisons can be seen in Table 26 and Table 27, where the correlations of each search are listed in descending order. Each subject correlated the highest to the intraday samples collected from themselves, using a match/no-match threshold of 0.90, each subject can be differentiated from the others in the library. However, Male 2 sampling 2 has a high linear correlation to Female 6 sampling 2, when considering the ratio patterns of the primary odor components as seen in FIG. 21, these subjects visually differ in the number and relative amounts of the VOCs present in their primary odor. The multiple samplings of Male 4 also correlates linearly to the multiple samplings of Female 7, yet, when considering the ratio patterns of the primary odor components as seen in FIG. 22 and Table 28, these subjects visually differ in the number and relative amounts of the VOCs present in their primary odor.

TABLE 26

| M2, 1 | | M2, 2 | | M2, 3 | |
|---|---|---|---|---|---|
| M2, 1 | 1 | M2, 2 | 1 | M2, 3 | 1 |
| M2, 2 | 0.9566 | M2, 3 | 0.9580 | M2, 2 | 0.9580 |
| M2, 3 | 0.9535 | M2, 1 | 0.9566 | M2, 1 | 0.9535 |
| F6, 2 | 0.8895 | F6, 2 | 0.9031 | F6, 2 | 0.8109 |
| F6, 3 | 0.8506 | F6, 1 | 0.8966 | F6, 3 | 0.7942 |
| F6, 1 | 0.8407 | F6, 3 | 0.8957 | F6, 1 | 0.7704 |
| F5, 1 | 0.7480 | M4, 1 | 0.7658 | M4, 1 | 0.7567 |
| M4, 1 | 0.7459 | M4, 3 | 0.7534 | M4, 3 | 0.7416 |
| F5, 2 | 0.7348 | M4, 2 | 0.7230 | F7, 3 | 0.7226 |
| M4, 3 | 0.7229 | F5, 1 | 0.6970 | M4, 2 | 0.7138 |
| M4, 2 | 0.6962 | F5, 2 | 0.6845 | F5, 1 | 0.7102 |
| F7, 3 | 0.6615 | F7, 3 | 0.6672 | F5, 2 | 0.6950 |
| F5, 3 | 0.6582 | F5, 3 | 0.6124 | F7, 1 | 0.6666 |
| F7, 1 | 0.5970 | F7, 1 | 0.6007 | F7, 2 | 0.6326 |
| F7, 2 | 0.5906 | F2, 4 | 0.5933 | F2, 4 | 0.6183 |
| F2, 4 | 0.5851 | F7, 2 | 0.5586 | F5, 3 | 0.6026 |
| F2, 2 | 0.4909 | F2, 1 | 0.4737 | F2, 2 | 0.5328 |
| F2, 1 | 0.4444 | F2, 2 | 0.4724 | F2, 1 | 0.4863 |
| F2, 3 | 0.3915 | F2, 3 | 0.3825 | F2, 3 | 0.4210 |

| M4, 1 | | M4, 2 | | M4, 3 | |
|---|---|---|---|---|---|
| M4, 1 | 1 | M4, 2 | 1 | M4, 3 | 1 |
| M4, 3 | 0.9905 | M4, 3 | 0.9969 | M4, 2 | 0.9969 |
| M4, 2 | 0.9831 | M4, 1 | 0.9831 | M4, 1 | 0.9905 |
| F7, 3 | 0.9678 | F7, 3 | 0.9608 | F7, 3 | 0.9685 |
| F7, 1 | 0.9510 | F7, 1 | 0.9579 | F7, 1 | 0.9585 |
| F7, 2 | 0.9319 | F7, 2 | 0.9460 | F7, 2 | 0.9394 |
| F6, 3 | 0.8664 | F6, 3 | 0.8409 | F6, 3 | 0.8560 |

TABLE 26-continued

| | | | | | |
|---|---|---|---|---|---|
| F6, 2 | 0.8548 | F2, 4 | 0.8316 | F2, 4 | 0.8432 |
| F2, 4 | 0.8414 | F6, 2 | 0.8248 | F6, 2 | 0.8420 |
| F6, 1 | 0.8106 | F2, 2 | 0.7959 | F6, 1 | 0.8099 |
| F2, 2 | 0.8019 | F6, 1 | 0.7955 | F2, 2 | 0.8010 |
| F5, 1 | 0.7861 | F2, 3 | 0.7526 | M2, 2 | 0.7534 |
| F5, 2 | 0.7709 | F2, 1 | 0.7327 | F2, 3 | 0.7459 |
| M2, 2 | 0.7658 | M2, 2 | 0.7230 | M2, 3 | 0.7416 |
| M2, 3 | 0.7567 | M2, 3 | 0.7138 | F2, 1 | 0.7399 |
| M2, 1 | 0.7459 | F5, 1 | 0.7073 | F5, 1 | 0.7278 |
| F2, 3 | 0.7414 | M2, 1 | 0.6962 | M2, 1 | 0.7229 |
| F2, 1 | 0.7201 | F5, 2 | 0.6880 | F5, 2 | 0.7098 |
| F5, 3 | 0.6486 | F5, 3 | 0.5683 | F5, 3 | 0.5896 |

| F2, 1 | | F2, 2 | | F2, 3 | |
|---|---|---|---|---|---|
| F2, 1 | 1 | F2, 2 | 1 | F2, 3 | 1 |
| F2, 4 | 0.9269 | F2, 4 | 0.9745 | F2, 2 | 0.9507 |
| F2, 3 | 0.9210 | F2, 3 | 0.9507 | F2, 1 | 0.9210 |
| F2, 2 | 0.9119 | F2, 1 | 0.9119 | F2, 4 | 0.9171 |
| M4, 3 | 0.7399 | F7, 2 | 0.8515 | F7, 2 | 0.7635 |
| M4, 2 | 0.7327 | F7, 1 | 0.8504 | M4, 2 | 0.7526 |
| M4, 1 | 0.7201 | F7, 3 | 0.8356 | F7, 1 | 0.7463 |
| F7, 1 | 0.7101 | M4, 1 | 0.8019 | M4, 3 | 0.7459 |
| F7, 2 | 0.6954 | M4, 3 | 0.8010 | M4, 1 | 0.7414 |
| F7, 3 | 0.6849 | M4, 2 | 0.7959 | F7, 3 | 0.7130 |
| F5, 1 | 0.5106 | F5, 1 | 0.6518 | F5, 1 | 0.5707 |
| F5, 2 | 0.4927 | F5, 2 | 0.6305 | F5, 2 | 0.5483 |
| M2, 3 | 0.4863 | M2, 3 | 0.5328 | M2, 3 | 0.4210 |
| M2, 2 | 0.4737 | M2, 1 | 0.4909 | F5, 3 | 0.4115 |
| M2, 1 | 0.4444 | F5, 3 | 0.4818 | M2, 1 | 0.3915 |
| F5, 3 | 0.3669 | M2, 2 | 0.4724 | M2, 2 | 0.3825 |
| F6, 2 | 0.3576 | F6, 2 | 0.4090 | F6, 3 | 0.3566 |
| F6, 3 | 0.3548 | F6, 3 | 0.3952 | F6, 2 | 0.3557 |
| F6, 1 | 0.3138 | F6, 1 | 0.3062 | F6, 1 | 0.2807 |

| F5, 1 | | F5, 2 | | F5, 3 | |
|---|---|---|---|---|---|
| F5, 1 | 1 | F5, 2 | 1 | F5, 3 | 1 |
| F5, 2 | 0.9967 | F5, 1 | 0.9967 | F5, 2 | 0.9568 |
| F5, 3 | 0.9438 | F5, 3 | 0.9568 | F5, 1 | 0.9438 |
| M4, 1 | 0.7861 | M4, 1 | 0.7709 | M2, 1 | 0.6582 |
| M2, 1 | 0.7480 | M2, 1 | 0.7348 | F6, 2 | 0.6575 |
| F6, 2 | 0.7450 | F6, 2 | 0.7248 | M4, 1 | 0.6486 |
| F7, 3 | 0.7435 | F7, 3 | 0.7200 | F6, 3 | 0.6388 |
| M2, 3 | 0.7278 | M4, 3 | 0.7098 | M2, 2 | 0.6124 |
| F6, 3 | 0.7264 | F6, 3 | 0.7066 | M2, 3 | 0.6026 |
| M2, 3 | 0.7102 | M2, 3 | 0.6950 | M4, 3 | 0.5896 |
| M4, 2 | 0.7073 | M4, 2 | 0.6880 | F6, 1 | 0.5846 |
| M2, 2 | 0.6970 | M2, 2 | 0.6845 | F7, 3 | 0.5711 |
| F7, 1 | 0.6957 | F7, 1 | 0.6718 | M4, 2 | 0.5683 |
| F7, 2 | 0.6855 | F7, 2 | 0.6598 | F7, 1 | 0.5201 |
| F2, 4 | 0.6663 | F2, 4 | 0.6463 | F7, 2 | 0.5106 |
| F6, 1 | 0.6532 | F6, 1 | 0.6354 | F2, 4 | 0.5091 |
| F2, 2 | 0.6518 | F2, 2 | 0.6305 | F2, 2 | 0.4818 |
| F2, 3 | 0.5707 | F2, 3 | 0.5483 | F2, 3 | 0.4115 |
| F2, 1 | 0.5106 | F2, 1 | 0.4927 | F2, 1 | 0.3669 |

| F6, 1 | | F6, 2 | | F6, 3 | |
|---|---|---|---|---|---|
| F6, 1 | 1 | F6, 2 | 1 | F6, 3 | 1 |
| F6, 3 | 0.9664 | F6, 3 | 0.9679 | F6, 2 | 0.9679 |
| F6, 2 | 0.9425 | F6, 1 | 0.9425 | F6, 1 | 0.9664 |
| M2, 2 | 0.8966 | M2, 2 | 0.9031 | M2, 2 | 0.8957 |
| M2, 1 | 0.8407 | M2, 1 | 0.8895 | M4, 1 | 0.8664 |
| M4, 1 | 0.8106 | M4, 1 | 0.8548 | M4, 3 | 0.8560 |
| M4, 3 | 0.8099 | M4, 3 | 0.8420 | M2, 1 | 0.8506 |
| M4, 2 | 0.7955 | M4, 2 | 0.8248 | M4, 2 | 0.8409 |
| M2, 3 | 0.7704 | M2, 3 | 0.8109 | M2, 3 | 0.7942 |
| F5, 1 | 0.6532 | F5, 1 | 0.7450 | F5, 1 | 0.7264 |
| F5, 2 | 0.6354 | F5, 2 | 0.7248 | F5, 2 | 0.7066 |
| F5, 3 | 0.5846 | F5, 3 | 0.6575 | F5, 3 | 0.6388 |
| F2, 4 | 0.4617 | F2, 4 | 0.5416 | F2, 4 | 0.5327 |
| F7, 3 | 0.4039 | F7, 3 | 0.5180 | F7, 3 | 0.5197 |
| F7, 2 | 0.3616 | F7, 2 | 0.4800 | F7, 2 | 0.4682 |
| F7, 1 | 0.3470 | F7, 1 | 0.4508 | F7, 1 | 0.4587 |
| F2, 1 | 0.3138 | F2, 2 | 0.4090 | F2, 2 | 0.3952 |
| F2, 2 | 0.3062 | F2, 1 | 0.3576 | F2, 3 | 0.3566 |
| F2, 3 | 0.2807 | F2, 3 | 0.3557 | F2, 1 | 0.3548 |

TABLE 26-continued

| F7, 1 | | F7, 2 | | F7, 3 | |
|---|---|---|---|---|---|
| F7, 1 | 1 | F7, 2 | 1 | F7, 3 | 1 |
| F7, 3 | 0.9925 | F7, 1 | 0.9859 | F7, 1 | 0.9925 |
| F7, 2 | 0.9859 | F7, 3 | 0.9808 | F7, 2 | 0.9808 |
| M4, 3 | 0.9585 | M4, 2 | 0.9460 | M4, 3 | 0.9685 |
| M4, 2 | 0.9579 | M4, 3 | 0.9394 | M4, 1 | 0.9678 |
| M4, 1 | 0.9510 | M4, 1 | 0.9319 | M4, 2 | 0.9608 |
| F2, 4 | 0.8762 | F2, 4 | 0.8614 | F2, 4 | 0.8777 |
| F2, 2 | 0.8504 | F2, 2 | 0.8515 | F2, 2 | 0.8356 |
| F2, 3 | 0.7463 | F2, 3 | 0.7635 | F5, 1 | 0.7435 |
| F2, 1 | 0.7101 | F2, 1 | 0.6954 | M2, 3 | 0.7226 |
| F5, 1 | 0.6957 | F5, 1 | 0.6855 | F5, 2 | 0.7200 |
| F5, 2 | 0.6718 | F5, 2 | 0.6598 | F2, 3 | 0.7130 |
| M2, 3 | 0.6666 | M2, 3 | 0.6326 | F2, 1 | 0.6849 |
| M2, 2 | 0.6007 | M2, 1 | 0.5906 | M2, 2 | 0.6672 |
| M2, 1 | 0.5970 | M2, 2 | 0.5586 | M2, 1 | 0.6615 |
| F5, 3 | 0.5201 | F5, 3 | 0.5106 | F5, 3 | 0.5711 |
| F6, 3 | 0.4587 | F6, 2 | 0.4800 | F6, 3 | 0.5197 |
| F6, 2 | 0.4508 | F6, 3 | 0.4682 | F6, 2 | 0.5180 |
| F6, 1 | 0.3470 | F6, 1 | 0.3616 | F6, 1 | 0.4039 |

TABLE 27

| M2, 1 | | M2, 2 | | M2, 3 | |
|---|---|---|---|---|---|
| M2, 1 | 1 | M2, 2 | 1 | M2, 3 | 1 |
| M2, 2 | 0.9636 | M2, 1 | 0.9636 | M2, 1 | 0.9515 |
| M2, 3 | 0.9515 | M2, 3 | 0.9394 | M2, 2 | 0.9394 |
| M4, 1 | 0.6678 | M4, 1 | 0.6608 | M4, 1 | 0.5699 |
| M4, 3 | 0.6119 | M4, 3 | 0.6189 | M4, 3 | 0.5350 |
| M4, 2 | 0.5839 | M4, 2 | 0.5769 | M4, 2 | 0.4860 |
| F5, 2 | 0.4746 | F5, 2 | 0.4307 | F5, 2 | 0.4518 |
| F5, 1 | 0.4746 | F5, 1 | 0.4307 | F5, 1 | 0.4518 |
| F5, 3 | 0.4465 | F5, 3 | 0.4096 | F5, 3 | 0.4254 |
| F2, 3 | 0.1591 | F2, 3 | 0.1409 | F2, 3 | 0.0955 |
| F2, 2 | 0.1318 | F2, 2 | 0.0864 | F2, 2 | 0.0682 |
| F2, 1 | 0.0864 | F2, 1 | 0.0500 | F2, 1 | 0.0227 |
| F6, 2 | −0.1273 | F6, 3 | −0.1152 | F6, 2 | −0.1636 |
| F6, 3 | −0.1394 | F6, 2 | −0.1273 | F6, 3 | −0.1758 |
| F6, 1 | −0.1758 | F6, 1 | −0.1273 | F6, 1 | −0.2242 |
| F7, 2 | −0.2000 | F7, 3 | −0.2121 | F7, 2 | −0.2485 |
| F7, 3 | −0.2121 | F7, 1 | −0.2121 | F7, 3 | −0.2606 |
| F7, 1 | −0.2121 | F7, 2 | −0.2242 | F7, 1 | −0.2606 |

| M4, 1 | | M4, 2 | | M4, 3 | |
|---|---|---|---|---|---|
| M4, 1 | 1 | M4, 2 | 1 | M4, 3 | 1 |
| M4, 3 | 0.9545 | M4, 3 | 0.9818 | M4, 2 | 0.9818 |
| M4, 2 | 0.9364 | M4, 1 | 0.9364 | M4, 1 | 0.9545 |
| M2, 1 | 0.6678 | M2, 1 | 0.5839 | M2, 2 | 0.6189 |
| M2, 2 | 0.6608 | M2, 2 | 0.5769 | M2, 1 | 0.6119 |
| M2, 3 | 0.5699 | M2, 3 | 0.4860 | M2, 3 | 0.5350 |
| F5, 2 | 0.5143 | F5, 2 | 0.4617 | F5, 2 | 0.4602 |
| F5, 1 | 0.5128 | F5, 1 | 0.4602 | F5, 1 | 0.4586 |
| F5, 3 | 0.4722 | F5, 3 | 0.4195 | F5, 3 | 0.4165 |
| F2, 3 | 0.1818 | F2, 3 | 0.1678 | F2, 3 | 0.1748 |
| F2, 2 | 0.1469 | F2, 2 | 0.1399 | F2, 2 | 0.1538 |
| F2, 1 | 0.1399 | F2, 1 | 0.1259 | F2, 1 | 0.1469 |
| F7, 3 | −0.2409 | F7, 3 | −0.2409 | F7, 3 | −0.2318 |
| F7, 1 | −0.2409 | F7, 1 | −0.2409 | F7, 1 | −0.2318 |
| F7, 2 | −0.2591 | F7, 2 | −0.2500 | F7, 2 | −0.2409 |
| F6, 1 | −0.3227 | F6, 1 | −0.3318 | F6, 1 | −0.3318 |
| F6, 3 | −0.3318 | F6, 3 | −0.3500 | F6, 3 | −0.3500 |
| F6, 2 | −0.3500 | F6, 2 | −0.3591 | F6, 2 | −0.3591 |

| F2, 1 | | F2, 2 | | F2, 3 | |
|---|---|---|---|---|---|
| F2, 1 | 1 | F2, 2 | 1 | F2, 3 | 1 |
| F2, 2 | 0.9643 | F2, 1 | 0.9643 | F2, 2 | 0.8929 |
| F2, 3 | 0.8571 | F2, 3 | 0.8929 | F2, 1 | 0.8571 |
| M4, 3 | 0.1469 | M4, 3 | 0.1538 | F7, 3 | 0.1964 |
| M4, 1 | 0.1399 | M4, 1 | 0.1469 | F7, 1 | 0.1964 |
| M4, 2 | 0.1259 | M4, 2 | 0.1399 | M4, 3 | 0.1818 |
| F7, 2 | 0.0893 | F7, 2 | 0.1399 | M4, 1 | 0.1818 |
| M2, 1 | 0.0864 | M2, 1 | 0.1318 | M4, 3 | 0.1748 |

TABLE 27-continued

| F7, 3 | 0.0536 | F7, 3 | 0.0893 | M4, 2 | 0.1678 |
|---|---|---|---|---|---|
| F7, 1 | 0.0536 | F7, 1 | 0.0893 | F7, 2 | 0.1607 |
| M2, 2 | 0.0500 | M2, 2 | 0.0864 | M2, 1 | 0.1591 |
| M2, 3 | 0.0227 | M2, 3 | 0.0682 | M2, 2 | 0.1409 |
| F6, 1 | −0.0595 | F6, 2 | 0.0357 | F6, 3 | 0.1310 |
| F6, 2 | −0.0833 | F6, 1 | 0.0119 | F6, 2 | 0.1071 |
| F6, 3 | −0.1071 | F6, 3 | −0.0119 | M2, 3 | 0.0955 |
| F5, 2 | −0.1446 | F5, 2 | −0.1373 | F5, 2 | −0.1250 |
| F5, 1 | −0.1446 | F5, 1 | −0.1373 | F5, 1 | −0.1250 |
| F5, 3 | −0.1912 | F5, 3 | −0.1838 | F5, 3 | −0.1618 |

| F5, 1 | | F5, 2 | | F5, 3 | |
|---|---|---|---|---|---|
| F5, 1 | 1 | F5, 2 | 1 | F5, 3 | 1 |
| F5, 2 | 0.9929 | F5, 1 | 0.9929 | F5, 2 | 0.9321 |
| F5, 3 | 0.9214 | F5, 3 | 0.9321 | F5, 1 | 0.9214 |
| M4, 1 | 0.5128 | M4, 1 | 0.5143 | M4, 1 | 0.4722 |
| M2, 1 | 0.4746 | M2, 1 | 0.4746 | M2, 1 | 0.4465 |
| M4, 2 | 0.4602 | M4, 2 | 0.4617 | M2, 3 | 0.4254 |
| M4, 3 | 0.4586 | M4, 3 | 0.4602 | M4, 2 | 0.4195 |
| M2, 3 | 0.4518 | M2, 3 | 0.4518 | M4, 3 | 0.4165 |
| M2, 2 | 0.4307 | M2, 2 | 0.4307 | M2, 2 | 0.4096 |
| F2, 3 | −0.1250 | F2, 3 | −0.1250 | F2, 3 | −0.1618 |
| F2, 2 | −0.1373 | F2, 2 | −0.1373 | F2, 2 | −0.1838 |
| F2, 1 | −0.1446 | F2, 1 | −0.1446 | F2, 1 | −0.1912 |
| F6, 3 | −0.2145 | F6, 3 | −0.2145 | F6, 3 | −0.2218 |
| F6, 2 | −0.2169 | F6, 2 | −0.2169 | F6, 2 | −0.2292 |
| F6, 1 | −0.2463 | F6, 1 | −0.2463 | F6, 1 | −0.2512 |
| F7, 3 | −0.4544 | F7, 3 | −0.4544 | F7, 3 | −0.4838 |
| F7, 1 | −0.4544 | F7, 1 | −0.4544 | F7, 1 | −0.4838 |
| F7, 2 | −0.4574 | F7, 2 | −0.4574 | F7, 2 | −0.4926 |

| F6, 1 | | F6, 2 | | F6, 3 | |
|---|---|---|---|---|---|
| F6, 1 | 1 | F6, 2 | 1 | F6, 3 | 1 |
| F6, 3 | 0.9000 | F6, 3 | 0.9000 | F6, 2 | 0.9000 |
| F6, 2 | 0.7000 | F6, 1 | 0.7000 | F6, 1 | 0.9000 |
| F7, 3 | 0.5429 | F7, 2 | 0.4286 | F7, 3 | 0.4286 |
| F7, 1 | 0.5429 | F7, 3 | 0.3714 | F7, 1 | 0.4286 |
| F7, 2 | 0.4286 | F7, 1 | 0.3714 | F7, 2 | 0.3714 |
| F2, 3 | 0.1786 | F2, 3 | 0.1071 | F2, 3 | 0.1310 |
| F2, 2 | 0.0119 | F2, 2 | 0.0357 | F2, 2 | −0.0119 |
| F2, 1 | −0.0595 | F2, 1 | −0.0833 | F2, 1 | −0.1071 |
| M2, 2 | −0.1273 | M2, 2 | −0.1273 | M2, 2 | −0.1152 |
| M2, 1 | −0.1758 | M2, 1 | −0.1273 | M2, 1 | −0.1394 |
| M2, 3 | −0.2242 | M2, 3 | −0.1636 | M2, 3 | −0.1758 |
| F5, 2 | −0.2463 | F5, 2 | −0.2169 | F5, 2 | −0.2145 |
| F5, 1 | −0.2463 | F5, 1 | −0.2169 | F5, 1 | −0.2145 |
| F5, 3 | −0.2512 | F5, 3 | −0.2292 | F5, 3 | −0.2218 |
| M4, 1 | −0.3227 | M4, 1 | −0.3500 | M4, 1 | −0.3318 |
| M4, 3 | −0.3318 | M4, 3 | −0.3591 | M4, 3 | −0.3500 |
| M4, 2 | −0.3318 | M4, 2 | −0.3591 | M4, 2 | −0.3500 |

TABLE 28

| Compound Name | M41 | M42 | M43 | F71 | F72 | F73 |
|---|---|---|---|---|---|---|
| 2-Furancarboxaldehyde | X | X | X | X | X | X |
| Propanedioic acid-dimethyl ester | X | X | X | | | |
| Phenol | X | X | X | X | X | X |
| Nonanal | X | X | X | X | X | X |
| Octanoic acid-methyl ester | X | X | X | | | |
| Dodecane | X | X | X | | | |
| Decanal | X | X | X | X | X | X |
| Nonanoic acid-methyl ester | X | X | X | | | |
| Dodecane | X | X | X | | | |
| Decanal | X | X | X | X | X | X |
| Nonanoic acid-methyl ester | X | X | X | | | |
| Hexanedioic acid-dimethyl ester | X | X | X | X | X | X |
| Tetradecane | X | X | X | | | |
| 6,10-dimethyl-5,9-undecadien-2-one | X | X | X | | | |

The VOCs as extracted above in the collected odor samples are difficult to accurately compare in a quantitative fashion. A Spearman Ranking correlation is a semi-quantitative data analysis technique of analyzing non-parametric data sets. Through this method, each primary odor component in each array is assigned an integer ranking based on the size of the peak areas relative to others within the profile. The comparison is based on the pattern of the compounds within a sample with respect to the size of the peak area. The Spearman Ranking Correlation results, as shown in Table 29, present a more accurate representation of the comparison of the compounds determined in the odor profiles. Through this method the ranked correlations among samplings for the same person ranged from 1 to 0.7000. There are no significant correlations between the different subjects studied, but ranged from 0.6678 to −0.4926.

TABLE 29

| Compound Name | M2, 1 | M2, 2 | M2, 3 | F6, 2 |
|---|---|---|---|---|
| 2-Furancarboxaldehyde | X | X | X | X |
| Phenol | X | X | X | X |
| Nonanal | X | X | X | X |
| Octanoic acid-methyl ester | X | X | X | |
| Dodecane | X | X | X | X |
| Decanal | X | X | X | X |
| Nonanoic acid-methyl ester | X | X | X | |
| Hexanedioic acid-dimethyl ester | X | X | X | |
| 6,10-dimethyl-5,9-Undecadien-2-one | X | X | X | | pared. The presence/absence of the primary odor components between subjects must be considered and given the same weight as the common compounds between subjects. Thus, the Spearman Ranking correlation results in a truer representation of the relationships between the samples.

Figure 25:
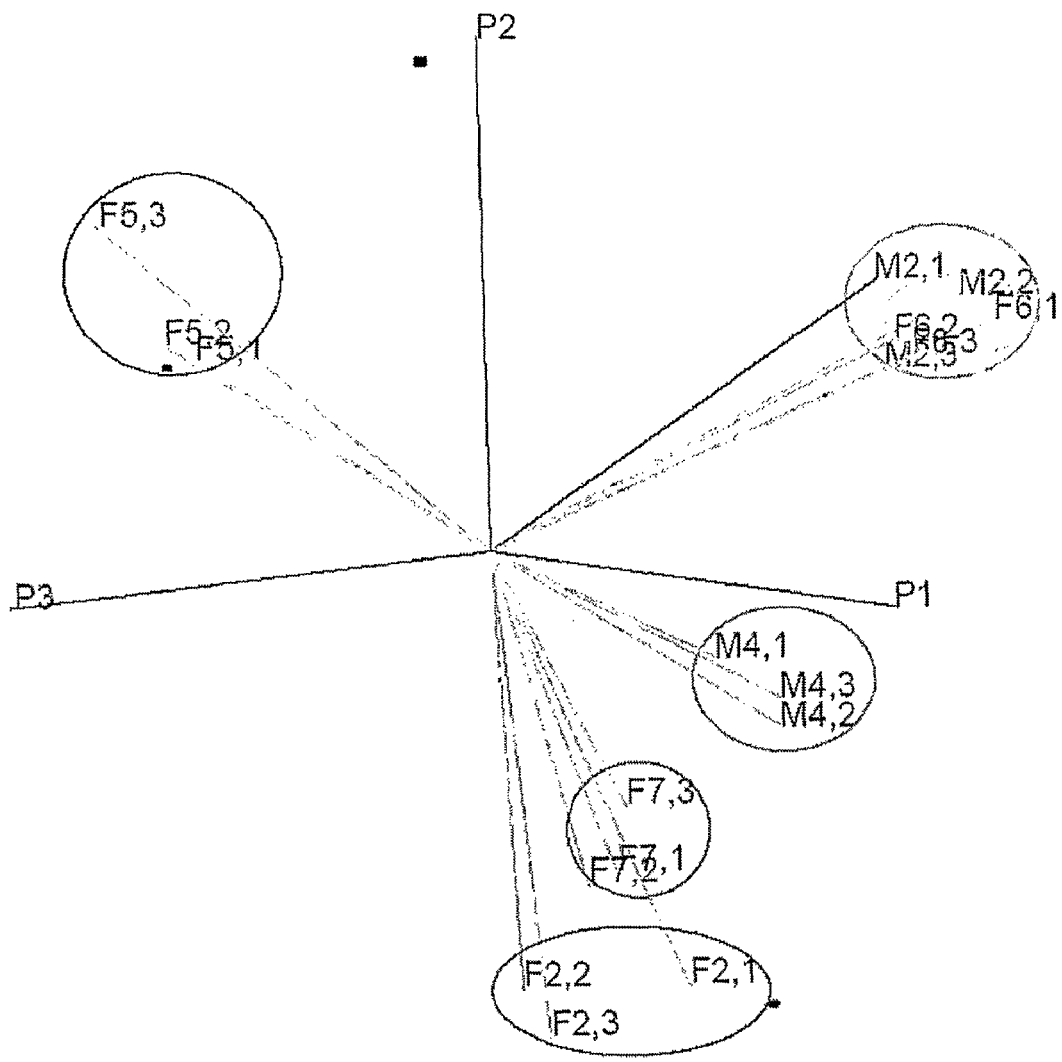
FIG. 25 shows a three-dimensional plot of principle components for various subjects analyzed.

Principle component analysis (PCA) was also conducted on the six subject multiple samplings data set. Table 30 displays a summary of results for PCA of the data set, including the Eigenanlysis of the correlation matrix and the resulting principle components. The analysis resulted in a total of fifteen principle components, of which nine are shown below. Each Eigenvalue gives the amount of variance in the data set which is explained by the principle component. As can be seen from Table 30, the first three principle components account for approximately 94.68% of the total variation, and thus these values were plotted in FIG. 25. Groupings can be noted among the multiple samples collected from the same individual. Female 5's three samplings group together, as well as Male 4, Female 2, and Female 7. The multiple samplings of Female 6 and Male 2 produce overlapping groupings, which is in agreement with the results of the linear correlations. Female 7 and Male 4, however, do not group together, which does not agree with what was determined through linear correlation.

TABLE 30

| Eigenvalue | | | | | | | | |
|---|---|---|---|---|---|---|---|---|
| 14.3074 | 1.6580 | 1.0767 | 0.4878 | 0.3170 | 0.0680 | 0.0371 | 0.0240 | 0.0173 |
| Percent | | | | | | | | |
| 79.4856 | 9.2110 | 5.9816 | 2.7099 | 1.7613 | 0.3779 | 0.2063 | 0.1331 | 0.0959 |
| Cuml. Percent | | | | | | | | |
| 79.4856 | 88.6967 | 94.6782 | 97.3882 | 99.1495 | 99.5274 | 99.7337 | 99.8668 | 99.9628 |
| PC1 | PC2 | PC3 | PC4 | PC5 | PC6 | PC7 | PC8 | PC9 |

| | PC1 | PC2 | PC3 | PC4 | PC5 | PC6 | PC7 | PC8 | PC9 |
|---|---|---|---|---|---|---|---|---|---|
| M2, 1 | 0.2350 | 0.2409 | −0.1946 | 0.2786 | −0.2522 | 0.3640 | 0.0696 | 0.2475 | −0.4693 |
| M2, 2 | 0.2349 | 0.2199 | −0.2756 | 0.2560 | −0.1870 | −0.2511 | −0.0007 | −0.1332 | 0.1388 |
| M2, 3 | 0.2345 | 0.1650 | −0.2028 | 0.3297 | −0.4615 | −0.0826 | −0.0045 | 0.0937 | 0.3774 |
| M4, 1 | 0.2586 | −0.0573 | −0.0212 | −0.2223 | −0.0489 | −0.2955 | −0.3419 | 0.1754 | −0.1774 |
| M4, 2 | 0.2529 | −0.1227 | −0.0859 | −0.2993 | −0.0351 | −0.2535 | 0.0210 | 0.3571 | −0.0670 |
| M4, 3 | 0.2557 | −0.0995 | −0.0839 | −0.2455 | −0.0516 | −0.3437 | −0.0744 | 0.1500 | −0.2267 |
| F2, 1 | 0.2194 | −0.3362 | −0.0248 | 0.4353 | 0.2550 | −0.2708 | 0.2080 | −0.2902 | −0.2957 |
| F2, 2 | 0.2312 | −0.3206 | 0.1408 | 0.2817 | 0.0707 | 0.1084 | −0.1457 | −0.1265 | −0.1627 |
| F2, 3 | 0.2186 | −0.3664 | 0.1072 | 0.2946 | 0.2958 | 0.1615 | −0.1228 | 0.4889 | 0.4167 |
| F5, 1 | 0.2224 | 0.2372 | 0.4214 | 0.0124 | −0.0110 | 0.1448 | −0.3667 | −0.1418 | 0.0773 |
| F5, 2 | 0.2182 | 0.2517 | 0.4410 | 0.0237 | −0.0078 | −0.0039 | −0.2954 | −0.0425 | −0.1198 |
| F5, 3 | 0.1913 | 0.3502 | 0.4781 | 0.0364 | 0.1468 | −0.2501 | 0.6255 | 0.1542 | 0.0533 |
| F6, 1 | 0.2329 | 0.1964 | −0.3066 | −0.1285 | 0.3927 | 0.0326 | 0.1500 | −0.0943 | 0.0856 |
| F6, 2 | 0.2439 | 0.1915 | −0.2026 | −0.1014 | 0.3065 | 0.3365 | −0.0162 | −0.0996 | −0.2178 |
| F6, 3 | 0.2434 | 0.1760 | −0.2210 | −0.1424 | 0.3322 | 0.0678 | −0.1306 | −0.1087 | 0.3368 |
| F7, 1 | 0.2459 | −0.2293 | 0.0618 | −0.2140 | −0.2315 | 0.0574 | 0.1701 | −0.2763 | 0.2092 |
| F7, 2 | 0.2405 | −0.2385 | 0.0812 | −0.2719 | −0.2240 | 0.4586 | 0.3318 | 0.1406 | −0.0110 |
| F7, 3 | 0.2531 | −0.1733 | 0.0577 | −0.1565 | −0.2016 | 0.0244 | 0.0292 | −0.4688 | 0.0892 |

Figure 23:
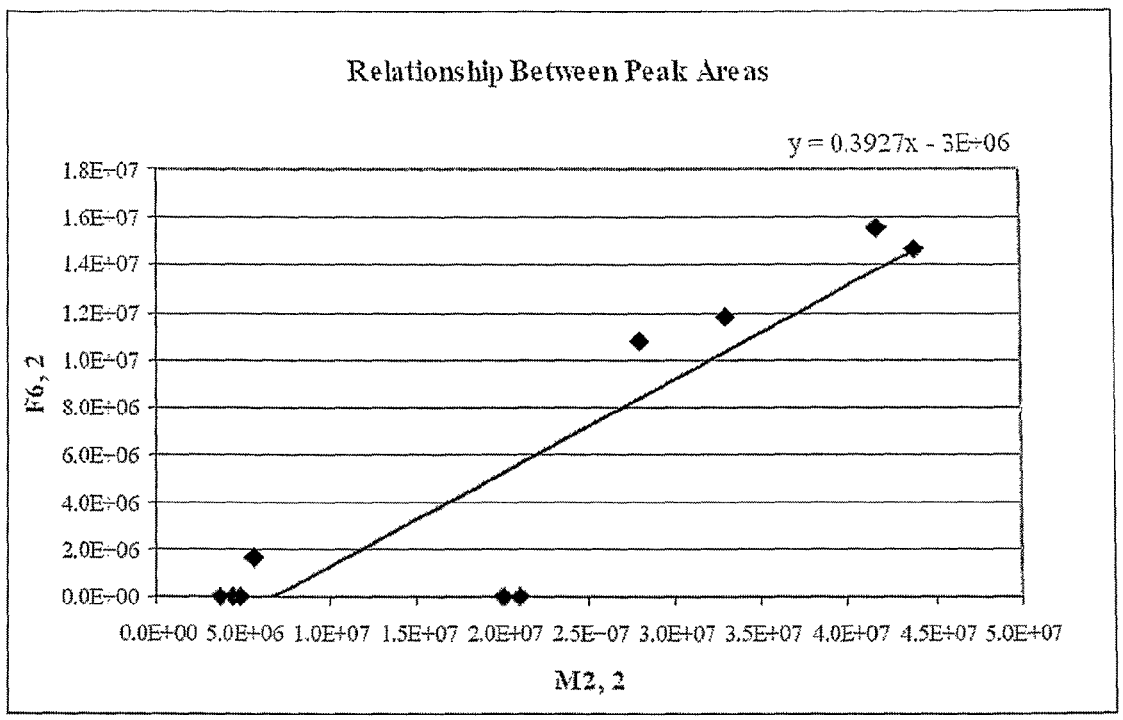
FIG. 23 shows the linear correlation between peak areas for two subjects (F6 and M2)
Figure 24:
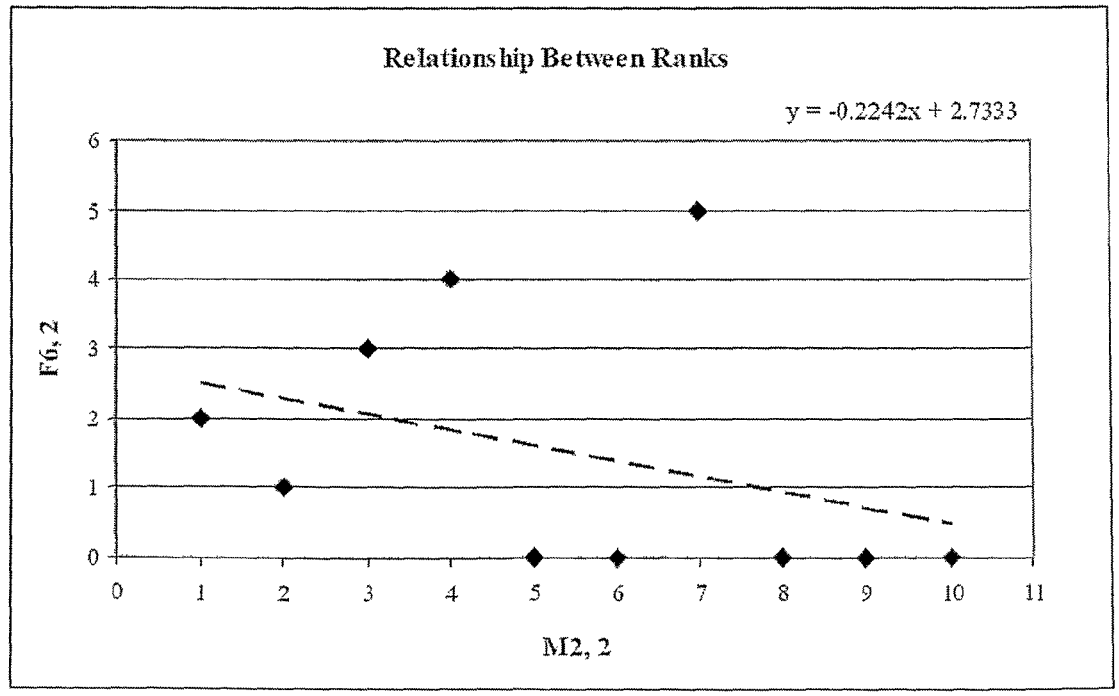
FIG. 24 shows the linear correlation between Spearman ranks for two subjects (F6 and M2)

The relationship seen through linear correlation between M2 sampling 2 and F6 sampling 2, as well as between Male 4 and Female 7, does not exist when using the Spearman Ranking method. This is due to magnitudal differences between the components within the profiles. For example, there are nine compounds total between M2 and F6. However, F6 only shows the presence of five of these compounds. As shown in FIG. 23 and FIG. 24, the missing values contribute in a greater fashion to the Spearman Ranking correlation value than in the linear correlation due to the scale of the values being compared.

These results show that through multiple samplings of an individual, determination of the common components in each sampling which are most likely to be elements of the primary odor for the subject, and comparison of these VOCs across a population, it is possible to narrow the field of possible matches of the profiles in question. PCA and linear correlation determinations were not able to differentiate all of the individuals studied, whereas the Spearman Ranking Correlation was able to distinguish all individuals in this study.

Figure 26:
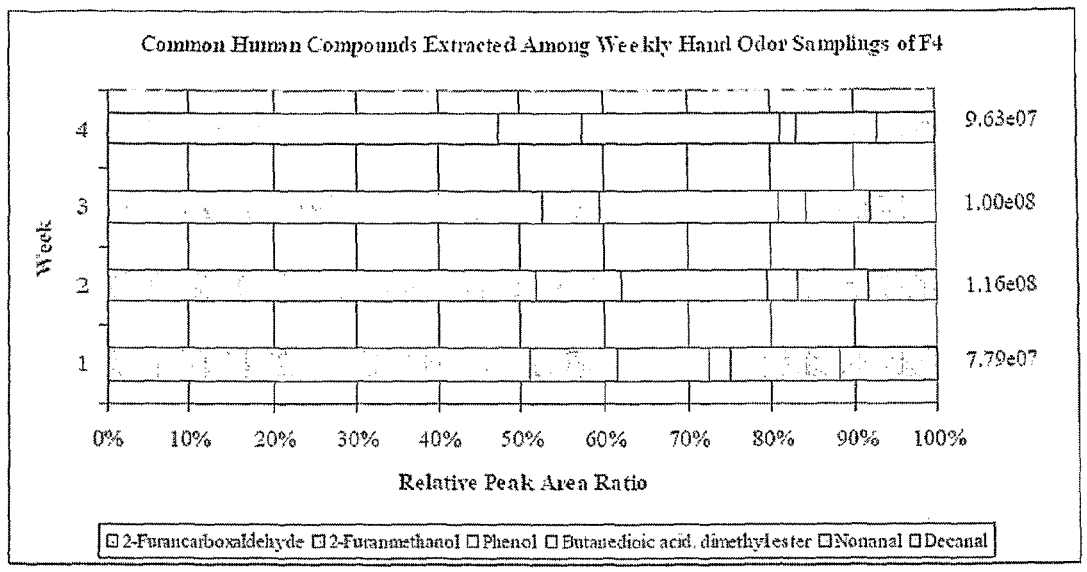
FIG. 26 shows the variation in hand odor samples from week to week for subject F4.
Figure 27:
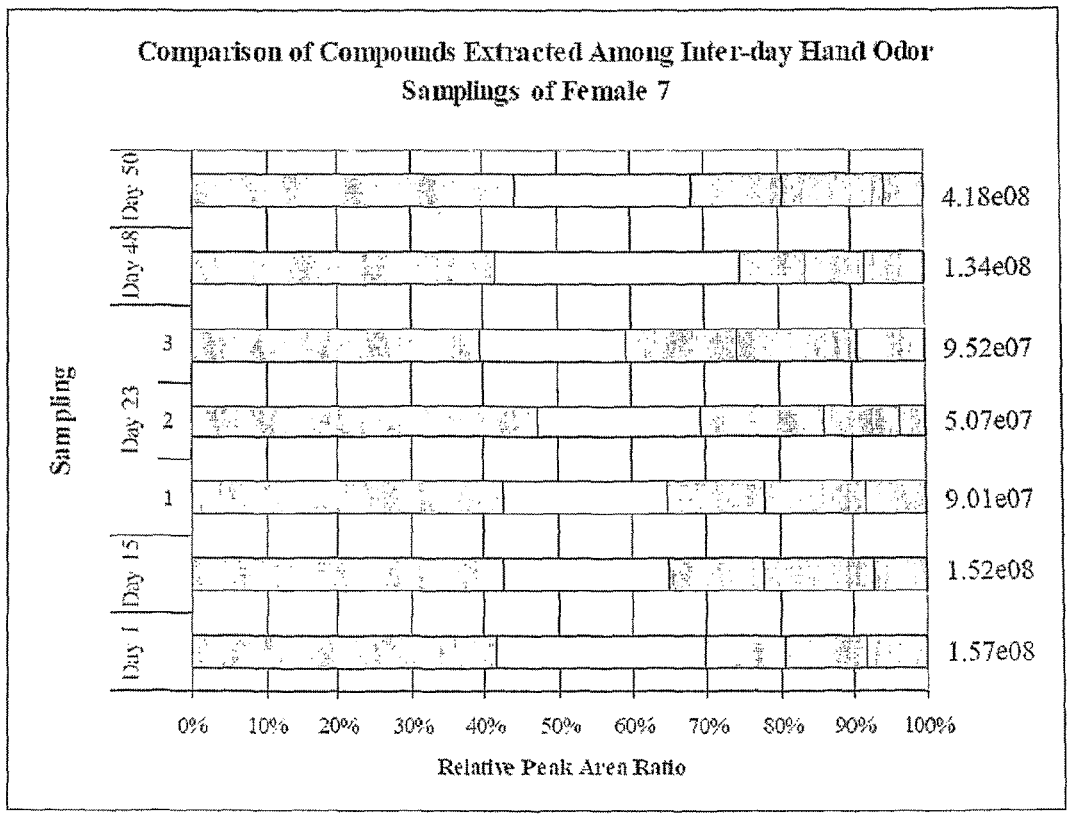
FIG. 27 shows the variation in hand odor samples from week to week for subject F7.
Figure 28:
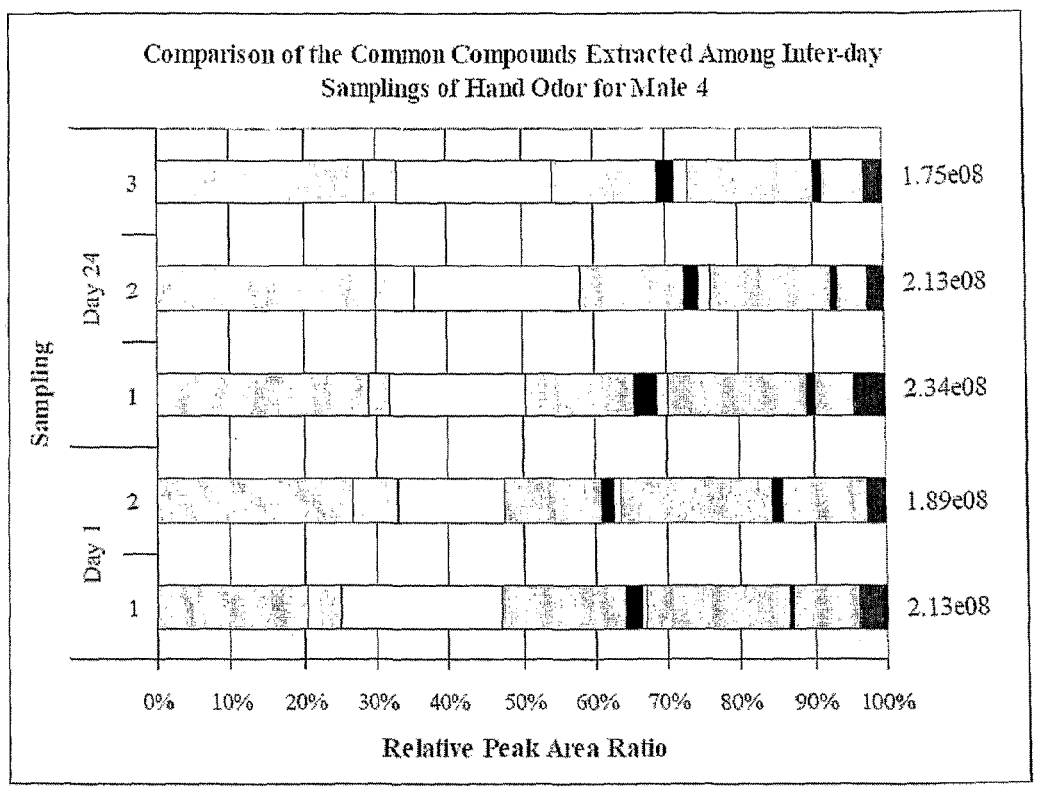
FIG. 28 shows the variation in hand odor samples from day 1 to day 24 for subject M4.

Inter-day Sampling: Hand odor was collected from three subjects (Female 4, Female 7, and Male 4) across multiple days to evaluate the stability of the volatile components over time. Compounds which were present in all samplings were deemed primary odor components and considered for stability comparisons. Female 4 was sampled once a week for four weeks, and six compounds were determined to be present in all four samplings: 2-furancarboxaldehyde, 2-furanmethanol, phenol, butanedioic acid-dimethyl ester, nonanal, and decanal. Female 7 was sampled across fifty days and displayed five common compounds in hand odor across inter-day sample comparison, including: 2-furancarboxaldehyde, phenol, nonanal, decanal, and hexanedioic acid-dimethyl ester. Female 7's common inter-day common compounds were the same as the common intra-day samplings previously compared. Male 4 was sampled twice in one day, then three times within the same day, twenty-four days later. Male 4 exhibited ten common compounds among the samplings, including: 2-furancarboxaldehyde, propanedioic acid-dimethyl ester, phenol, nonanal, octanoic acid-methyl ester, dodecane, decanal, nonanoic acid-methyl ester, hexanedioic acid-dimethyl ester, and 6,10-dimethyl-5,9-undecadien-2-one. Tetradecane, which was a common compound extracted among intra-day samplings of Male 4, was not present in the first hand odor sampling on Day 1 and, therefore, was not included in the common compounds for inter-day sampling for Male 4. The relative peak area ratios of the primary odor components for Female 4, Female 7, and Male 4 can be seen in FIG. 26, FIG. 27, and FIG. 28, respectively.

Spearman rank correlation analysis was conducted to compare the multiple inter-day samplings for each individual to the multiple intra-day samplings for the subjects previously described. The correlations of the three subjects are in Tables 31, 32, and 33, below. These findings support the hypothesis set forth through canine work that human odor is stable over time for an individual and can be differentiated among subjects.

TABLE 31

|  | F4, 1 | F4, 2 | F4, 3 | F4, 4 |
| --- | --- | --- | --- | --- |
| F4, 1 | 1 | 0.5429 | 0.7714 | 0.5429 |
| F4, 2 | 0.5429 | 1 | 0.7714 | 1 |
| F4, 3 | 0.7714 | 0.7714 | 1 | 0.7714 |
| F4, 4 | 0.5429 | 1 | 0.7714 | 1 |

TABLE 32

|  | F7, 1 | F7, 15 | F7, 23, 1 | F7, 23, 2 | F7, 23, 3 | F7, 48 | F7, 50 |
| --- | --- | --- | --- | --- | --- | --- | --- |
| F7, 1 | 1 | 1 | 1 | 0.9 | 1 | 0.7 | 1 |
| F7, 15 | 1 | 1 | 1 | 0.9 | 1 | 0.7 | 1 |
| F7, 23, 1 | 1 | 1 | 1 | 0.9 | 1 | 0.7 | 1 |
| F7, 23, 2 | 0.9 | 0.9 | 0.9 | 1 | 0.9 | 0.9 | 0.9 |
| F7, 23, 3 | 1 | 1 | 1 | 0.9 | 1 | 0.7 | 1 |
| F7, 48 | 0.7 | 0.7 | 0.7 | 0.9 | 0.7 | 1 | 0.7 |
| F7, 50 | 1 | 1 | 1 | 0.9 | 1 | 0.7 | 1 |

TABLE 33

|  | M4, 1, 1 | M4, 1, 2 | M4, 24, 1 | M4, 24, 2 | M4, 24, 3 |
| --- | --- | --- | --- | --- | --- |
| M4, 1, 1 | 1 | 0.9515 | 0.9273 | 0.9758 | 0.9758 |
| M4, 1, 2 | 0.9515 | 1 | 0.9515 | 0.9636 | 0.9636 |
| M4, 24, 1 | 0.9758 | 0.9515 | 1 | 0.9152 | 0.9394 |
| M4, 24, 2 | 0.9758 | 0.9636 | 0.9152 | 1 | 0.9758 |
| M4, 24, 3 | 0.9273 | 0.9636 | 0.9394 | 0.9758 | 1 |

Population Analysis of the Volatile Organic Compounds Present Above Collected Odor Samples Evaluation of the Compounds Present in Armpit Odor among Ten Individuals Materials: Gauze pads used were DUKAL brand, 100% cotton, sterile, 2×2, 8 ply, gauze sponges (DUKAL Corporation, Syosset, N.Y., USA), treated prior to use by the SFE method described above, and analyzed through SPME-GC/MS to ensure analytical cleanliness. The vials used to hold the gauze were 10 mL glass, clear, screw top vials with PTFE/Silicone septa (SUPELCO, Bellefonte, Pa., USA). The extraction solvent for the pre-treatment of the gauze pads by supercritical fluid extraction was supercritical grade carbon dioxide (Air Products, Allentown, Pa., USA). The methanol used as the modifier for the pre-treatment of the gauze pads was HPLC grade (Fisher Scientific, Pittsburgh, Pa., USA). The soap used by the subjects to wash all areas of the body was Natural, Clear Olive Oil Soap from Life of the Party (North Brunswick, N.J., USA).

Ten subjects were evaluated: five males M2, M4, M5, M6 and M7 and five females F2, F4, F5, F6, and F7. Male 5 was 17 years of age and Male 6 was 22 years of age. Female 4 and Female 5 were both 21 years of age, and Female 7 was 23 years of age. Male 2, Male 4, Female 2, and Female 6 were 24 years of age, while Male 7 was 28 years old. It is relevant to note that F6 and F7 are sisters who live in the same household. Subjects were required to use the olive oil soap and directed to shower at least twice using the provided soap during the 48 hr period prior to sampling. The subjects were also instructed to discontinue the use of deodorants, lotions, and perfumes for at least 48 hrs before sampling to minimize the influence of "tertiary odors." No attempt was made to control the diet of the subjects being sampled. Each subject exercised outdoors for a period of 30 min while wearing a tank top in order to minimize the influence of compounds present due to the influence of clothing. Subjects sampled themselves with a pre-treated 2×2 sterile gauze pad. The subjects were instructed to wipe the armpit area to collect their own sweat, then re-seal the sample back into the 10 mL glass vial. All samples were stored in the 10 mL vials at room temperature, and allowed to sit for approximately 24 hrs prior to extraction. These storage conditions were chosen to simulate the conditions under which odor is collected for canine evaluation purposes, and no attempt was made to control microbial interactions with the substrate because it may make contributions to the overall odor profile. The climatic conditions present during the samplings included an average temperature of 73° F. and an average humidity of 77%. Divinylbenzene/Carboxen on Polydimethylsiloxane (DVB/CAR on PDMS) 50/30 µm fibers (SUPELCO, Bellefonte, Pa., USA) were used to extract the volatile organic compounds from the headspace of the vials containing the gauze. The exposure for armpit samples was performed at room temperature for 15 hours. The fiber was then analyzed using the GC/MS method as described above.

There were some common compounds present among the subjects and also some compounds present which differ. Sixty-four compounds previously reported as components of human emanations were extracted between the ten subjects. The types of compounds determined to be in the odor profile included alcohols, aldehydes, alkanes, carboxylic acids, esters, and ketones.

Table 34 lists the compounds found in the odor profiles of the ten individuals studied. The compounds were identified by spectral library or by standard comparison. Six of the compounds were present in all of the subjects studied: phenol, nonanal, octanoic acid-methyl ester, decanal, tetradecane, and dodecanoic acid-methyl ester. Four compounds were extracted in nine of the ten subjects: 2-furancarboxaldehyde, nonanoic acid-methyl ester, 6,10-dimethyl-5,9-undecadien-2-one, and tetradecanoic acid-methyl ester. Hexanal, 1,2,4-trimethyl-benzene, benzyl alcohol, 2,4-dimethyl-hexane, acetophenone, phenylethyl alcohol, 1-chloro-nonane, 2-decanone, tetracosane, caryophyllene, tetradecanoic acid, and oleic acid were present in only one of the subjects. Propanedioic acid-methyl ester and octanal were both extracted in some of the males studied, yet were not present in any of the female profiles. 1-Methyl-2-(1-methylethyl)-benzene was extracted in some of the female subjects, but was not present in any of the male profiles.

TABLE 34

| Compound Name | M2 | M4 | M5 | M6 | M7 | F2 | F4 | F5 | F6 | F7 |
|---|---|---|---|---|---|---|---|---|---|---|
| Pyridine | X | | | | | X | | | | |
| Toluene | | | X | X | | | | X | X | X |
| Hexanal | | | | | | | X | | | |
| 2-Furancarboxaldehyde | X | X | | X | X | X | X | X | X | X |
| 2-Furanmethanol | X | X | X | | | X | X | X | | X |
| p-Xylene | | | | | | | | X | | |
| Nonane | | | | X | X | | | X | X | |
| Heptanal | | X | | | X | | | | X | |
| Hexanoic acid-methyl ester | X | | | X | | | X | X | | |
| Propanedioic acid-dimethyl ester | | | X | | | | | | | |
| .alpha.-Pinene | | | | | | | | X | | X |
| Benzaldehyde | X | | | | | X | | | | |
| Furancarboxylic acid-methyl ester | X | | | | | X | X | | | |
| Phenol | X | | X | X | | X | X | X | | X |
| 6-methyl-5-Hepten-2-one | X | | | X | | | X | | | X |
| 1,3,5-trimethylbenzene | | | | | | | | X | | |
| Octanal | X | | | | | | | | | |
| 1,2,4-trimethylbenzene | | | | | | | | | | |
| Benzene, 1-methyl-2-(1-methylethyl | | | | | | | | X | | X |
| Benzyl Alcohol | | | | | | | | | | |
| 2,4-dimethylhexane | | | X | | | | | | | |
| Acetophenone | | | X | | | | | | | |
| Undecane | | | | X | | | | | | X |
| Nonanal | X | | | X | X | | X | X | X | X |
| Phenylethyl Alcohol | | | | | | | | X | | |
| Octanoic acid-methyl ester | X | | | X | X | | X | X | X | X |
| 2-Nonenal | | | | | | | X | X | | X |
| 1-chlorononane | | | | | | | | X | | |
| Acetic acid-phenylmethyl ester | | | | | | | | X | | |
| Nonanol | | | | | | | X | | | |
| Naphthalene | | | | X | | | | X | | X |
| 2-Decanone | | | | | | | | | | |
| Dodecane | X | | X | | | X | X | X | | X |
| Decanal | X | | X | X | | X | X | X | | X |
| Nonanoic acid-methyl ester | X | | X | X | | X | X | X | | X |
| Hexanedioic acid-dimethyl ester | X | | | X | | X | X | | | |
| 2-Decenal, (E)- | | | | | | | X | | | |
| Tetracosane | | | | | | | | | | X |
| Tridecane | X | | X | X | | X | | X | | X |
| Undecanal | | | X | | | X | | | | X |
| Tetradecanal | X | | X | | | X | | | | |
| Decanoic acid-methyl ester | | | X | X | | X | X | X | | |
| 1-Pentadecene | | | X | | | X | | X | | |
| Tetradecane | X | | X | X | | X | X | X | | X |
| Diphenyl ether | | | | | | | | X | | X |
| Undecanoic acid-methyl ester | | | X | X | | X | | X | | |
| 6,10-dimethyl-5,9-Undecadien-2-one | X | | X | X | | X | X | | | X |
| Eicosane | | | | X | | | X | X | | X |
| 9-Octadecenoic acid-methyl ester | | | | | | | | X | | |
| Dodecanoic acid-methyl ester | X | | X | X | | X | X | X | | X |
| Dodecanoic acid | | | | | | | | X | | |
| Hexadecane | X | | X | | | X | | X | | X |
| Tridecanoic acid-methyl ester | | | X | X | | X | X | | | |
| Heptadecane | | | X | X | | X | | | | X |
| 7-Hexadecenoic acid-methyl ester | | | X | X | | | X | X | | |
| Tetradecanoic acid-methyl ester | X | | X | X | | X | X | X | | X |
| Tetradecanoic acid | | | | | | | | | | |
| Methyl 9-methyltetradecanoate | X | | | X | X | | X | | | |
| 12-methyltetradecanoic acid-methyl ester | | | | X | | | X | | | |
| Oleic Acid | | | | | | | | X | | |
| Pentadecanoic acid-methyl ester | | | X | X | | | X | X | | |
| 14-methyl-pentadecanoic acid-methyl ester | | | | X | | | | | | |
| Hexadecanoic acid-methyl ester | X | | X | X | | | X | X | | X |

Figure 29:
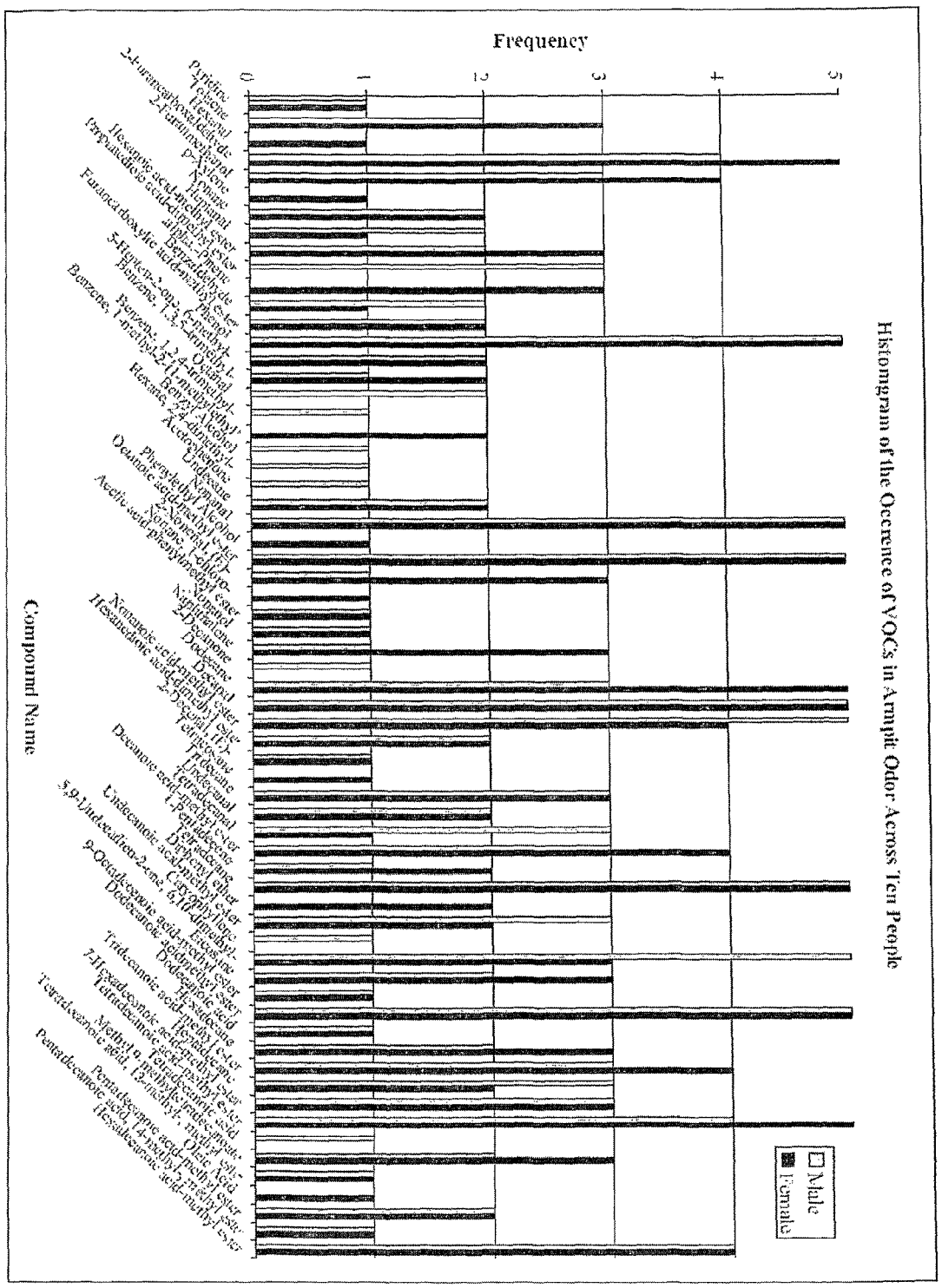
FIG. 29 shows a histogram of compounds identified in armpit odor samples from ten individuals.
Figure 30:
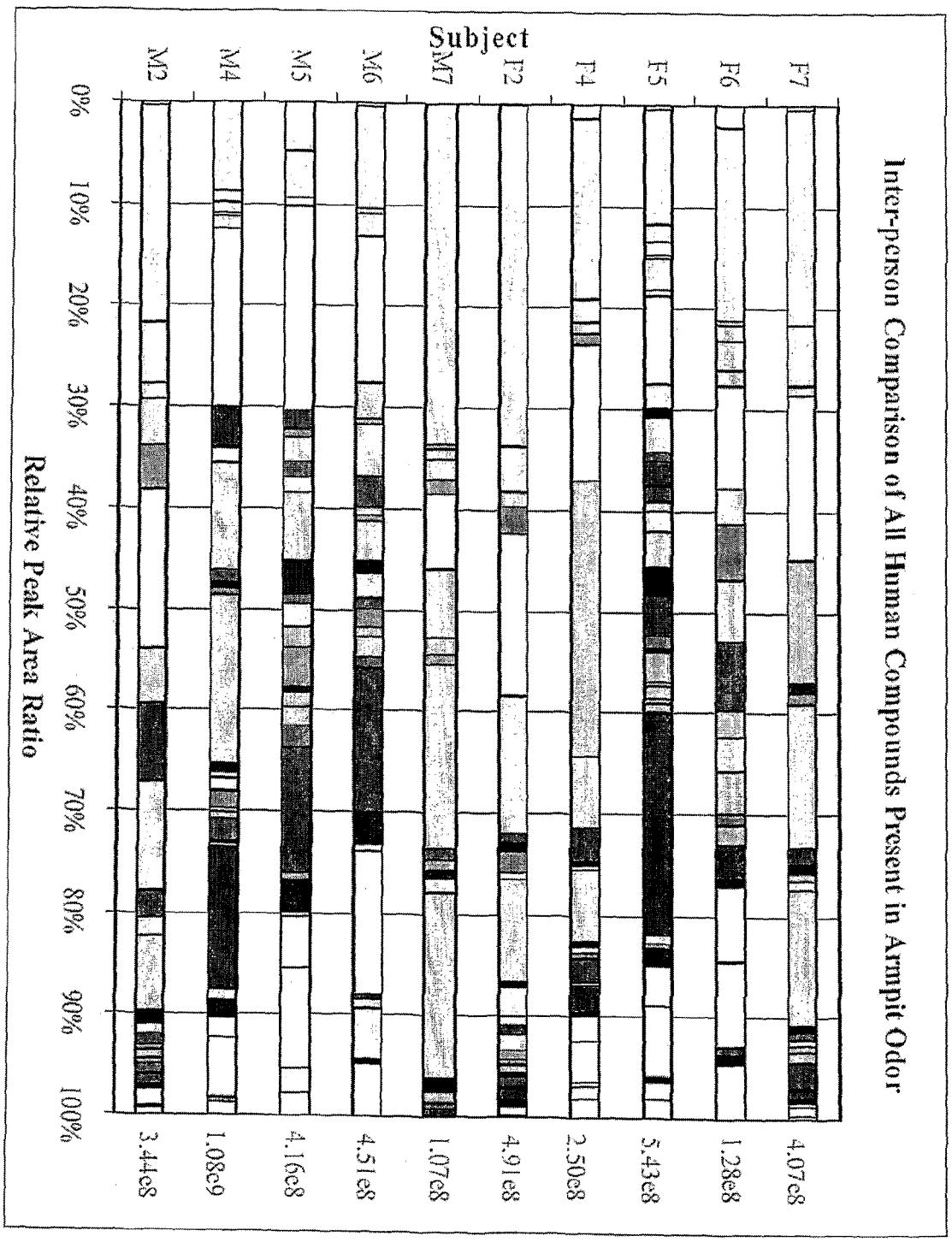
FIG. 30 shows the relative amounts of compounds identified in armpit odor samples in ten individuals.

The frequency of the occurrence of the human compounds extracted in armpit odor among the ten individuals are listed in Table 35 and displayed in the histogram in FIG. 29. As can be seen in the table, across the ten subjects, there are fifteen high frequency compounds (100-67% presence), nineteen medium frequency compounds (66-33% presence), and thirty-one low frequency compounds (32-1% presence) among the population. It is possible to distinguish between individuals based on relative peak area ratio patterns of the common compound extracted between multiple samplings of individuals. FIG. 30 demonstrates the greater variability between the odor profiles obtained among individuals when the human compounds, which differ between individuals, are also considered.

TABLE 35

| Compound Name | Frequency of Occurrence | | | Percentage of | | |
|---|---|---|---|---|---|---|
| | Males | Females | Total | Males | Females | Total |
| Pyridine | 1 | 1 | 2 | 20 | 20 | 20 |
| Toluene | 2 | 3 | 5 | 40 | 60 | 50 |
| Hexanal | 0 | 1 | 1 | 0 | 20 | 10 |
| 2-Furancarboxaldehyde | 4 | 5 | 9 | 80 | 100 | 90 |
| 2-Furanmethanol | 3 | 4 | 7 | 60 | 80 | 70 |
| p-Xylene | 0 | 1 | 1 | 0 | 20 | 10 |
| Nonane | 2 | 2 | 4 | 40 | 40 | 40 |
| Heptanal | 2 | 1 | 3 | 40 | 20 | 30 |
| Hexanoic acid-methyl ester | 2 | 3 | 5 | 40 | 60 | 50 |
| Propanedioic acid-dimethyl ester | 3 | 0 | 3 | 60 | 0 | 30 |
| α-Pinene | 0 | 3 | 3 | 0 | 60 | 30 |
| Benzaldehyde | 2 | 1 | 3 | 40 | 20 | 30 |
| Furancarboxylic acid-methyl ester | 2 | 2 | 4 | 40 | 40 | 40 |
| Phenol | 5 | 5 | 10 | 100 | 100 | 100 |
| 5-Hepten-2-one, 6-methyl- | 2 | 2 | 4 | 40 | 40 | 40 |
| Benzene, 1,3,5-trimethyl- | 1 | 2 | 3 | 20 | 40 | 30 |
| Octanal | 2 | 0 | 2 | 40 | 0 | 20 |
| Benzene, 1,2,4-trimethyl- | 1 | 0 | 1 | 20 | 0 | 10 |
| Benzene, 1-methyl-2-(1-methylethyl | 0 | 2 | 2 | 0 | 40 | 20 |
| Benzyl Alcohol | 1 | 0 | 1 | 20 | 0 | 10 |
| Hexane, 2,4-dimethyl- | 1 | 0 | 1 | 20 | 0 | 10 |
| Acetophenone | 1 | 0 | 1 | 20 | 0 | 10 |
| Undecane | 2 | 2 | 4 | 40 | 40 | 40 |
| Nonanal | 5 | 5 | 10 | 100 | 100 | 100 |
| Phenylethyl Alcohol | 0 | 1 | 1 | 0 | 20 | 10 |
| Octanoic acid-methyl ester | 5 | 5 | 10 | 100 | 100 | 100 |
| 2-Nonenal, (E)- | 1 | 3 | 4 | 20 | 60 | 40 |
| Nonane, 1-chloro- | 0 | 1 | 1 | 0 | 20 | 10 |
| Acetic acid-phenylmethyl ester | 1 | 1 | 2 | 20 | 20 | 20 |
| Nonanol | 1 | 1 | 2 | 20 | 20 | 20 |
| Naphthalene | 1 | 3 | 4 | 20 | 60 | 40 |
| 2-Decanone | 1 | 0 | 1 | 20 | 0 | 10 |
| Dodecane | 3 | 5 | 8 | 60 | 100 | 80 |
| Decanal | 5 | 5 | 10 | 100 | 100 | 100 |
| Nonanoic acid-methyl ester | 5 | 4 | 9 | 100 | 80 | 90 |
| Hexanedioic acid-dimethyl ester | 2 | 2 | 4 | 40 | 40 | 40 |
| 2-Decenal, (E)- | 1 | 1 | 2 | 20 | 20 | 20 |
| Tetracosane | 0 | 1 | 1 | 0 | 20 | 10 |
| Tridecane | 3 | 3 | 6 | 60 | 60 | 60 |
| Undecanal | 2 | 2 | 4 | 40 | 40 | 40 |
| Tetradecanal | 3 | 1 | 4 | 60 | 20 | 40 |
| Decanoic acid-methyl ester | 3 | 4 | 7 | 60 | 80 | 70 |
| 1-Pentadecene | 1 | 2 | 3 | 20 | 40 | 30 |
| Tetradecane | 5 | 5 | 10 | 100 | 100 | 100 |
| Diphenyl ether | 0 | 2 | 2 | 0 | 40 | 20 |
| Undecanoic acid-methyl ester | 3 | 2 | 5 | 60 | 40 | 50 |
| Caryophyllene | 1 | 0 | 1 | 20 | 0 | 10 |
| 5,9-Undecadien-2-one, 6,10-dimethy | 5 | 3 | 8 | 100 | 60 | 80 |
| Eicosane | 2 | 3 | 5 | 40 | 60 | 50 |
| 9-Octadecenoic acid (Z)-, methyl ester | 1 | 1 | 2 | 20 | 20 | 20 |
| Dodecanoic acid-methyl ester | 5 | 5 | 10 | 100 | 100 | 100 |
| Dodecanoic acid | 1 | 1 | 2 | 20 | 20 | 20 |
| Hexadecane | 2 | 3 | 5 | 40 | 60 | 50 |
| Tridecanoic acid-methyl ester | 3 | 4 | 7 | 60 | 80 | 70 |
| Heptadecane | 3 | 2 | 5 | 60 | 40 | 50 |
| 7-Hexadecenoic acid-methyl ester | 3 | 3 | 6 | 60 | 60 | 60 |
| Tetradecanoic acid-methyl ester | 4 | 5 | 9 | 80 | 100 | 90 |
| Tetradecanoic acid | 1 | 0 | 1 | 20 | 0 | 10 |
| Methyl 9-methyltetradecanoate | 2 | 3 | 5 | 40 | 60 | 50 |
| Tetradecanoic acid, 12-methyl- | 1 | 1 | 2 | 20 | 20 | 20 |
| Oleic Acid | 0 | 1 | 1 | 0 | 20 | 10 |
| Pentadecanoic acid-methyl ester | 2 | 2 | 4 | 40 | 40 | 40 |
| Pentadecanoic acid, 14-methyl- | 1 | 1 | 2 | 20 | 20 | 20 |
| Hexadecanoic acid-methyl ester | 4 | 4 | 8 | 80 | 80 | 80 |

Evaluation of the Components of Hand Odor Among Sixty Individuals Materials

Supercritical fluid extraction (SFE) using methanol modified carbon dioxide was used as a pretreatment for the gauze that creates an analytically clean collection medium. Gauze pads were DUKAL brand, sterile, 2×2, 8 ply, gauze sponges (DUKAL Corporation, Syosset, N.Y., USA). The vials used to hold the gauze were 10 mL glass, clear, screw top vials with PTFE/Silicone septa (SUPELCO, Bellefonte, Pa., USA). The extraction solvent for the pre-treatment of the gauze pads by supercritical fluid extraction was supercritical grade carbon dioxide (Air Products, Allentown, Pa., USA). The methanol used as the modifier for the pre-treatment of the gauze pads was HPLC grade (Fisher Scientific, Pittsburgh, Pa., USA). The soap used by the subjects to wash the hands and forearms was Natural, Clear Olive Oil Soap from Life of the Party (North Brunswick, N.J., USA).

Sixty subjects were evaluated, thirty males and thirty females ranging in age from 17-28 years old, The sampling protocol was as follows: 30 seconds of washing the hands and forearms with olive oil based soap, 2 min of rinsing the areas with cool water, 2 min of air drying, and followed by 5 min of rubbing the palms of the hands over the forearms. A pre-treated 2×2 sterile gauze pad was then removed from the 10 ml glass vial using tweezers previously rinsed with a 10% bleach solution, and placed in the palms of the subject's hands. The subjects then sampled themselves by holding the pre-treated gauze between the palms of their hands, walking outdoors for 10 min, then re-sealing the sample back into the 10 ml glass vial. All samples were stored in the 10 mL vials at room temperature, and allowed to sit for approximately 24 hrs prior to extraction. These storage conditions were chosen to simulate the conditions under which odor is collected for canine evaluation purposes, and no attempt was made to control microbial interactions with the substrate because it may make contributions to the overall odor profile. The climatic conditions present during the samplings included an average temperature of 80° F. and an average humidity of 76%. DVB/CAR on PDMS fibers were used to extract the volatile organic compounds from the headspace of the vials containing the scented gauze. Exposures were conducted at room temperature for 21 hrs. The fibers were then analyzed using GC/MS methods described above.

Figure 31:
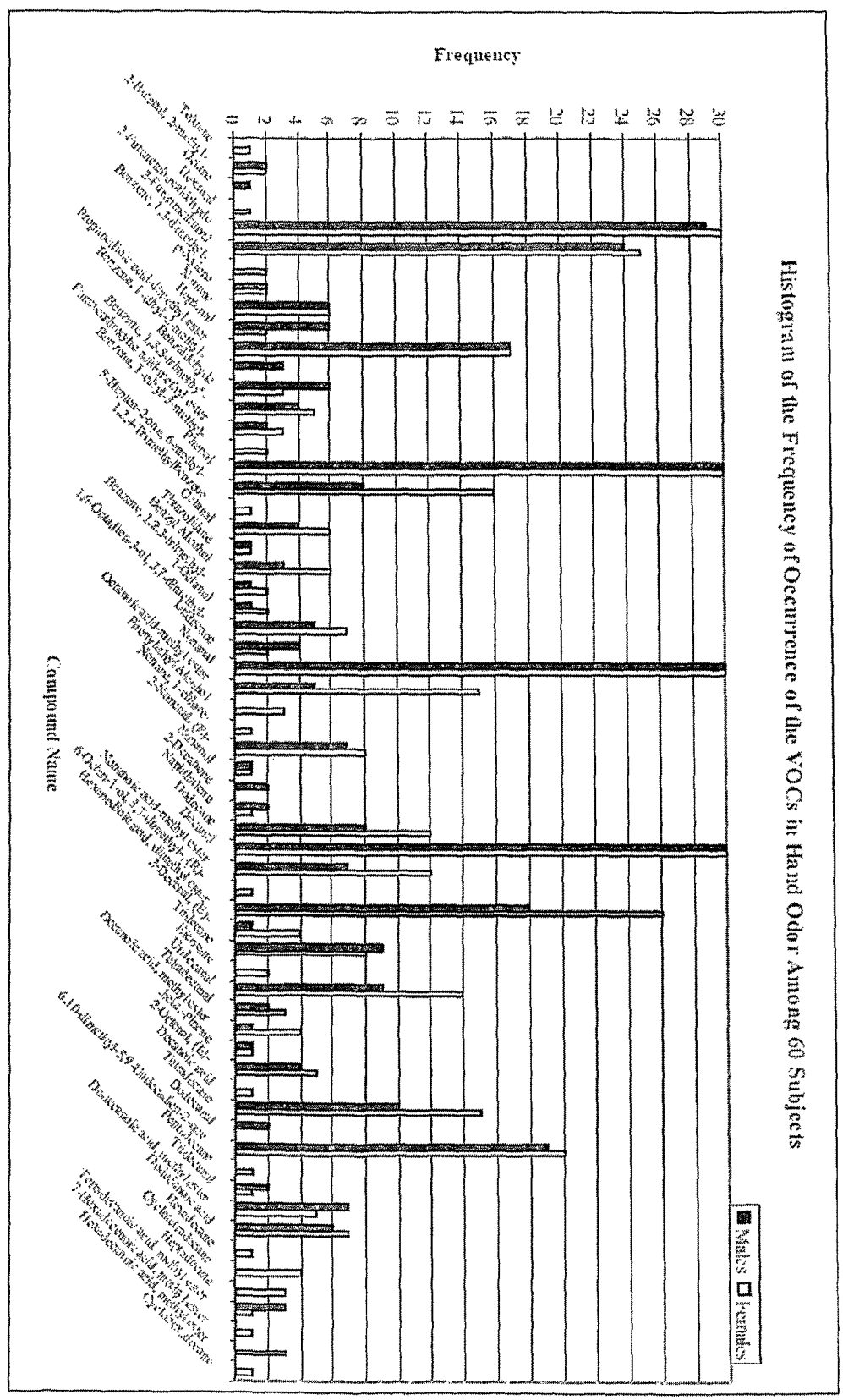
FIG. 31 shows a histogram of the frequency of VOCs present in hand odor samples among sixty individuals studied.

Table 36 lists the frequency of occurrence of the compounds identified in the headspace of the hand odor collected from the sixty subjects, which have been previously reported as components of human secretions, as well as the number of subjects which contain them separated by gender. The compounds are listed in order of retention time, were identified by spectral library or by standard comparison, and have all been previously reported as components of human secretions as noted. Table 36 also shows the percentages of occurrence of the compounds across the sample population separated by gender. Some compounds, which have been previously reported to be present in human secretions, such as 2-ethyl-1-hexanol, lilial, and limonene, are not listed, because they have been disregarded as possible "tertiary odors," i.e. skin lotion, perfumes, clothing, and the like. Methyl salicylate (present in less than 5% of the population) has also been disregarded, because it is most likely a "secondary odor" component due to the consumption of aspirin. Across the sixty subjects, there are six high frequency compounds (100-67% presence), seven medium frequency compounds (66-33% presence), and fifty low frequency compounds (32-1% presence) among the population. FIG. 31 shows the histogram of the frequency of occurrence of the VOCs present in hand odor among the population studied.

TABLE 36

| Compound Name | Frequency of Occurrence | | | Percentage of Occurrence (%) | | |
| --- | --- | --- | --- | --- | --- | --- |
| | Males | Females | Total | Males | Females | Total |
| Pyridine | 1 | 0 | 1 | 3.33 | 0.00 | 1.67 |
| Toluene | 0 | 1 | 1 | 0.00 | 3.33 | 1.67 |
| 2-Butenal, 2-methyl- | 2 | 2 | 4 | 6.67 | 6.67 | 6.67 |
| Octane | 1 | 0 | 1 | 3.33 | 0.00 | 1.67 |
| Hexanal | 0 | 1 | 1 | 0.00 | 3.33 | 1.67 |
| 2-Furancarboxaldehyde | 29 | 30 | 59 | 96.67 | 100 | 98.33 |
| 2-Furanmethanol | 24 | 25 | 49 | 80.00 | 83.33 | 81.67 |
| Benzene, 1,3-dimethyl- | 0 | 2 | 2 | 0.00 | 6.67 | 3.33 |
| p-Xylene | 2 | 2 | 4 | 6.67 | 6.67 | 6.67 |
| Nonane | 6 | 6 | 12 | 20.00 | 20.00 | 20.00 |
| Heptanal | 6 | 2 | 8 | 20.00 | 6.67 | 13.33 |
| Propanedioic acid-dimethyl ester | 17 | 17 | 34 | 56.67 | 56.67 | 56.67 |
| Benzene, 1-ethyl-2-methyl- | 3 | 0 | 3 | 10.00 | 0.00 | 5.00 |
| Benzaldehyde | 6 | 3 | 9 | 20.00 | 10.00 | 15.00 |
| Benzene, 1,3,5-trimethyl- | 4 | 5 | 9 | 13.33 | 16.67 | 15.00 |
| Furancarboxylic acid-methyl ester | 2 | 3 | 5 | 6.67 | 10.00 | 8.33 |
| Benzene, 1-ethyl-3-methyl- | 0 | 2 | 2 | 0.00 | 6.67 | 3.33 |
| Phenol | 30 | 30 | 60 | 100 | 100 | 100 |
| 5-Hepten-2-one, 6-methyl- | 8 | 16 | 24 | 26.67 | 53.33 | 40.00 |
| 1,2,4-Trimethylbenzene | 0 | 1 | 1 | 0.00 | 3.33 | 1.67 |
| Octanal | 4 | 6 | 10 | 13.33 | 20.00 | 16.67 |
| Thiazolidine | 1 | 1 | 2 | 3.33 | 3.33 | 3.33 |
| Benzyl Alcohol | 3 | 6 | 9 | 10.00 | 20.00 | 15.00 |
| Benzene, 1,2,3-trimethyl- | 1 | 2 | 3 | 3.33 | 6.67 | 5.00 |
| 1-Octanol | 1 | 2 | 3 | 3.33 | 6.67 | 5.00 |
| 1,6-Octadien-3-ol, 3,7-dimethyl- | 5 | 7 | 12 | 16.67 | 23.33 | 20.00 |
| Undecane | 4 | 2 | 6 | 13.33 | 6.67 | 10.00 |
| Nonanal | 30 | 30 | 60 | 100 | 100 | 100 |
| Octanoic acid-methyl ester | 5 | 15 | 20 | 16.67 | 50.00 | 33.33 |
| Phenylethyl Alcohol | 0 | 3 | 3 | 0.00 | 10.00 | 5.00 |

TABLE 36-continued

| Compound Name | Frequency of Occurrence | | | Percentage of Occurrence (%) | | |
|---|---|---|---|---|---|---|
| | Males | Females | Total | Males | Females | Total |
| Nonane, 1-chloro- | 0 | 1 | 1 | 0.00 | 3.33 | 1.67 |
| 2-Nonenal, (E)- | 7 | 8 | 15 | 23.33 | 26.67 | 25.00 |
| Nonanol | 1 | 1 | 2 | 3.33 | 3.33 | 3.33 |
| 2-Decanone | 2 | 0 | 2 | 6.67 | 0.00 | 3.33 |
| Naphthalene | 2 | 1 | 3 | 6.67 | 3.33 | 5.00 |
| Dodecane | 8 | 12 | 20 | 26.67 | 40.00 | 33.33 |
| Decanal | 30 | 30 | 60 | 100 | 100 | 100 |
| Nonanoic acid-methyl ester | 7 | 12 | 19 | 23.33 | 40.00 | 31.67 |
| 6-Octen-1-ol, 3,7-dimethyl-, (R)- | 0 | 1 | 1 | 0.00 | 3.33 | 1.67 |
| Hexanedioic acid, dimethyl ester | 18 | 26 | 44 | 60.00 | 86.67 | 73.33 |
| 2-Decenal, (E)- | 1 | 4 | 5 | 3.33 | 13.33 | 8.33 |
| Tridecane | 9 | 8 | 17 | 30.00 | 26.67 | 28.33 |
| Eicosane | 0 | 2 | 2 | 0.00 | 6.67 | 3.33 |
| Undecanal | 9 | 14 | 23 | 30.00 | 46.67 | 38.33 |
| Tetradecanal | 2 | 3 | 5 | 6.67 | 10.00 | 8.33 |
| Decanoic acid, methyl ester | 1 | 4 | 5 | 3.33 | 13.33 | 8.33 |
| β-Pinene | 1 | 1 | 2 | 3.33 | 3.33 | 3.33 |
| 2-Octenal, (E)- | 4 | 5 | 9 | 13.33 | 16.67 | 15.00 |
| Decanoic acid | 0 | 1 | 1 | 0.00 | 3.33 | 1.67 |
| Tetradecane | 10 | 15 | 25 | 33.33 | 50.00 | 41.67 |
| Dodecanal | 2 | 0 | 2 | 6.67 | 0.00 | 3.33 |
| 6,10-dimethyl-5,9-undecadien-2-one | 19 | 20 | 39 | 63.33 | 66.67 | 65.00 |
| Pentadecane | 0 | 1 | 1 | 0.00 | 3.33 | 1.67 |
| Tridecanal | 2 | 1 | 3 | 6.67 | 3.33 | 5.00 |
| Dodecanoic acid, methyl ester | 7 | 5 | 12 | 23.33 | 16.67 | 20.00 |
| Dodecanoic acid | 6 | 7 | 13 | 20.00 | 23.33 | 21.67 |
| Hexadecane | 0 | 1 | 1 | 0.00 | 3.33 | 1.67 |
| Cyclotetradecane | 0 | 4 | 4 | 0.00 | 13.33 | 6.67 |
| Heptadecane | 0 | 3 | 3 | 0.00 | 10.00 | 5.00 |
| Tetradecanoic acid, methyl ester | 3 | 1 | 4 | 10.00 | 3.33 | 6.67 |
| 7-Hexadecenoic acid, methyl ester | 0 | 1 | 1 | 0.00 | 3.33 | 1.67 |
| Hexadecanoic acid, methyl ester | 0 | 3 | 3 | 0.00 | 10.00 | 5.00 |
| Cyclohexadecane | 0 | 1 | 1 | 0.00 | 3.33 | 1.67 |

The compounds extracted can be divided into seven groups by functionality: acids, alcohols, aldehydes, alkanes, esters, ketones, and nitrogen containing compounds. The six high frequency compounds across both the males and females include: 2-furancarboxaldehyde, 2-furanmethanol, phenol, nonanal, decanal, and hexanedioic aciddimethyl ester. Of these compounds, nonanal and decanal were previously reported as high frequency compounds in the headspace above the forearm skin of females. The seven medium frequency compounds across the males and the females include: propanedioic acid-dimethyl ester, 6-methyl-5-hepten-2-one, octanoic acid-methyl ester, dodecane, undecanal, 6,10-dimethyl-5,9-undecadiene-2-one, and tetradecane. Tetradecane was also previously reported as a high frequency compound present in the headspace above the forearm skin of females. However, 6-methyl-5-hepten-2-one was mentioned as a low frequency compound.

Fifteen of the sixty-three compounds extracted were aldehydes, which are present in human odor as a result of oxidative degradation of sebaceous secretion components. E-2-nonenal was extracted in 25% of the total population whose ages ranged from 17-28 years of age, which is incompatible with the possibility of utilizing E-2-nonenal as a compound which increases with age and as a possible odor marker for individuals over the age of 40. A preliminary study into the VOCs present in the headspace of collected hand odor from children has also revealed the presence of E-2-nonenal. Hexanal, heptanal, and phenol were extracted among the population and have been shown to be volatile components of the blood.

It can be postulated that the fresher the scent sample, the higher the probability that compounds with greater volatility are present as compared to aged samples, where these types of compounds may have dissipated. This has been supported anecdotally from the behavior of bloodhounds when following a scent trail. A fresh trail is followed with the head in an upright position suggesting that more volatile compounds are being utilized, whereas an old trail is followed with the nose to the ground suggesting that less volatile compounds are present. The ability of human scent line-up canines to match odor which has been collected and stored in a glass jar for more than seven years suggests that a steady state is created within the container, which limits dissipation of the odor components. The samples collected for this study were also stored in a glass container and the high and medium frequency compounds extracted among the population studied have vapor pressures that fall in the semi-volatile range as compared to some of the low frequency compounds, as can be seen in Table 37. Canines have the demonstrated the ability to smell TNT (v.p.=$3.0 \times 10^{-6}$ torr) and TNT can also be readily extracted through headspace SPME. Therefore, it is reasonable to assume that all forty-five compounds listed with vapor pressures equal to or greater than $10^{-6}$ torr can also be detected by canines. It is possible that a product of the long exposure times of the SPME fiber to the headspace inside the vial containing the scent sample is the extraction compounds with low vapor pressures are appearing in the odor profiles.

TABLE 37

| Frequency (H/M/L) | Compound Name | Vapor Pressure (torr) | Molecular Weight (g/mol) |
|---|---|---|---|
| | Acid | | |
| L | Dodecanoic Acid | $8.991E-07^a$ | 200.32 |
| L | Decanoic acid | $1.338E-16^a$ | 172.27 |
| | Alcohol | | |
| H | 2-Furanmethanol | $6.098E-01^a$ | 98.10 |
| H | Phenol | $2.199E-02^a$ | 94.11 |
| L | 3,7-dimethyl-1,6-octadien-3-ol | $7.303E-03^a$ | 154.25 |
| L | Benzyl alcohol | $6.379E-03^a$ | 108.14 |
| L | Phenylethyl alcohol | $6.246E-03^a$ | 122.17 |
| L | 1-octanol | $4.911E-03^a$ | 130.23 |
| L | 3,7-dimethyl-6-octen-1-ol | $3.086E-03^a$ | 156.00 |
| L | Nonanol | $8.088E-04^a$ | 144.25 |
| | Aldehyde | | |
| L | 2-methyl-2-butenal | $1.705^a$ | 84.12 |
| H | 2-Furancarboxaldehyde | $1.870E-01^a$ | 96.09 |
| L | Heptanal | $1.829E-01^a$ | 114.19 |
| L | Benzaldehyde | $6.011E-02^a$ | 106.12 |
| L | Hexanal | $5.310E-02^b$ | 100.16 |
| L | Octanal | $4.339E-02^b$ | 128.21 |
| H | Nonanal | $3.330E-02^b$ | 142.24 |
| H | Decanal | $9.570E-03^a$ | 156.27 |
| M | Dodecanal | $1.792E-03^a$ | 184.32 |
| L | Tetradecanal | $3.445E-04^a$ | 212.37 |
| L | E-2-decenal | Not Available | 126.20 |
| L | (E)-2-nonenal | Not Available | 140.22 |
| M | Undecanal | Not Available | 154.25 |
| L | (E)-2-octenal | Not Available | 170.29 |
| L | Tridecanal | Not Available | 198.35 |
| | Aliphatic/Aromatic | | |
| L | Toluene | 2.822a | 92.14 |
| L | Octane | 1.037a | 114.23 |
| L | 1-Chlorononane | 1.037a | 162.70 |
| L | p-Xylene | $6.595E-01^a$ | 106.17 |
| L | Nonane | $2.532E-01^a$ | 128.26 |
| L | Benzene, 1-ethyl-3-methyl- | $2.086E-01^a$ | 120.19 |
| L | Benzene, 1-ethyl-2-methyl- | $1.759E-01^a$ | 120.19 |
| L | Benzene, 1,3,5-trimethyl- | $1.710E-01^a$ | 120.19 |
| L | Benzene, 1,2,3-trimethyl- | $1.039E-01^a$ | 120.19 |
| L | .beta.-Pinene | $4.328E-02^b$ | 136.24 |
| L | 1,2,4-Trimethylbenzene | $4.011E-02^b$ | 120.19 |
| L | Undecane | $2.583E-02^a$ | 156.31 |
| L | Naphthalene | $1.739E-02^a$ | 128.17 |
| M | Dodecane | $7.203E-03^a$ | 170.34 |
| L | Pentadecane | $6.379E-03^a$ | 212.42 |
| L | Tridecane | $2.008E-03^a$ | 184.36 |
| L | Tetradecane | $5.354E-04^a$ | 198.39 |
| L | Hexadecane | $3.616E-05^a$ | 226.44 |
| L | Heptadecane | $5.123E-06^a$ | 240.47 |
| L | Cyclotetradecane | Not Available | 196.00 |
| L | 1,3-dimethyl-benzene | Not Available | 106.17 |
| L | Eicosane | Not Available | 224.43 |
| L | Cyclohexadecane | Not Available | 282.55 |
| | Ketones | | |
| M | 6-methyl-5-hepten-2-one | Not Available | 126.20 |
| M | 6,10-dimethyl-5,9-undecadien-2-one | Not Available | 156.27 |
| L | 2-Decanone | Not Available | 194.32 |
| | Esters | | |
| M | Propanedioic acid, dimethyl ester | $3.254E-02^a$ | 132.00 |
| M | Octanoic acid, methyl ester | $2.427E-02^a$ | 158.24 |
| L | Decanoic acid, methyl ester | $3.055E-03^a$ | 186.29 |
| H | Hexanedioic acid, dimethyl ester | $1.506E-03^a$ | 174.00 |
| L | Dodecanoic acid, methyl ester | $5.466E-04^a$ | 214.35 |
| L | Tetradecanoic acid, methyl ester | $1.304E-04^a$ | 242.40 |
| L | Hexadecanoic acid, methyl ester | $2.598E-05^a$ | 270.45 |
| L | Furancarboxylic acid, methyl ester | Not Available | 126.00 |
| L | Nonanoic acid, methyl ester | Not Available | 172.27 |

TABLE 37-continued

| Frequency (H/M/L) | Compound Name | Vapor Pressure (torr) | Molecular Weight (g/mol) |
|---|---|---|---|
| L | 7-hexadecenoic acid, methyl ester | Not Available | 268.00 |
| | Amines/Amides | | |
| L | Pyridine | $2.051^a$ | 79.10 |
| L | Thiazolidine | Not Available | 89.16 |

$^a$Vapor pressures calculated using the Antoine Equation from Knovel Critical Tables;
$^b$Extrapolated from data found in the Handbook of Chemistry & Physics (www.hbcpnetbase.com)

Figure 32:
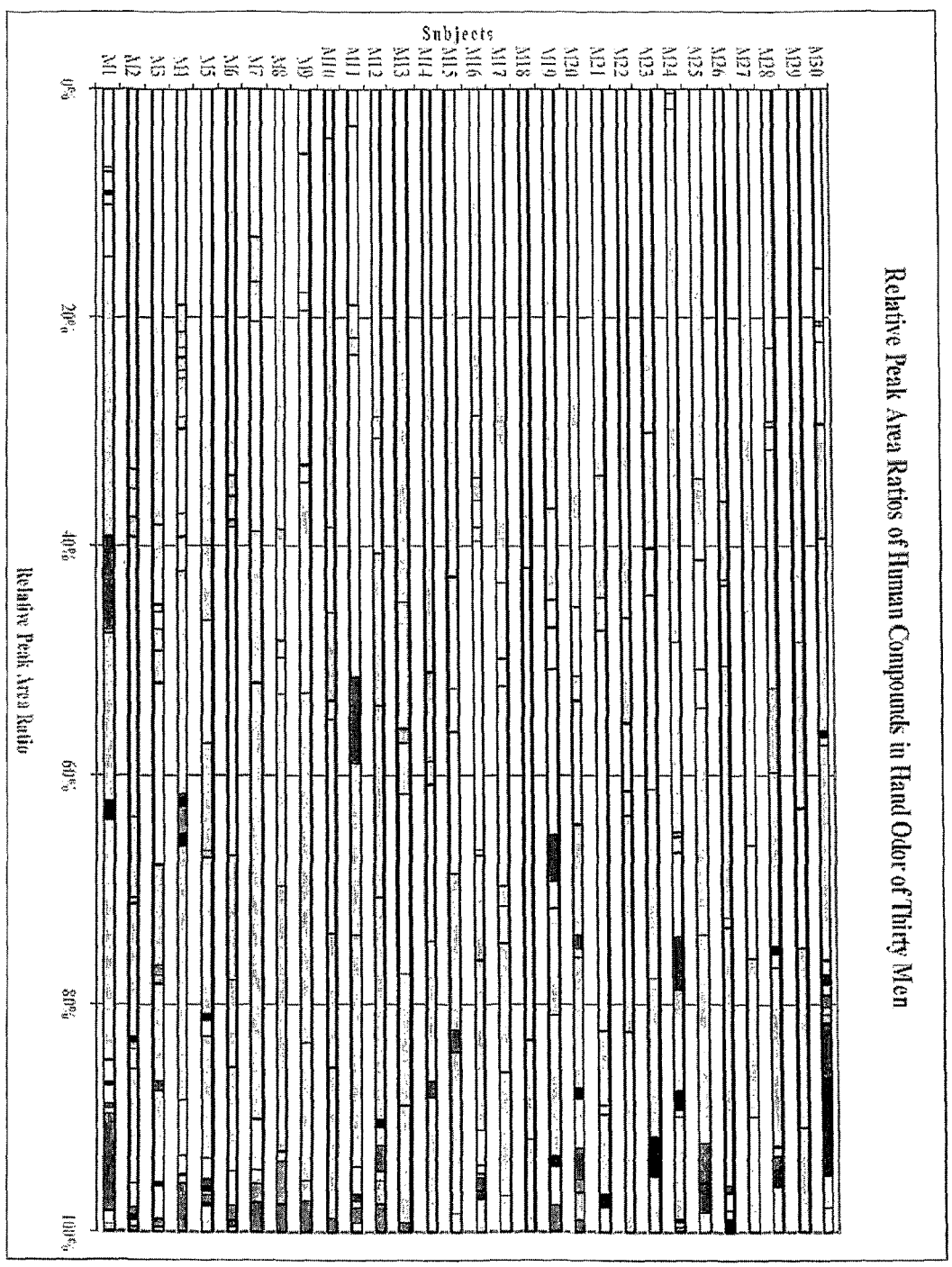
FIG. 32 shows the relative amounts of compounds identified in hand odor samples in thirty males studied.
Figure 33:
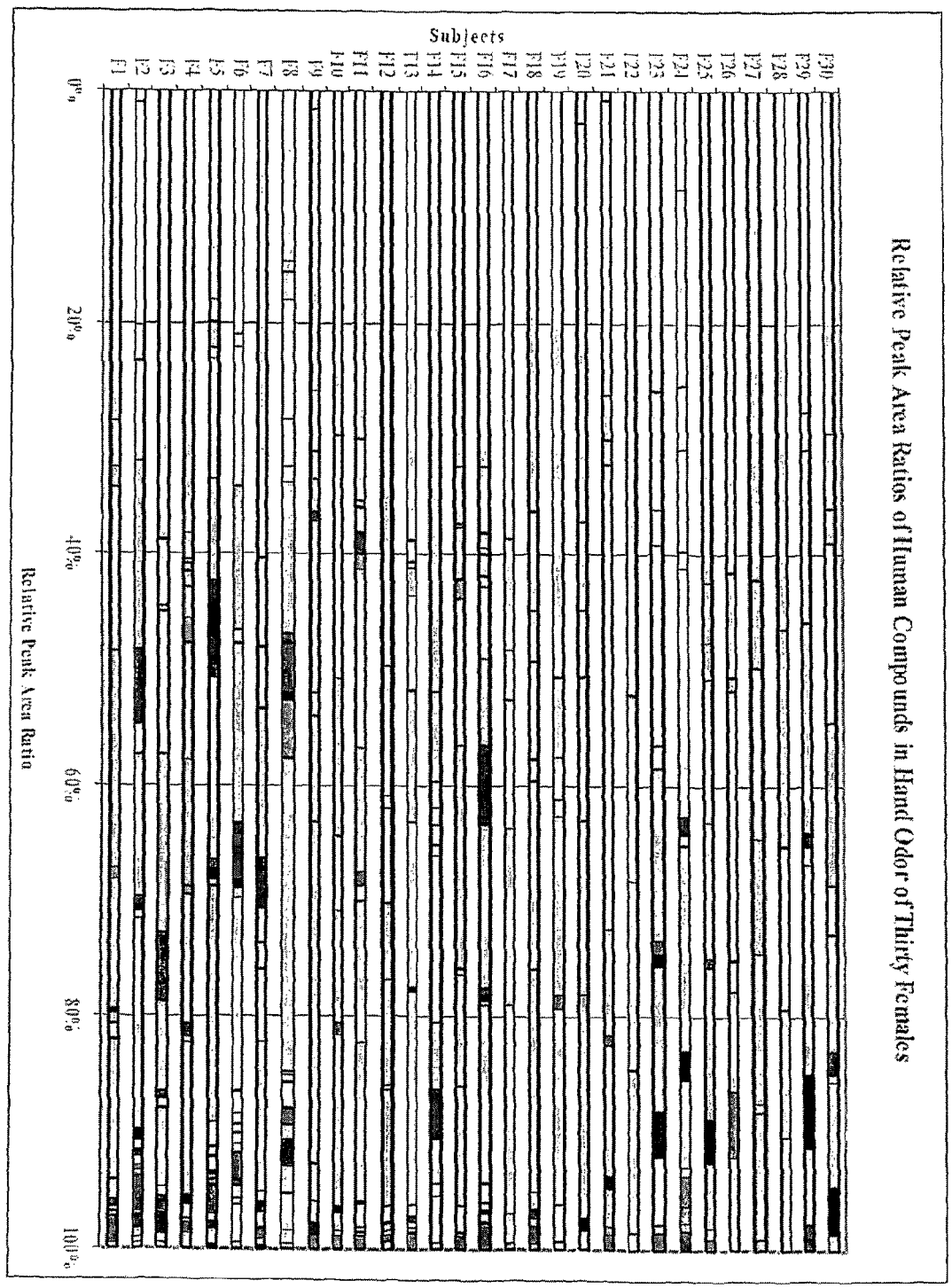
FIG. 33 shows the relative amounts of compounds identified in hand odor samples in thirty females studied.

FIG. 32 and FIG. 33 demonstrate the relative ratios of the human compounds extracted in the headspace above the collected hand odor samples for the population separated by gender. Differences in the ratio patterns between subjects are evident even for the high frequency compounds among individuals. It is uncertain whether scent identity lies within the ratio patterns of the common compounds between individuals, the presence of compounds which have a high variation between people, or whether it is a combination of the two factors. It is possible to distinguish VOCs from collected armpit samples between individuals based on relative peak area ratio patterns of the common compound extracted between multiple samplings of individuals, and that greater variability between the odor profiles among individuals can be achieved when the human compounds, which differ between individuals, are also considered.

The hand odor profiles evaluated were produced from a combination of sebaceous and eccrine secretions, without the influence of the apocrine glands as seen in armpit odor. The ability of canines to distinguish the odors of humans over long periods of time suggest that human scent is stable over time, or that portions of an individual's odor profile are stable even though elements of the odor may change. Alterations to portions of the odor of an individual may occur due to the influence of illness, the onset of puberty, the menstrual cycle in females, for example. Many of these factors directly affect the apocrine gland. The secretions obtained from the eccrine and sebaceous glands are less likely to be influenced by these changes, thereby more likely to produce the stable odor of an individual.

Comparison of Armpit and Hand Odor Profiles: Eight subjects participated in a hand odor population study. For each of these subjects, four females and four males, the VOCs determined in the odor collected from the armpit region and from the palms of the hands have been compared and are shown in Table 38. The odor profile produced from the hands and the armpit area of a single individual are similar. However, differences can be noted. This was an expected result due to the fact that these two regions of the body contain different types of sweat glands. The hand odor profiles were produced from a combination of sebaceous and eccrine secretions, whereas the armpit odor profiles were produced from a combination of sebaceous, eccrine, and apocrine secretions. Collected hand secretions are also less concentrated than armpit secretions that have been collected after physical activity. Qualitative similarities exist between the compounds present in the odor profiles produced for the hands and the armpit region for an individual.

TABLE 38

| Compound Name | F2 A | F2 H | F4 A | F4 H | F5 A | F5 H | F7 A | F7 H | M2 A | M2 H | M4 A | M4 H | M6 A | M6 H | M7 A | M7 H |
|---|---|---|---|---|---|---|---|---|---|---|---|---|---|---|---|---|
| Pyridine | X | | | | | | | | X | | | | | | | |
| Toluene | | | | | | | X | | | | X | | | | | |
| Hexanal | | | X | | | | | | | | | | | | | |
| 2-Furancarboxaldehyde | X | X | X | X | X | X | X | X | X | X | X | X | X | X | X | X |
| 2-Furanmethanol | X | X | X | X | X | X | X | X | X | X | X | X | | X | X | X |
| Heptanal | | | | X | | | | | | | | X | | | X | X |
| Hexanoic acid-methyl ester | | | X | | X | | | | X | | X | | | | | |
| α-Pinene | | | | | | | X | | | | | | | | | |
| Benzaldehyde | X | X | | | | | | | X | | | | X | | | X |
| β-Pinene | | | | | | | X | | | | | | | | | |
| Furancarboxylic acid-methyl ester | X | | X | X | X | | | | X | X | X | | | | X | |
| Phenol | X | X | X | X | X | X | X | X | X | X | X | X | X | X | X | X |
| 6-methyl-5-Hepten-2-one | X | X | X | X | | X | X | X | X | X | | X | X | X | | X |
| Octanal | X | | | | | | | | X | | | | | | | |
| Benzyl Alcohol | | | | | X | | | | | X | | | X | | | X |
| Propanedioic acid-dimethyl ester | | | X | X | | | | | | X | | | X | X | | X |
| Undecane | | X | | X | | | X | | | X | | X | X | X | | X |
| 1,6-Octadien-3-ol, 3,7-dimethyl- | | | | X | | | | | | | | | | | | X |
| Nonanal | X | X | X | X | X | X | X | X | X | X | X | X | X | X | X | X |
| Octanoic acid-methyl ester | X | | X | X | X | X | X | X | | | X | X | | | X | X |
| 2-Nonenal, (E)- | X | X | X | | | | X | X | | | | | | X | | X |
| Nonane, 1-chloro- | | | X | X | | | | | | | | | | | | |
| Acetic acid-phenylmethyl ester | | | | | X | | | | | | | | | | | |
| Nonanol | X | | | | | | | | | | X | | | | X | |
| Naphthalene | | X | | | | | X | | | X | | | X | X | | |
| Dodecane | X | X | X | | X | | X | X | X | X | | | X | | | |
| Decanal | X | X | X | X | X | X | X | X | X | X | X | X | X | X | X | X |
| Nonanoic acid-methyl ester | X | | X | X | X | X | X | | X | | X | X | X | X | | |
| Hexanedioic acid-dimethyl ester | X | X | X | X | X | X | | X | X | X | | X | X | X | | X |
| 2-Decenal, (E)- | X | | | | | | | | | X | | | | | | |
| Tridecane | X | X | | | X | X | X | X | X | X | | | X | | | |
| Undecanal | X | X | | | X | X | | | | | | | | | X | |
| Decanoic acid-methyl ester | X | | X | | X | X | | | | | | | X | | | |
| Tetradecane | X | | X | | X | X | X | | X | | X | | X | | X | X |
| Undecanoic acid-methyl ester | X | | | | X | | | | | | X | | X | | | |
| 6,10-dimethyl-5,9-Undecadien-2-one | X | X | X | X | X | X | X | X | X | X | X | X | X | X | X | X |
| Dodecanoic acid-methyl ester | X | | X | | | X | X | X | X | | X | | X | X | X | |
| Tetradecanal | X | | | | | | | | X | X | X | | | | | |
| 9-Dodecenoic acid-methyl ester | | | | | X | | | | | | | | | | | |
| Dodecanoic acid | | X | | X | X | X | | | | | X | | | X | | |
| 10-methyl-Dodecanoic acid-methyl ester | | X | | | | | | | | | X | | X | | | |
| Hexadecane | X | | | | X | | X | | X | | | | X | | | |
| Tridecanoic acid-methyl ester | X | | X | | X | | | | | | X | | X | | | |
| Heptadecane | X | | | | X | | X | | | | X | | X | | | |
| Tetradecanoic acid-methyl ester | X | | X | | X | | X | X | X | | X | X | X | | | |
| 12-methyltetradecanoic acid-methyl ester | | | X | | | | | | | | X | | | | | |
| Oleic Acid | | | | | X | | | | | | | | | | | |
| Pentadecanoic acid,-methyl ester | | | X | | X | | | | | | | | X | | | |
| Methyl 9-methyltetradecanoate | X | | | | X | | | | X | | | | X | | | |

TABLE 38-continued

| | Subject | | | | | | | | | | | | | |
|---|---|---|---|---|---|---|---|---|---|---|---|---|---|---|
| | F2 | | F4 | | F5 | | F7 | | M2 | | M4 | | M6 | M7 |
| | | | | | | | Body Region | | | | | | | |
| Compound Name | A | H | A | H | A | H | A | H | A | H | A | H | A | H |
| 7-Hexadecenoic acid,-methyl ester | | | X | | X | X | | | | | X | | X | |
| Hexadecanoic acid-methyl ester | | | X | | X | X | X | X | | | X | | X | |

Persistence of Collected Human Scent

Several different absorbent mediums were evaluated in this study. All gauze used in this study were DUKAL brand, 100% cotton, sterile, 2×2, 8 ply, gauze sponges (DUKAL Corporation, Syosset, N.Y.). The sterile gauze was not subjected to any additional sterilization processes. The glass beads were 3 mm, Spherical Soda Lime, Solid Glass Beads (Fisher Scientific, Pittsburgh, Pa., USA). Microscope Glass Slides (Fisher Scientific, Pittsburgh, Pa., USA) were also compared as potential scent storage mediums. A Metler AE 240 Analytical Balance was used to determine the mass of each gauze and glass slide cover sample, and an analytical microbalance (CAHN C-33, serial number: 77536, San Diego, Calif., USA) was used for the glass beads. Samples were stored in sterile plastic specimen dishes.

Each absorbent material sample was subjected to similar treatment to ensure accuracy of results. Female 1, Female 2, and Male 1 were asked to rinse their hands vigorously in deionized water for 3 minutes, then wait 5 minutes before handling an absorbent medium. For the gauze samples, subjects were asked to roll the gauze between their hands for 5 minutes. The glass bead samples were collected by asking the subjects to roll the beads between their hands for 5 minutes. The glass slide covers could not be rolled, so the subjects were asked to hold the slide covers firmly between the forefinger and thumb for 5 minutes.

After 5 minutes, the objects were allowed to sit for 15 minutes to cool, and then weighed again. Mass by difference was used to determine the initial scent weights present on the gauze, slide covers and beads. The scented materials along with non-scented representative reference materials were left open to the atmosphere in uncovered plastic containers inside an open cardboard box within an air-conditioned room and weighed for 84 days. The reference materials were used to account for environmental changes, such as humidity, and any weight changes in the reference materials were subtracted from the weights of the scented materials. Since the reference materials were stored under the same conditions as the scented materials, the environmental factors affecting the weights of the scented materials equally affected the reference materials. All changes in weight of the reference materials can be attributed to environmental factors, because they were handled with powderless latex gloves while being weighed on a clean analytical balance. Gloves were discarded after each weighing.

The data collected in the weight dissipation study is shown in Table 39, Table 40, and Table 41. The mass of the scent present on the media can be calculated by subtracting the initial mass, then adding a correctional factor determined from the differences in the blank mass.

TABLE 39

| | Blank | Gauze 1 (G1) | Gauze 2 (G2) | Gauze 3 (G3) | Correction Factor | Scent wt G1 | Scent wt G2 | Scent wt G3 |
|---|---|---|---|---|---|---|---|---|
| Initial mass | 597.73 | 605.08 | 596.52 | 606.06 | 0.00 | 0.00 | 0.00 | 0.00 |
| After scenting | | 605.77 | 599.68 | 608.58 | 0.00 | 0.69 | 3.16 | 2.52 |
| Day | | | | | | | | |
| 1 | 598.06 | 606.10 | 598.85 | 607.94 | 0.33 | 0.69 | 2.00 | 1.55 |
| 2 | 597.25 | 605.33 | 597.83 | 607.38 | −0.48 | 0.73 | 1.79 | 1.80 |
| 3 | 598.11 | 606.18 | 598.83 | 607.93 | 0.38 | 0.72 | 1.93 | 1.49 |
| 7 | 597.15 | 605.30 | 597.77 | 606.93 | −0.58 | 0.80 | 1.83 | 1.45 |
| 8 | 597.90 | 605.77 | 598.45 | 607.43 | 0.17 | 0.52 | 1.76 | 1.20 |
| 9 | 598.35 | 606.69 | 599.42 | 608.62 | 0.62 | 0.99 | 2.28 | 1.94 |
| 15 | 597.66 | 605.37 | 597.73 | 607.23 | −0.07 | 0.36 | 1.28 | 1.24 |
| 22 | 598.06 | 605.87 | 598.30 | 607.41 | 0.33 | 0.46 | 1.45 | 1.02 |
| 29 | 598.83 | 606.81 | 599.17 | 608.54 | 1.10 | 0.63 | 1.55 | 1.38 |
| 36 | 597.50 | 605.42 | 597.43 | 606.61 | −0.23 | 0.57 | 1.14 | 0.78 |
| 43 | 598.52 | 606.37 | 598.40 | 607.61 | 0.79 | 0.50 | 1.09 | 0.76 |
| 50 | 599.66 | 607.44 | 599.39 | 608.68 | 1.93 | 0.43 | 0.94 | 0.69 |
| 57 | 598.46 | 606.11 | 597.97 | 607.36 | 0.73 | 0.30 | 0.72 | 0.57 |
| 63 | 598.49 | 606.12 | 598.19 | 607.63 | 0.76 | 0.28 | 0.91 | 0.81 |
| 70 | 598.63 | 606.58 | 598.38 | 607.56 | 0.90 | 0.60 | 0.96 | 0.60 |
| 78 | 600.92 | 608.76 | 600.36 | 609.68 | 3.19 | 0.49 | 0.65 | 0.43 |
| 84 | 601.24 | 608.55 | 600.35 | 610.07 | 3.51 | −0.04 | 0.32 | 0.50 |

TABLE 40

|  | Blank | Slide 1 (S1) | Slide 2 (S2) | Slide 3 (S3) | Correction Factor | Scent wt S1 | Scent wt S2 | Scent wt S3 |
|---|---|---|---|---|---|---|---|---|
| Initial mass | 136.735 | 136.228 | 137.675 | 137.898 |  |  |  |  |
| After scenting |  | 136.233 | 137.685 | 137.905 | 0.000 | 0.005 | 0.010 | 0.007 |
| Day |  |  |  |  |  |  |  |  |
| 1 | 136.746 | 136.228 | 137.677 | 137.901 | 0.011 | −0.011 | −0.009 | −0.008 |
| 2 | 136.753 | 136.232 | 137.686 | 137.905 | 0.018 | −0.014 | −0.007 | −0.011 |
| 3 | 136.765 | 136.234 | 137.684 | 137.908 | 0.030 | −0.024 | −0.021 | −0.020 |
| 7 | 136.746 | 136.235 | 137.678 | 137.897 | 0.011 | −0.004 | −0.008 | −0.012 |
| 8 | 136.749 | 136.233 | 137.676 | 137.899 | 0.014 | −0.009 | −0.013 | −0.013 |
| 9 | 136.745 | 136.230 | 137.675 | 137.901 | 0.010 | −0.008 | −0.010 | −0.007 |
| 15 | 136.759 | 136.229 | 137.718 | 137.909 | 0.024 | −0.023 | 0.019 | −0.013 |
| 22 | 136.747 | 136.229 | 137.669 | 137.901 | 0.012 | −0.011 | −0.018 | −0.009 |
| 29 | 136.746 | 136.226 | 137.679 | 137.897 | 0.011 | −0.013 | −0.007 | −0.012 |
| 36 | 137.055 | 136.164 | 137.711 | 137.932 | 0.320 | −0.384 | −0.284 | −0.286 |
| 43 | 136.738 | 136.22 | 137.677 | 137.894 | 0.003 | −0.011 | −0.001 | −0.007 |
| 50 | 136.739 | 136.223 | 137.67 | 137.892 | 0.004 | −0.009 | −0.009 | −0.010 |
| 57 | 136.744 | 136.221 | 137.672 | 137.891 | 0.009 | −0.016 | −0.012 | −0.016 |
| 63 | 136.745 | 136.222 | 137.671 | 137.894 | 0.010 | −0.016 | −0.014 | −0.014 |
| 70 | 136.764 | 136.221 | 137.671 | 137.893 | 0.029 | −0.036 | −0.033 | −0.034 |
| 78 | 136.738 | 136.224 | 137.683 | 137.89 | 0.003 | −0.007 | 0.005 | −0.011 |
| 84 | 136.764 | 136.231 | 137.682 | 137.898 | 0.029 | −0.026 | −0.022 | −0.029 |

TABLE 41

|  | Blank | Set 1 | Set 2 | Set 3 | Correction Factor | Scent wt S1 | Scent wt S2 | Scent wt S3 |
|---|---|---|---|---|---|---|---|---|
| Initial mass | 136.735 | 136.228 | 137.675 | 137.898 |  |  |  |  |
| After scenting |  | 136.233 | 137.685 | 137.905 | 0.000 | 0.005 | 0.010 | 0.007 |
| Day |  |  |  |  |  |  |  |  |
| 1 | 136.746 | 136.228 | 137.677 | 137.901 | 0.011 | −0.011 | −0.009 | −0.008 |
| 2 | 136.753 | 136.232 | 137.686 | 137.905 | 0.018 | −0.014 | −0.007 | −0.011 |
| 3 | 136.765 | 136.234 | 137.684 | 137.908 | 0.030 | −0.024 | −0.021 | −0.020 |
| 7 | 136.746 | 136.235 | 137.678 | 137.897 | 0.011 | −0.004 | −0.008 | −0.012 |
| 8 | 136.749 | 136.233 | 137.676 | 137.899 | 0.014 | −0.009 | −0.013 | −0.013 |
| 9 | 136.745 | 136.230 | 137.675 | 137.901 | 0.010 | −0.008 | −0.010 | −0.007 |
| 15 | 136.759 | 136.229 | 137.718 | 137.909 | 0.024 | −0.023 | 0.019 | −0.013 |
| 22 | 136.747 | 136.229 | 137.669 | 137.901 | 0.012 | −0.011 | −0.018 | −0.009 |
| 29 | 136.746 | 136.226 | 137.679 | 137.897 | 0.011 | −0.013 | −0.007 | −0.012 |
| 36 | 137.055 | 136.164 | 137.711 | 137.932 | 0.320 | −0.384 | −0.284 | −0.286 |
| 43 | 136.738 | 136.22 | 137.677 | 137.894 | 0.003 | −0.011 | −0.001 | −0.007 |
| 50 | 136.739 | 136.223 | 137.67 | 137.892 | 0.004 | −0.009 | −0.009 | −0.010 |
| 57 | 136.744 | 136.221 | 137.672 | 137.891 | 0.009 | −0.016 | −0.012 | −0.016 |
| 63 | 136.745 | 136.222 | 137.671 | 137.894 | 0.010 | −0.016 | −0.014 | −0.014 |
| 70 | 136.764 | 136.221 | 137.671 | 137.893 | 0.029 | −0.036 | −0.033 | −0.034 |
| 78 | 136.738 | 136.224 | 137.683 | 137.89 | 0.003 | −0.007 | 0.005 | −0.011 |
| 84 | 136.764 | 136.231 | 137.682 | 137.898 | 0.029 | −0.026 | −0.022 | −0.029 |

Figure 34:
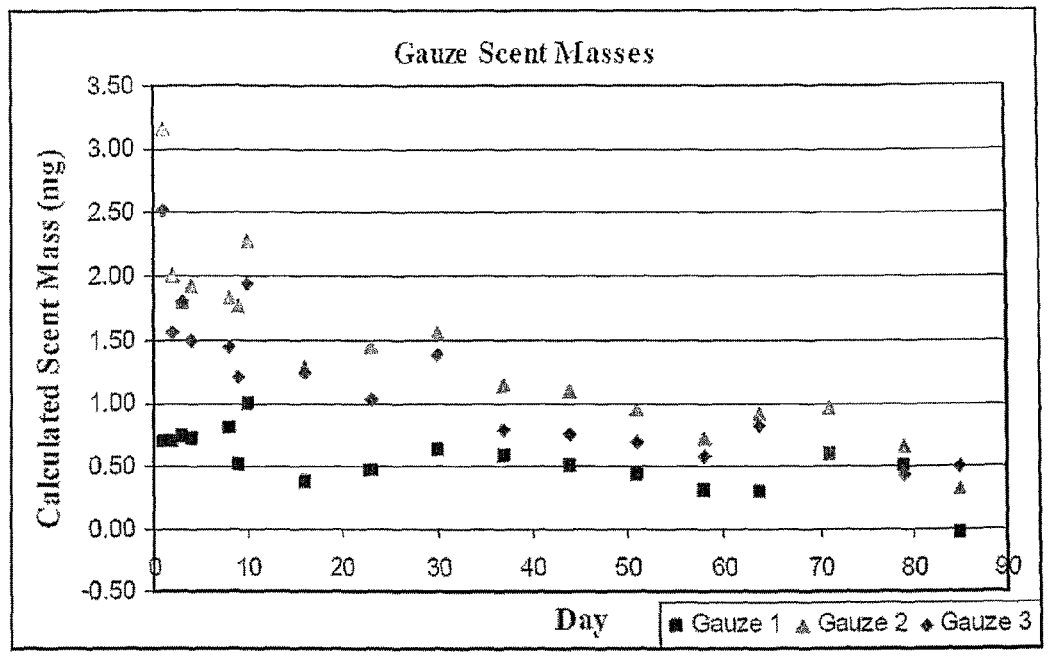
FIG. 34 shows trends of scent mass difference plotted versus time for a gauze medium.
Figure 35:
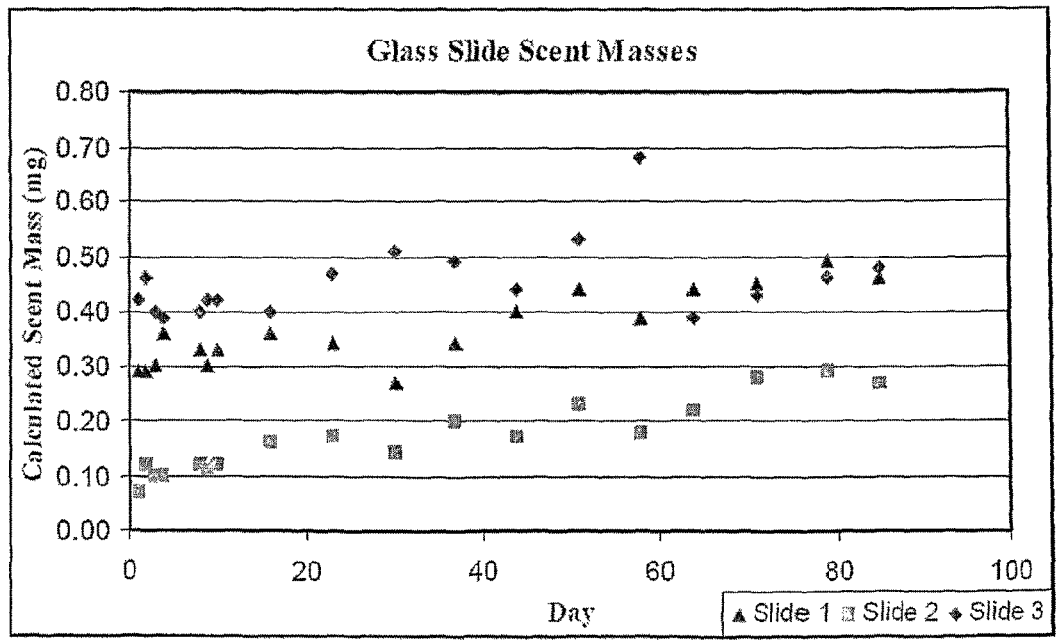
FIG. 35 shows trends of scent mass difference plotted versus time for a glass cover medium.

FIG. 34 and FIG. 35 demonstrate the trends of scent mass difference plotted versus time for the gauze and slide cover medium respectively. The scent collected on the gauze decreased over time, and began leveling off as the scent weight approached zero. While other factors may affect the mass of the gauze, as shown by the variation of the blank sample, the overall decrease in mass shows that environmental factors have a limited impact on the storage capabilities of the gauze. The initial weights of the "scent" for Female 1, Female 2, and Male 1 were 0.69 mg, 2.52 mg, and 3.16 mg, respectively. After eighty-four days of weighing, there was still weight present on the gauze scented by Male 1 and Female 2. It is expected that the mass of odiferous compounds would decrease over time because these compounds must diffuse into the air to produce a detectable scent. Thus, the amount of these compounds on the source object must decrease over time. The scent masses recorded on the glass beads indicate that environmental factors are more significant than actual scent weight, prohibiting glass beads from being a potential scent collection medium. The reason for the increase in mass is not certain, but the slides must be acquiring mass from environmental factors, which may or may not include contaminants that would alter the scent stored on the slide. Of the materials examined in this study, gauze has the most potential as a scent collection medium as demonstrated by the retention of a measurable quantity of scent for several months.

Solid Phase Micro-Extraction of Collected Hand Odor Samples Over Time

Supercritical fluid extraction (SFE) using methanol modified carbon dioxide was used as a pretreatment for the gauze. Gauze pads were DUKAL brand, sterile, 2×2, 8 ply, gauze sponges (DUKAL Corporation, Syosset, N.Y., USA). The vials used to hold the gauze were 10 mL glass, clear, screw top vials with PTFE/Silicone septa (SUPELCO, Bellefonte, Pa., USA). The extraction solvent for the pre-treatment of the gauze pads by supercritical fluid extraction was supercritical grade carbon dioxide (Air Products, Allentown, Pa., USA).

The methanol used as the modifier for the pre-treatment of the gauze pads was HPLC grade (Fisher Scientific, Pittsburgh, Pa., USA). The soap used by the subjects to wash the hands and forearms was Natural, Clear Olive Oil Soap from Life of the Party (North Brunswick, N.J., USA).

Hand odor samples Female 5 and Female 7 were evaluated after collection over a time period of twenty-eight days. The sampling protocol was as follows: 30 seconds of washing the hands and forearms with olive oil based soap, 2 min of rinsing the areas with cool water, 2 min of air drying, followed by 5 min of rubbing the palms of the hands over the forearms. A pre-treated 2×2 sterile gauze pad was then removed from the 10 mL glass vial using tweezers previously rinsed with a 10% bleach solution and placed in the palms of the subject's hands. The subjects then sampled themselves by holding the pre-treated gauze between the palms of their hands, walking outdoors for 10 min, then re-sealing the sample back into the 10 mL glass vial. All samples were stored in the 10 mL vials at room temperature, and allowed to sit for approximately 24 hrs prior to extraction. These storage conditions were chosen to simulate the conditions under which odor is collected for canine evaluation purposes. No attempt was made to control microbial interactions with the substrate because it may make contributions to the overall odor profile. The climatic conditions present during the samplings included an average temperature of 80° F. and an average humidity of 76%. DVB/CAR on PDMS fibers were used to extract the volatile organic compounds from the headspace of the vials containing the scented gauze. Exposures were conducted at room temperature for 21 hrs. All gauzes were pre-treated using SFE and extracted using the SPME-GC/MS method prior to use to assure their analytical cleanliness.

Figure 36:
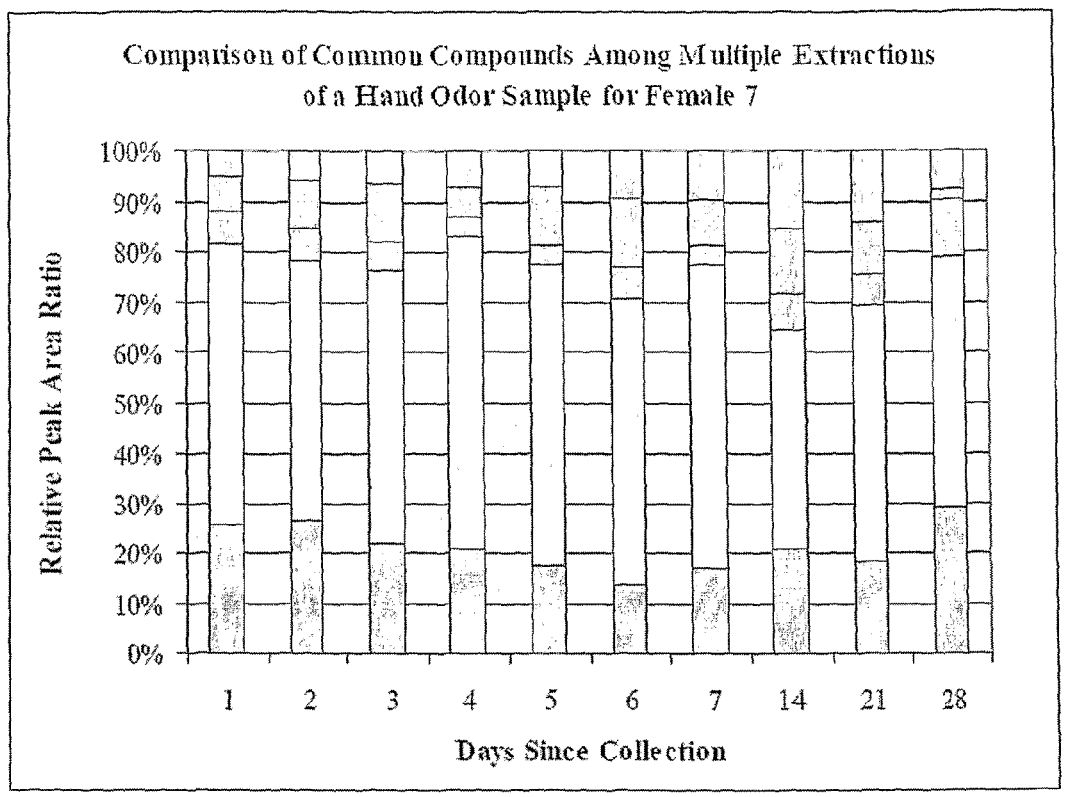
FIG. 36 shows the relative ratio patterns for common human compounds extracted through ten analyses over the four week period for Female 7.
Figure 37:
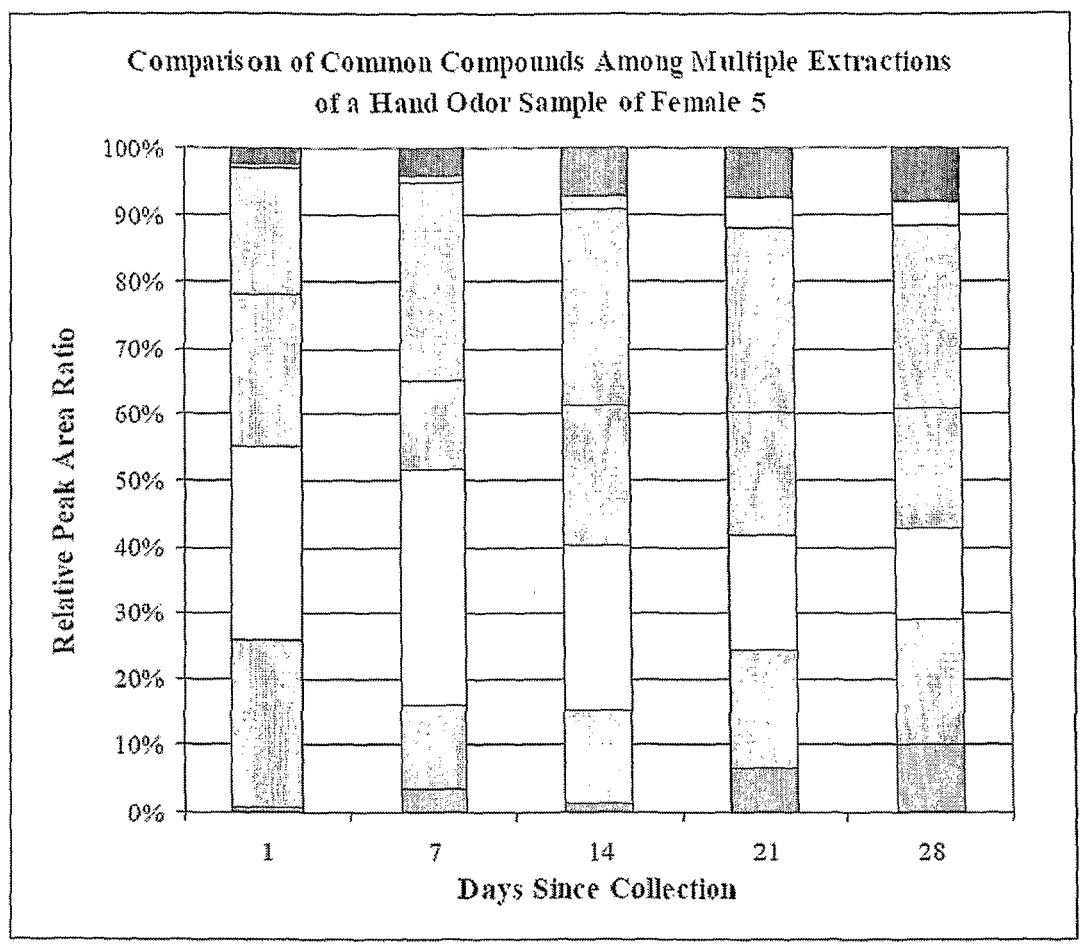
FIG. 37 shows the relative ratio patterns for common human compounds extracted through ten analyses over the four week period for Female 5.

Collected hand odor samples from Female 7 and Female 5 were evaluated over a four week period. Table 42 and Table 43 display the human compounds determined among ten SPME-GC/MS analyses across twenty-eight days for Female 7 and Female 5, respectively. There are compounds which persist over the time period, compounds which dissipate over the time period, as well as compounds which emerge as the time period progresses. FIG. 36 and FIG. 37 demonstrate the relative ratio patterns for the common human compounds extracted through the ten analyses over the four week period for Female 7 and Female 5, respectively.

TABLE 42

| Compound Name | Days Since Collection | | | | | | | | | |
|---|---|---|---|---|---|---|---|---|---|---|
| | 1 | 2 | 3 | 4 | 5 | 6 | 7 | 14 | 21 | 28 |
| Pyridine | X | | | | | | | | | |
| Toluene | | | | | X | X | X | | | X |
| 2-Butenal, 2-methyl- | X | | | | | | | | | |
| Butanoic acid | X | X | X | X | X | X | X | X | | X |
| 2-Furancarboxaldehyde | X | X | X | X | X | X | X | X | X | X |
| 2-Furanmethanol | X | X | X | X | X | X | X | | | |
| Benzene, 1,3-dimethyl- | | | | | | | X | | | X |
| p-Xylene | | | | | | X | X | X | | |
| Nonane | X | X | X | | | X | X | X | | |
| Propanedioic acid-dimethyl ester | X | X | X | X | X | | | | | |
| Benzene, 1,3,5-trimethyl- | | | | | | | X | X | | |
| Benzene, 1-ethyl-2-methyl- | | | | | | | X | X | | |
| Phenol | X | X | X | X | X | X | X | X | X | X |
| Decane | | | | | | | X | X | | |
| Undecane | | | | | | | X | X | | |
| Nonanal | X | X | X | X | X | X | X | X | X | X |
| Decanal | X | X | X | X | X | X | X | X | X | X |
| Dodecane | | | | | | | X | X | | |

TABLE 42-continued

| Compound Name | Days Since Collection | | | | | | | | | |
|---|---|---|---|---|---|---|---|---|---|---|
| | 1 | 2 | 3 | 4 | 5 | 6 | 7 | 14 | 21 | 28 |
| Hexanedioic acid-dimethyl ester | X | X | X | X | X | X | X | X | X | X |
| Tridecane | X | | | | | | | | | |
| Tetradecane | X | | | | | | | | | |
| 6,10-dimethyl-5,9-Undecadien-2-one | X | X | X | | | X | X | | X | |

TABLE 43

| Compound Name | Days Since Collection | | | | | | | | | |
|---|---|---|---|---|---|---|---|---|---|---|
| | 1 | 2 | 3 | 4 | 5 | 6 | 7 | 14 | 21 | 28 |
| Pyridine | X | | | | | | | | | |
| Toluene | | | | | | X | X | X | | |
| 2-Butenal, 2-methyl- | | X | | X | X | | | | | |
| Butanoic acid | X | X | X | X | X | X | X | X | X | X |
| 2-Furancarboxaldehyde | X | X | X | X | X | X | X | X | X | X |
| 2-Furanmethanol | X | X | X | | | | | | | |
| Benzene, 1,3-dimethyl- | | | | | | | X | | | X |
| p-Xylene | | | | | | X | X | X | | |
| Nonane | X | X | X | | | X | X | X | | |
| Benzene, 1,2,3-trimethyl- | | | | | | | X | X | | X |
| Benzene, 1-ethyl-2-methyl- | | | | | | | X | X | | |
| Phenol | X | X | X | X | X | X | X | X | X | X |
| Decane | | | | | | | X | X | | |
| Octanal | | X | X | | | | | | | |
| Eicosane | | | | | | | | X | X | |
| Undecane | X | | | | X | X | X | | | X |
| Nonanal | X | X | X | X | X | X | X | X | X | X |
| Octanoic acid-methyl ester | X | X | | | | | | | | |
| 2-Nonenal, (E)- | X | | | | | | | | | |
| Dodecane | | | | | | X | X | X | | |
| Decanal | X | X | X | X | X | X | X | X | X | X |
| Hexanedioic acid-dimethyl ester | X | X | X | X | X | X | X | | X | X |
| Tridecane | X | X | | X | X | X | X | | X | X |
| Undecanal | | | X | | X | | | | | |
| Decanoic acid | | | X | | X | | | | | |
| Tetradecane | X | X | X | X | X | X | X | X | X | X |
| Tetradecanal | | | | X | X | X | X | | | |
| 6,10-dimethyl-5,9-Undecadien-2-one | X | X | X | X | X | X | X | X | X | X |
| Undecanoic acid, 10-methyl-, methyl ester | X | | | | | | | | | |
| Dodecanoic acid-methyl ester | | | | | | X | X | X | | X |
| Dodecanoic acid | | | | | | X | | | | |

The first extraction of the hand odor sample for Female 7 contains fourteen human odor compounds and the first extraction for Female 5 contains sixteen. Female 7 had five compounds which were present in all of the analyses, including: 2-furancarboxaldehyde, phenol, nonanal, decanal, and hexanedioic acid-dimethyl ester. Female 5 had seven compounds which were present in all of the analyses, including: butanoic acid, 2-furancarboxaldehyde, phenol, nonanal, decanal, tetradecane, and 6,10-dimethyl-5,9-undecadien-2-one. Between the two samples, the eight compounds, which are present in all ten of the extractions, are a combination of high, medium, and low frequency compounds as listed in Table 36. As can be seen from FIG. 36 and FIG. 37, the ratio pattern of these common compounds is relatively stable throughout the four week period.

The analysis of Female 7 shows pyridine, tridecane, and tetradecane were only shown to be present in the first extraction. 2-Furanmethanol disappeared after day seven and propanedioic acid-methyl ester after day five. Butanoic acid was present in all of the extractions except on day twenty-one, which may be due to a problem with the SPME fiber as high amounts of siloxane were also seen during this extraction. The analysis of Female 5 shows the presence of pyridine and 10-methyl-undecanoic acid-methyl ester in only the first extraction and 2-furanmethanol disappears after day three. It is not clear whether these compounds are no longer present in the headspace or if their concentration has fallen below the ability of the SPME fiber to extract.

The analyses conducted on day six and day seven for both subjects show an increase in the number of compounds extracted. Most apparent on day six and seven in the profile of Female 7, is the appearance of many aliphatic/aromatic compounds which are not seen during any other analyses over the time period. This may indicate some sort of a change happening at this time interval after collection inside the vial, and may also be occurring in the scented gauze pads left open to the environment as shown previously in FIG. 34. Experiments utilizing canine evaluations of aged materials demonstrated a drop in performance when the canines were using materials that were aged between 1-2 weeks. After an initial significant decrease in performance, the canines were able to distinguish materials aged longer than two weeks with greater ability. The present disclosure suggests that when collected odor is stored within a glass container evaporation of the components is limited, and after an initial stabilization period, a steady state is reached which would explain the leveling off in performance of the canines. The evaluation of the composition of latent fingerprints over time has also shown that the majority of the changes in composition occur within the first week. The results shown here also suggest that the majority of the changes in headspace composition occur within the first seven days after collection.

The changes in collected odor may be due to the biological elements present on the materials after human contact. When evaluating odor which was obtained through direct contact, human secretions, skin cells, and bacteria may all be contained within the collection material. These biological constituents play a role in the creation of human odor when present on the body, removing them from such a moist, warm environment may alter their behavior and hence the compounds released. It may be possible through freezing the material, or storing it at lower temperatures to reduce the biological activity inside the closed system, thus reducing the alterations to the resulting volatile organic compounds. Another means for reducing the biological activity within the container is removing the biological components entirely through gamma radiation of the material after collection. Experiments utilizing canine evaluations after gamma radiation of scented materials have already shown that biological components in the collection materials are not necessary for sustaining the collected odor. It is possible that, after collection of human scent, if the materials are irradiated to remove all biological elements, then the collection material will only contain the chemical constituents and therefore will vary less over time during storage.

What is claimed:

1. A method of identifying or characterizing a human comprising the steps of:
   a) extracting human scent compounds from a sample from the human's palm or foot, wherein the sample comprises a plurality of human scent compounds; and
   b) analyzing the extracted human scent compounds to determine the identity and relative amount of each human scent compound, wherein the identity and relative amount of the human scent compounds identifies or characterizes the human.

2. The method of claim 1, further comprising collecting the sample using a collection fabric.

3. The method of claim 2, wherein the collection fabric comprises cotton.

4. The method of claim 2, further comprising cleaning the collection fabric prior to use in collecting the sample using super critical fluid extraction (SFE), and optionally a modifier, on the collection fabric.

5. The method of claim 4, wherein the modifier is selected from the group consisting of water, methanol, ethanol, propanol, isopropanol, and mixtures thereof.

6. The method of claim 2, wherein the collection fabric is in contact with the human for at least 15 minutes.

7. The method of claim 2, wherein the collection fabric is wiped on the human's skin.

8. The method of claim 1, wherein extracting comprises solid phase micro-extraction (SPME) using a fiber comprising divinylbenzne/carboxen on polydimethylsilozane (DVB/CAR/PDMS).

9. The method of claim 8, wherein SPME comprises extracting human scent compounds from the headspace of the sample.

10. The method of claim 1, wherein analyzing comprises gas chromatography, liquid chromatography, mass spectrometry, or a combination thereof.

11. A method of distinguishing a first human from a second human comprising the step of comparing a first analysis of extracted human scent compounds from a first sample of said first human and a second analysis of extracted human scent compounds from a second sample of said second human, wherein differences in (1) identity of human scent compounds, (2) relative concentrations of human scent compounds, or (3) both, distinguish said first human from said second human, and wherein said first sample is collected from said first human's foot or palm and said second sample is collected from said second human's foot or palm.

12. The method of claim 11, further comprising collecting said first sample of said first human and said second sample of said second human, wherein collecting comprises wiping a collection fabric on the first human or second human, wherein said collection fabric is cleaned prior to collection using supercritical fluid extraction optionally comprising a modifier.

13. The method of claim 12, wherein the modifier is selected from the group consisting of water, methanol, ethanol, isopropanol, propanol, and mixtures thereof.

14. The method of claim 11, wherein said first analysis and said second analysis results from analyzing said first sample and said second sample using gas chromatography, liquid chromatography, mass spectrometry, or a mixture thereof.

15. The method of claim 11, wherein the human scent compounds are extracted from a multiplicity of samples from each of said first human and said second human, and scent compounds in all samples in said multiplicity of samples for each of said first human and said second human, individually, are used to distinguish said first human from said second human.

16. The method of claim 15, wherein the multiplicity of samples is collected over at least about 7 days.

* * * * *